(12) United States Patent
Wakefield et al.

(10) Patent No.: US 12,258,563 B2
(45) Date of Patent: Mar. 25, 2025

(54) MODIFIED OLIGONUCLEOTIDES

(71) Applicant: EMPIRICO INC., San Diego, CA (US)

(72) Inventors: Darren H. Wakefield, Fitchburg, WI (US); Lauren Almeida, Madison, WI (US); David Rozema, Cross Plains, WI (US); Omri Gottesman, San Diego, CA (US); David Lewis, Madison, WI (US)

(73) Assignee: EMPIRICO INC., San Diego, CA (US)

( * ) Notice: Subject to any disclaimer, the term of this patent is extended or adjusted under 35 U.S.C. 154(b) by 18 days.

(21) Appl. No.: 18/190,819

(22) Filed: Mar. 27, 2023

(65) Prior Publication Data

US 2023/0304008 A1    Sep. 28, 2023

Related U.S. Application Data

(60) Provisional application No. 63/324,487, filed on Mar. 28, 2022, provisional application No. 63/429,756, filed on Dec. 2, 2022.

(51) Int. Cl.
| | | |
|---|---|---|
| *A61K 9/00* | (2006.01) | |
| *A61K 31/713* | (2006.01) | |
| *A61K 47/54* | (2017.01) | |
| *C12N 15/113* | (2010.01) | |

(52) U.S. Cl.
CPC .......... *C12N 15/113* (2013.01); *A61K 31/713* (2013.01); *A61K 47/543* (2017.08); *C12N 2310/14* (2013.01); *C12N 2310/315* (2013.01); *C12N 2310/321* (2013.01); *C12N 2310/322* (2013.01); *C12N 2310/3515* (2013.01)

(58) Field of Classification Search
CPC .................................................. A61K 47/543
See application file for complete search history.

(56) References Cited

U.S. PATENT DOCUMENTS

| | | | |
|---|---|---|---|
| 6,057,431 A | 5/2000 | Ishihara et al. | |
| 6,906,182 B2 | 6/2005 | Ts'o et al. | |
| 7,399,845 B2 | 7/2008 | Seth et al. | |
| 7,427,675 B2 | 9/2008 | Capaldi et al. | |
| 7,452,987 B2 | 11/2008 | Giese et al. | |
| 7,579,451 B2 | 8/2009 | Manoharan et al. | |
| 7,615,618 B2 | 11/2009 | Manoharan et al. | |
| 7,626,014 B2 | 12/2009 | Manoharan et al. | |
| 7,632,932 B2 | 12/2009 | Manoharan et al. | |
| 7,674,778 B2 | 3/2010 | Manoharan et al. | |
| 7,691,997 B2 | 4/2010 | Khvorova et al. | |
| 7,696,345 B2 | 4/2010 | Allerson et al. | |
| 7,723,512 B2 | 5/2010 | Manoharan et al. | |
| 7,772,387 B2 | 8/2010 | Manoharan et al. | |
| 7,875,733 B2 | 1/2011 | Bhat et al. | |
| 7,893,224 B2 | 2/2011 | Manoharan et al. | |
| 7,893,245 B2 | 2/2011 | Giese et al. | |
| 7,919,472 B2 | 4/2011 | Monia et al. | |
| 7,928,217 B2 | 4/2011 | Vornlocher et al. | |
| 8,013,136 B2 | 9/2011 | Manoharan et al. | |
| 8,242,257 B2 | 8/2012 | Beigelman et al. | |
| 8,268,980 B2 | 9/2012 | Seth et al. | |
| 8,273,866 B2 | 9/2012 | McSwiggen et al. | |
| 8,278,425 B2 | 10/2012 | Prakash et al. | |
| 8,324,370 B2 | 12/2012 | Giese et al. | |
| 8,334,373 B2 | 12/2012 | Vornlocher et al. | |
| 8,394,947 B2 | 3/2013 | Bhat et al. | |
| 8,470,988 B2 | 6/2013 | Manoharan et al. | |
| 8,501,703 B2 | 8/2013 | Bennett et al. | |
| 8,501,805 B2 | 8/2013 | Seth et al. | |
| 8,604,183 B2 | 12/2013 | Allerson et al. | |
| 8,637,478 B2 | 1/2014 | Bennett | |
| 8,648,185 B2 | 2/2014 | McSwigen et al. | |
| 8,790,919 B2 | 7/2014 | Migawa et al. | |
| 8,828,956 B2 | 9/2014 | Manoharan et al. | |
| 8,846,639 B2 | 9/2014 | Swayze et al. | |
| 8,877,439 B2 | 11/2014 | Butora et al. | |
| 8,883,752 B2 | 11/2014 | Swayze et al. | |

(Continued)

FOREIGN PATENT DOCUMENTS

| | | |
|---|---|---|
| EP | 2906255 A4 | 7/2016 |
| EP | 2321414 B1 | 1/2018 |

(Continued)

OTHER PUBLICATIONS

Tai, Chemical modulation of siRNA lipophilicity for efficient delivery, Journal of Controlled Release, 307 (2019) 98-107 (Year: 2019).*

Nishina, Efficient In Vivo Delivery of siRNA tot he Liver by Conjugation of alpha-Tocopherol, The American Society of Gene Therapy, vol. 16, No. 4, 734-740, Apr. 2008 (Year: 2008).*

Alterman et al.: A divalent siRNA chemical scaffold for potent and sustained modulation of gene expression throughout the central nervous system. Nat Biotechnol. 37:884-894 (2019).

(Continued)

*Primary Examiner* — Paul W Dickinson

(74) *Attorney, Agent, or Firm* — Wilson Sonsini Goodrich & Rosati

(57) ABSTRACT

Disclosed herein are compositions comprising modified oligonucleotides. In some embodiments, the oligonucleotide includes a hydrophobic moiety. In some embodiments, the oligonucleotide includes a vinyl phosphonate. In some embodiments, the oligonucleotide includes modified oligonucleotide sugars such as 2' modified ribose molecules. In some embodiments, the oligonucleotide includes modified internucleoside linkages such as phosphorothioate linkages. In some embodiments, the oligonucleotide includes an siRNA. In some embodiments, the siRNA comprises a duplex region with overhangs on either end.

19 Claims, No Drawings

Specification includes a Sequence Listing.

(56) References Cited

U.S. PATENT DOCUMENTS

| | | |
|---|---|---|
| 8,927,513 B2 | 1/2015 | Manoharan et al. |
| 8,933,215 B2 | 1/2015 | Giese et al. |
| 8,957,223 B2 | 2/2015 | Manoharan et al. |
| 8,962,580 B2 | 2/2015 | Manoharan et al. |
| 8,975,389 B2 | 3/2015 | Manoharan et al. |
| 8,987,435 B2 | 3/2015 | Swayze et al. |
| 8,993,738 B2 | 3/2015 | Prakash et al. |
| 8,993,746 B2 | 3/2015 | Vornlocher et al. |
| 9,012,421 B2 | 4/2015 | Migawa et al. |
| 9,045,754 B2 | 6/2015 | Bhanot et al. |
| 9,102,938 B2 | 8/2015 | Rajeev et al. |
| 9,127,033 B2 | 9/2015 | Prakash et al. |
| 9,127,272 B2 | 9/2015 | Esau et al. |
| 9,150,605 B2 | 10/2015 | Allerson et al. |
| 9,150,606 B2 | 10/2015 | Allerson et al. |
| 9,156,873 B2 | 10/2015 | Prakash et al. |
| 9,157,081 B2 | 10/2015 | Bennett et al. |
| 9,181,549 B2 | 11/2015 | Prakash et al. |
| 9,243,246 B2 | 1/2016 | Lim et al. |
| 9,260,471 B2 | 2/2016 | Cancilla et al. |
| 9,290,534 B2 | 3/2016 | Seth et al. |
| 9,290,760 B2 | 3/2016 | Rajeev et al. |
| 9,321,799 B2 | 4/2016 | Prakash et al. |
| 9,399,775 B2 | 7/2016 | Rajeev et al. |
| 9,453,043 B2 | 9/2016 | Manoharan et al. |
| 9,453,222 B2 | 9/2016 | Manoharan et al. |
| 9,512,164 B2 | 12/2016 | Manoharan et al. |
| 9,518,259 B2 | 12/2016 | Rigo et al. |
| 9,550,988 B2 | 1/2017 | Swayze |
| 9,598,693 B2 | 3/2017 | Esau et al. |
| 9,617,540 B2 | 4/2017 | Bhanot et al. |
| 9,708,607 B2 | 7/2017 | Rajeev et al. |
| 9,725,479 B2 | 8/2017 | Manoharan et al. |
| 9,738,895 B2 | 8/2017 | Swayze et al. |
| 9,758,784 B1 | 9/2017 | Giese et al. |
| 9,790,501 B2 | 10/2017 | Giese et al. |
| 9,796,974 B2 | 10/2017 | Rajeev et al. |
| 9,896,688 B2 | 2/2018 | Chang et al. |
| 9,914,922 B2 | 3/2018 | Freier et al. |
| 9,943,604 B2 | 4/2018 | Seth et al. |
| 9,970,005 B2 | 5/2018 | Cancilla et al. |
| 9,976,138 B2 | 5/2018 | Prakash et al. |
| 10,023,861 B2 | 7/2018 | Prakash et al. |
| 10,036,019 B2 | 7/2018 | Seth et al. |
| 10,087,210 B2 | 10/2018 | Prakash et al. |
| 10,131,908 B2 | 11/2018 | Manoharan et al. |
| 10,233,448 B2 | 3/2019 | Maier et al. |
| 10,266,825 B2 | 4/2019 | Allerson et al. |
| 10,337,007 B2 | 7/2019 | Freier et al. |
| 10,370,659 B2 | 8/2019 | Liang et al. |
| 10,385,337 B2 | 8/2019 | Manoharan et al. |
| 10,493,092 B2 | 12/2019 | Swayze |
| 10,570,169 B2 | 2/2020 | Seth et al. |
| 10,570,171 B2 | 2/2020 | Rajeev et al. |
| 10,584,335 B2 | 3/2020 | Lim et al. |
| 10,612,024 B2 | 4/2020 | Maier et al. |
| 10,612,027 B2 | 4/2020 | Maier et al. |
| 10,668,170 B2 | 6/2020 | Rajeev et al. |
| 10,676,738 B2 | 6/2020 | Prakash et al. |
| 10,689,648 B2 | 6/2020 | Carr et al. |
| 10,806,791 B2 | 10/2020 | Manoharan et al. |
| 10,995,336 B2 | 5/2021 | Schlegel et al. |
| 11,015,198 B2 | 5/2021 | Hauptmann et al. |
| 11,193,126 B2 | 12/2021 | Cancilla et al. |
| 11,400,161 B2 | 8/2022 | Cedillo et al. |
| 11,401,517 B2 | 8/2022 | Maier et al. |
| 11,406,716 B2 | 8/2022 | Rajeev et al. |
| 11,597,932 B2 | 3/2023 | Manoharan et al. |
| 2016/0053269 A1 | 2/2016 | Beigelman et al. |
| 2016/0264969 A1 | 9/2016 | Patel et al. |
| 2018/0256729 A1 | 9/2018 | Seth et al. |
| 2018/0362977 A1 | 12/2018 | Cancilla et al. |
| 2018/0371005 A1 | 12/2018 | Prakash et al. |
| 2019/0136234 A1 | 5/2019 | Prakash et al. |
| 2019/0270990 A1 | 9/2019 | Kordasiewicz et al. |
| 2019/0321387 A1 | 10/2019 | Prakash et al. |
| 2020/0063133 A1 | 2/2020 | Hauptmann et al. |
| 2020/0157548 A1 | 5/2020 | Prakash et al. |
| 2020/0239881 A1 | 7/2020 | Oestergaard et al. |
| 2020/0276221 A1 | 9/2020 | Swayze |
| 2020/0297853 A1 | 9/2020 | Manoharan et al. |
| 2020/0353097 A1 | 11/2020 | Rajeev et al. |
| 2020/0385722 A1 | 12/2020 | Prakash et al. |
| 2020/0392493 A1 | 12/2020 | Freier et al. |
| 2020/0392495 A1 | 12/2020 | Bethge et al. |
| 2020/0392499 A1 | 12/2020 | Carr et al. |
| 2020/0392509 A1 | 12/2020 | Oestergaard et al. |
| 2021/0017513 A1 | 1/2021 | Seth et al. |
| 2021/0017519 A1 | 1/2021 | Maier et al. |
| 2021/0155926 A1 | 5/2021 | Bethge et al. |
| 2021/0169917 A1 | 6/2021 | Viney et al. |
| 2021/0238594 A1 | 8/2021 | Parmar et al. |
| 2021/0238595 A1 | 8/2021 | Matsuda et al. |

FOREIGN PATENT DOCUMENTS

| | | |
|---|---|---|
| WO | WO-9302093 A1 | 2/1993 |
| WO | WO-2006119619 A1 | 11/2006 |
| WO | WO2011139702 A2 | 11/2011 |
| WO | WO-2019161213 A1 | 8/2019 |
| WO | WO-2020072883 A1 | 4/2020 |
| WO | WO-2020072887 A1 | 4/2020 |
| WO | WO-2020097044 A1 | 5/2020 |
| WO | WO-2020236600 A1 | 11/2020 |
| WO | WO-2021092371 A2 | 5/2021 |
| WO | WO-2022031433 A1 | 2/2022 |
| WO | WO-2023192830 A2 | 10/2023 |

OTHER PUBLICATIONS

Bachur et al.: Microsomal Synthesis of Fatty Acid Amides. The Journal of Biological Chemistry. 241(6):1308-1313 (1966).

Boeroeczky et al.: Cluster analysis as selection and dereplication tool for the identification of new natural compounds from large sample sets. Chemistry & Biodiversity. 3(6):622-634 (2006).

Cheng et al.: Stem-loop RT-PCR quantification of siRNAs in vitro and in vivo. Oligonucleotides 19:203-208 (S2009).

Chiaberge et al.: Amides in Bio-oil by Hydrothermal Liquifaction of Organic Wastes: A Mass Spectrometric Study of the Thermochemical Reaction Products of Binary Mixtures of Amino Acids and Fatty Acids. Energy & Fuels. 27(9):5287-5297 (2013).

Croce et al.: A Model Study to Unravel the Complexity of Bio-Oil from Organic Wastes. ChemSusChem. 10(1):171-181 (2017).

Dallagnol et al.: Flavonoids and Phenylethylamides are Pivotal Factors Affecting the Antimicrobial Properties of Stingless Bee Honey. Journal of Agricultural and Food Chemistry. 70(39):12596-12603 (2022).

Di Fabio et al.: Discovery of novel anti-HIV active G-quadruplex-forming oligonucleotides. Chemical Communications. 47(8):2363-2365 (2011).

Haraszti et al.: 5'-Vinylphosphonate improves tissue accumulation and efficacy of conjugated siRNAs in vivo. Nucleic Acids Res. 45(13):7581-7592 (2017).

Matayeva et al.: Elucidation of reaction pathways of nitrogenous species by hydrothermal liquefaction process of model compounds. Fuel. 240:169-178 (2019).

Njoo et al.: In vivo SiRNA transfection and gene knockdown in spinal cord via rapid noninvasive lumbar intrathecal injections in mice. J Vis Exp. (85):e51229 (2014).

Pongs et al.: Affinity labeling of ribosomes. II. Synthesis of a chemically reactive analog of the initiation codon. Its reaction with ribosomes of *Escherichia coli*. Hoppe-Seyler's nZeitschrift Physiologische Chemis. 356(4):449-458 (1975).

Proschak et al.: Cytotoxic Fatty Acid Amides from Xenorhabdus. ChemBioChem. 12(13):2011-2015 (2011).

Romanucci et al.: Kinetic ESI-MS studies of potent anti-HIV aptamers based on the G-quadruplex forming sequence d(TGGGAG). ACS Medicinal Chemistry Letters. 7(3):256-260: (2016).

Romanucci et al.: New findings on the d(TGGGAG) sequence: Surprising anti-HIV-1 activity. European Journal of Medicinal Chemistry. 145:425-430 (2018).

(56) References Cited

OTHER PUBLICATIONS

Shiono et al.: N-Phenethylhexadecanamide from the edible muschroom *Laetiporus sulphureus*. Natural Product Research. 19(4):363-366 (2005).
Vandevoorde et al.: Modifications of the Ethanolamine Head in N-Palmitoylethanolamine: Synthesis and Evaluation of New Agents Interfering with the Metabolism of Anandamide. Journal of Medicinal Chemistry. 46(8):1440-1448 (2003).
Wang et al.: Anticonvulsant Activity of Bombyx batryticatus and Analysis of Bioactive Extracts Based on UHLPLC-Q-TOF MS/MS and Molecular Networking. Molecules. 27:8315 (2022).
Wang et al.: Constituents of Microsorum insigne. Chemistry of Natural Compounds. 53(4):789-790 (2017).
Wang et al.: Eco-Friendly Production of Fatty Amides Using 1-Monoacylglycerols as Acy Donors. ACS Sustainable Chemistry & Engineering. 8(25):9589-9596 (2020).
PCT/US2023/065000 Invitation to Pay Additional Fees dated Jun. 26, 2023.

\* cited by examiner

MODIFIED OLIGONUCLEOTIDES

CROSS REFERENCE

This application claims the benefit of U.S. Provisional Application No. 63/324,487, filed Mar. 28, 2022, and U.S. Provisional Application No. 63/429,756, filed Dec. 2, 2022, both of which applications are incorporated herein by reference.

SEQUENCE LISTING

The present application is being filed along with a Sequence Listing in electronic format. The Sequence Listing is provided as a file entitled 54462-739201_US.xml, created Mar. 27, 2023, which is 541 kilobytes in size. The information in the electronic format of the Sequence Listing is incorporated by reference in its entirety.

BACKGROUND

There is a need in the art for improved oligonucleotides for reducing gene expression.

SUMMARY OF THE INVENTION

Described herein, in some embodiments, are compositions comprising an oligonucleotide that targets an mRNA and when administered in an effective amount reduces a target mRNA or protein level. Described herein, in some embodiments, are compositions comprising a small interfering RNA (siRNA) comprising a sense strand, an antisense strand, and a lipid moiety connected to an end of the sense or antisense strand; wherein the lipid moiety comprises a phenyl or cyclohexyl linker, wherein the linker is connected to a lipid and to the end of the sense or antisense strand. The lipid moiety may be connected to a 5' or 3' end of the sense or antisense strand. In some embodiments, the lipid and the end of the sense or antisense strand are connected to the phenyl or cyclohexyl linker in the 1,4; 1,3; or 1,2 substitution pattern (e.g. the para, meta, or ortho phenyl configuration). In some embodiments, the lipid and the end of the sense or antisense strand are connected to the phenyl or cyclohexyl linker in the 1,4 (para phenyl) configuration. In some embodiments, the lipid moiety comprises the following structure:

wherein the dotted line indicates a connection (e.g. a covalent connection) to the end of the sense or antisense strand and R is an alkyl group containing 4-18 carbons. In some embodiments, R is not an octane. In some embodiments, R is an alkyl group containing 4-7 or 9-18 carbons. In some embodiments, the lipid moiety comprises the following structure:

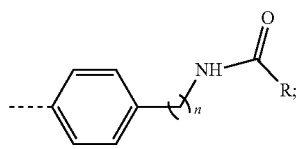

wherein the dotted line indicates a connection (e.g. a covalent connection) to the end of the sense or antisense strand, n is 1-3, and R is an alkyl group containing 4-18 carbons. In some embodiments, the lipid moiety comprises the following structure:

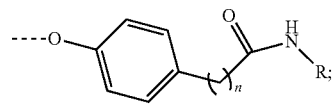

wherein the dotted line indicates a connection (e.g. a covalent connection) to the end of the sense or antisense strand, n is 0-3, and R is an alkyl group containing 4-18 carbons. In some embodiments, the lipid moiety comprises the following structure:

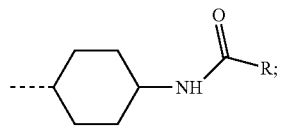

wherein the dotted line indicates a connection (e.g. a covalent connection) to the end of the sense or antisense strand and R is an alkyl group containing 4-18 carbons. In some embodiments, the lipid moiety comprises any one of the following structures:

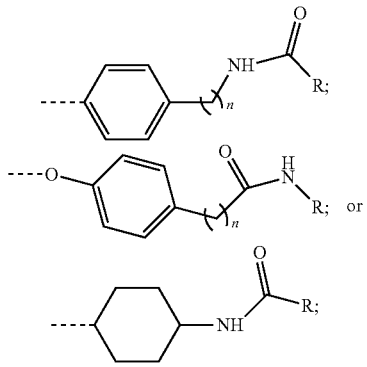

wherein the dotted line indicates a connection to the end of the sense or antisense strand, n is 0-3, and R is an alkyl group containing 4-18 carbons. In some embodiments, the lipid moiety comprises a lipid moiety depicted in Table 1. In some embodiments, the lipid moiety is connected to the 5' end of the sense strand or antisense strand. In some embodiments, the lipid moiety is connected to the 5' end of the sense strand. In some embodiments, the lipid moiety is connected through a phosphate to the 5' end of the sense strand or antisense strand. In some embodiments, the lipid moiety is connected to an end of the sense strand. In some embodiments, the antisense strand comprises a vinyl phosphonate. In some embodiments, the antisense strand comprises a 5' vinyl phosphonate. In some embodiments, the sense strand or antisense strand comprises one or two phosphorothioate linkages at a 5' or 3' end of the sense strand or antisense strand. In some embodiments, the antisense strand comprises one or two 5' phosphorothioate linkages. For example, there may be a phosphorothioate between the first and second nucleotides from the 5' end of the antisense strand, or there may be phosphorothioates between the first, second and third nucleotides from the 5' end of the antisense strand. In some embodiments, the antisense strand comprises one or two 3' phosphorothioate linkages. For example, there may be a phosphorothioate between the first and second nucleotides from the 3' end of the antisense strand, or there may be phosphorothioates between the first, second and third nucleotides from the 3' end of the antisense strand. In some embodiments, the sense strand comprises one or two 5' phosphorothioate linkages. For example, there may be a phosphorothioate between the first and second nucleotides from the 5' end of the sense strand, or there may be phosphorothioates between the first, second and third nucleotides from the 5' end of the sense strand. In some embodiments, the sense strand does not comprise one or two 5' phosphorothioate linkages. For example, in some embodiments, there are no phosphorothioates between the last 3 nucleotides at the 5' end of the sense strand. In some embodiments, the sense strand comprises 5' phosphate linkages. In some embodiments, the sense strand comprises one or two 3' phosphorothioate linkages. For example, there may be a phosphorothioate between the first and second nucleotides from the 3' end of the sense strand, or there may be phosphorothioates between the first, second and third nucleotides from the 3' end of the sense strand. In some embodiments, any one of the following is true with regard to the sense strand: all purine nucleosides comprise 2' fluoro, and all pyrimidine nucleosides are modified with a mixture of 2' fluoro and 2'-O-methyl; all purine nucleosides comprise 2'-O-methyl, and all pyrimidine nucleosides are modified with a mixture of 2' fluoro and 2'-O-methyl; all purine nucleosides comprise 2' fluoro, and all pyrimidine nucleosides comprise 2'-O-methyl; all pyrimidine nucleosides comprise 2' fluoro, and all purine nucleosides are modified with a mixture of 2' fluoro and 2'-O-methyl; all pyrimidine nucleosides comprise 2'-O-methyl, and all purine nucleosides are modified with a mixture of 2' fluoro and 2'-O-methyl; or all pyrimidine nucleosides comprise 2' fluoro, and all purine nucleosides comprise 2'-O-methyl; with the proviso that in any of the foregoing, the sense strand may include a 2' deoxy nucleoside. In some embodiments, the sense strand includes the 2' deoxy nucleoside. In some embodiments, the sense strand does not include the 2' deoxy nucleoside. In some embodiments, any one of the following is true with regard to the antisense strand: all purine nucleosides comprise 2' fluoro, and all pyrimidine nucleosides are modified with a mixture of 2' fluoro and 2'-O-methyl; all purine nucleosides comprise 2'-O-methyl, and all pyrimidine nucleosides are modified with a mixture of 2' fluoro and 2'-O-methyl; all purine nucleosides comprise 2'-O-methyl, and all pyrimidine nucleosides comprise 2' fluoro; all pyrimidine nucleosides comprise 2' fluoro, and all purine nucleosides are modified with a mixture of 2' fluoro and 2'-O-methyl; all pyrimidine nucleosides comprise 2'-O-methyl, and all purine nucleosides are modified with a mixture of 2' fluoro and 2'-O-methyl; or all pyrimidine nucleosides comprise 2'-O-methyl, and all purine nucleosides comprise 2' fluoro. In some embodiments, any one of the following is true with regard to the sense strand or antisense strand, with the proviso that the sense strand or antisense strand may include a deoxy nucleoside: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2' fluoro modified purines, and all pyrimidines comprise 2'-O-methyl modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2' fluoro modified pyrimidines, and all purines comprise 2'-O-methyl modified purines. In some embodiments, any one of the following is true with regard to the sense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2' fluoro modified purines, and all pyrimidines comprise 2'-O-methyl modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2' fluoro modified pyrimidines, and all purines comprise 2'-O-methyl modified purines. In some embodiments, any one of the following is true with regard to the sense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2' fluoro modified purines, and all pyrimidines comprise 2'-O-methyl modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2' fluoro modified pyrimidines, and all purines comprise 2'-O-methyl modified purines. In some embodiments, any one of the following is true with regard to the sense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2' fluoro modified purines, and all pyrimidines comprise 2'-O-methyl modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2' fluoro modified pyrimidines, and all purines comprise 2'-O-methyl modified purines; with the proviso that in any of the foregoing, the sense strand may include a deoxy nucleoside. In some embodiments, the sense strand does not include a deoxy nucleoside. In some embodiments, any one of the following is true with regard to the sense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2' fluoro modified purines, and all pyrimidines comprise 2'-O-methyl modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2' fluoro modified pyrimidines, and all purines comprise 2'-O-methyl modified purines. In some embodiments, any one of the following is true with regard to the antisense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2'-O-methyl modified purines, and all pyrimidines comprise 2' fluoro modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2'-O-methyl modified pyrimidines, and all purines comprise 2' fluoro modified purines. The sense strand may include a 2-deoxy modification at position 9.

Described herein, in some embodiments, are compositions comprising: a small interfering RNA (siRNA) comprising a sense strand and an antisense strand; wherein the antisense strand comprises a 5' end comprising a vinyl phosphonate and 2 phosphorothioate linkages, and a 3' end comprising 2 phosphorothioate linkages; wherein the sense strand comprises a 5' end comprising a hydrophobic moiety, and a 3' end comprising 2 phosphorothioate linkages; wherein any one of the following is true with regard to the sense strand, with the proviso that the sense strand may include a 2' deoxy nucleoside: all purine nucleosides comprise 2' fluoro, and all pyrimidine nucleosides are modified with a mixture of 2' fluoro and 2'-O-methyl, all purine nucleosides comprise 2'-O-methyl, and all pyrimidine nucleosides are modified with a mixture of 2' fluoro and 2'-O-methyl, all purine nucleosides comprise 2' fluoro, and all pyrimidine nucleosides comprise 2'-O-methyl, all pyrimidine nucleosides comprise 2' fluoro, and all purine nucleosides are modified with a mixture of 2' fluoro and 2'-O-methyl, all pyrimidine nucleosides comprise 2'-O-methyl, and all purine nucleosides are modified with a mixture of 2' fluoro and 2'-O-methyl, or all pyrimidine nucleosides comprise 2' fluoro, and all purine nucleosides comprise 2'-O-methyl; and wherein any one of the following is true with regard to the antisense strand: all purine nucleosides comprise 2' fluoro, and all pyrimidine nucleosides are modified with a mixture of 2' fluoro and 2'-O-methyl, all purine nucleosides comprise 2'-O-methyl, and all pyrimidine nucleosides are modified with a mixture of 2' fluoro and 2'-O-methyl, all purine nucleosides comprise 2'-O-methyl, and all pyrimidine nucleosides comprise 2' fluoro, all pyrimidine nucleosides comprise 2' fluoro, and all purine nucleosides are modified with a mixture of 2' fluoro and 2'-O-methyl, all pyrimidine nucleosides comprise 2'-O-methyl, and all purine nucleosides are modified with a mixture of 2' fluoro and 2'-O-methyl, or all pyrimidine nucleosides comprise 2'-O-methyl, and all purine nucleosides comprise 2' fluoro. In some embodiments, the sense strand includes the 2' deoxy nucleoside. In some embodiments, the sense strand does not include the 2' deoxy nucleoside. Described herein, in some embodiments, are compositions comprising a small interfering RNA (siRNA) comprising a sense strand and an antisense strand; wherein the antisense strand comprises a 5' end comprising a vinyl phosphonate and 2 phosphorothioate linkages, and a 3' end comprising 2 phosphorothioate linkages; wherein the sense strand comprises a 5' end comprising a hydrophobic moiety, and a 3' end comprising 2 phosphorothioate linkages; wherein any one of the following is true with regard to the sense strand: all purines comprise 2' fluoro modified purines, and all pyrimidines comprise a mixture of 2' fluoro and 2'-O-methyl modified pyrimidines, all purines comprise 2'-O-methyl modified purines, and all pyrimidines comprise a mixture of 2' fluoro and 2'-O-methyl modified pyrimidines, all purines comprise 2' fluoro modified purines, and all pyrimidines comprise 2'-O-methyl modified pyrimidines, all pyrimidines comprise 2' fluoro modified pyrimidines, and all purines comprise a mixture of 2' fluoro and 2'-O-methyl modified purines, all pyrimidines comprise 2'-O-methyl modified pyrimidines, and all purines comprise a mixture of 2' fluoro and 2'-O-methyl modified purines, or all pyrimidines comprise 2' fluoro modified pyrimidines, and all purines comprise 2'-O-methyl modified purines; and wherein any one of the following is true with regard to the antisense strand: all purines comprise 2' fluoro modified purines, and all pyrimidines comprise a mixture of 2' fluoro and 2'-O-methyl modified pyrimidines, all purines comprise 2'-O-methyl modified purines, and all pyrimidines comprise a mixture of 2' fluoro and 2'-O-methyl modified pyrimidines, all purines comprise 2' fluoro modified purines, all pyrimidines comprise 2'-O-methyl modified pyrimidines, all pyrimidines comprise 2' fluoro modified pyrimidines, and all purines comprise a mixture of 2' fluoro and 2'-O-methyl modified purines, all pyrimidines comprise 2'-O-methyl modified pyrimidines, and all purines comprise a mixture of 2' fluoro and 2'-O-methyl modified purines, or all pyrimidines comprise 2'-O-methyl modified pyrimidines, and all purines comprise 2' fluoro modified purines; all with the proviso that the sense strand may include a deoxy nucleoside. In some embodiments, the sense strand does not include a deoxy nucleoside. Described herein, in some embodiments, are compositions comprising a small interfering RNA (siRNA) comprising a sense strand and an antisense strand; wherein the antisense strand comprises a 5' end comprising a vinyl phosphonate and 2 phosphorothioate linkages, and a 3' end comprising 2 phosphorothioate linkages; wherein the sense strand comprises a 5' end comprising a hydrophobic moiety, and a 3' end comprising 2 phosphorothioate linkages; wherein any one of the following is true with regard to the sense strand: all purines comprise 2' fluoro modified purines, and all pyrimidines comprise a mixture of 2' fluoro and 2'-O-methyl modified pyrimidines, all purines comprise 2'-O-methyl modified purines, and all pyrimidines comprise a mixture of 2' fluoro and 2'-O-methyl modified pyrimidines, all purines comprise 2' fluoro modified purines, and all pyrimidines comprise 2'-O-methyl modified pyrimidines, all pyrimidines comprise 2' fluoro modified pyrimidines, and all purines comprise a mixture of 2' fluoro and 2'-O-methyl modified purines, all pyrimidines comprise 2'-O-methyl modified pyrimidines, and all purines comprise a mixture of 2' fluoro and 2'-O-methyl modified purines, or all pyrimidines comprise 2' fluoro modified pyrimidines, and all purines comprise 2'-O-methyl modified purines; and wherein any one of the following is true with regard to the antisense strand: all purines comprise 2' fluoro modified purines, and all pyrimidines comprise a mixture of 2' fluoro and 2'-O-methyl modified pyrimidines, all purines comprise 2'-O-methyl modified purines, and all pyrimidines comprise a mixture of 2' fluoro and 2'-O-methyl modified pyrimidines, all purines comprise 2'-O-methyl modified purines, and all pyrimidines comprise 2' fluoro modified pyrimidines, all pyrimidines comprise 2' fluoro modified pyrimidines, and all purines comprise a mixture of 2' fluoro and 2'-O-methyl modified purines, all pyrimidines comprise 2'-O-methyl modified pyrimidines, and all purines comprise a mixture of 2' fluoro and 2'-O-methyl modified purines, or all pyrimidines comprise 2'-O-methyl modified pyrimidines, and all purines comprise 2' fluoro modified purines. In some embodiments, the 5' end of the sense strand comprises two nucleotides linked via phosphate linkages, and not by a phosphorothioate linkage. In some embodiments, the 5' end of the sense strand comprises two nucleosides linked via phosphate linkages, and not by a phosphorothioate linkage, and the 3' end of the sense strand comprises two nucleosides linked via phosphorothioate linkages. In some embodiments, the 5' end of the sense strand further comprises 1 or 2 phosphorothioate linkages. In some embodiments, the hydrophobic moiety comprises a lipid connected to the 5' end of the sense strand by a phenyl or cyclohexyl linker. In some embodiments, the lipid and the 5' end of the sense strand are connected to the phenyl or cyclohexyl linker in the 1,4; 1,3; or 1,2 substitution patterns (e.g. para, meta, or ortho for phenyl configuration). In some embodiments, the lipid and the 5' end of the sense strand are connected to the phenyl or cyclohexyl linker in the 1,4 (para phenyl) configuration. In some embodiments, the hydrophobic moiety comprises any one of the following structures:

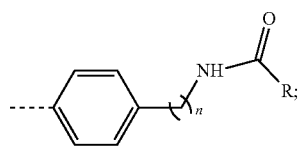

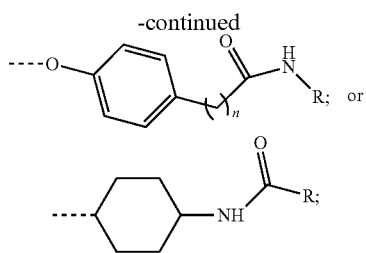

wherein the dotted line indicates a connection to the end of the sense or antisense strand, n is 1-3, and R is an alkyl group containing 4-18 carbons. In some embodiments, the hydrophobic moiety comprises the following structure:

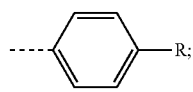

wherein the dotted line indicates a connection (e.g. a covalent connection) to the end of the sense or antisense strand and R is an alkyl group containing 4-18 carbons. In some embodiments, R is not an octane. In some embodiments, R is an alkyl group containing 4-7 or 9-18 carbons. In some embodiments, the hydrophobic moiety comprises the following structure:

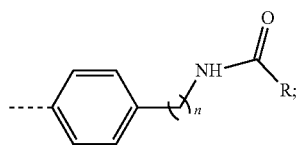

wherein the dotted line indicates a connection (e.g. a covalent connection) to the end of the sense or antisense strand, n is 1-3, and R is an alkyl group containing 4-18 carbons. In some embodiments, the hydrophobic moiety comprises the following structure:

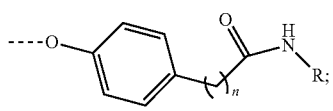

wherein the dotted line indicates a connection (e.g. a covalent connection) to the end of the sense or antisense strand, n is 1-3, and R is an alkyl group containing 4-18 carbons. In some embodiments, the hydrophobic moiety comprises the following structure:

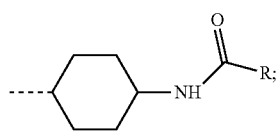

wherein the dotted line indicates a connection (e.g. a covalent connection) to the end of the sense or antisense strand and R is an alkyl group containing 4-18 carbons. In some embodiments, the hydrophobic moiety comprises a lipid moiety depicted in Table 1. The sense strand may include a 2-deoxy modification at position 9.

In some embodiments, the sense strand and the antisense strand form a duplex. In some embodiments, the duplex comprises at least 10 base pairs, at least 11 base pairs, at least 12 base pairs, at least 13 base pairs, at least 14 base pairs, at least 15 base pairs, at least 16 base pairs, at least 17 base pairs, at least 18 base pairs, at least 19 base pairs, at least 20 base pairs, at least 21 base pairs, at least 22 base pairs, at least 23 base pairs, at least 24 base pairs, or at least 25 base pairs. In some embodiments, the duplex comprises 19 base pairs. In some embodiments, the duplex comprises a sense strand overhang. In some embodiments, the sense strand overhang comprises 1-4 nucleotides. In some embodiments, the sense strand overhang comprises 2 nucleotides. In some embodiments, the sense strand overhang comprises uracil. In some embodiments, the duplex comprises an antisense strand overhang. In some embodiments, the antisense strand overhang comprises 1-4 nucleotides. In some embodiments, the antisense strand overhang comprises 2 nucleotides. In some embodiments, the antisense strand overhang comprises uracil. In some embodiments, the sense strand and the antisense strand form a duplex comprising a sense strand 3' overhang of 1-3 nucleotides and an antisense strand 3' overhang of 1-3 nucleotides. In some embodiments, the sense strand and the antisense strand form a duplex comprising a sense strand 3' overhang of 2 uracil nucleotides and an antisense strand 3' overhang of 2 uracil nucleotides. Some embodiments include a pharmaceutically acceptable carrier. Described herein, in some embodiments, are methods of treatment, comprising administering to a subject in need thereof an effective amount of the composition. Described herein, in some embodiments, are methods of reducing an amount of an RNA or protein in a cell, comprising administering the composition to the cell. In some embodiments, administering the composition the cell comprises administering the composition to a subject comprising the cell.

Described herein, in some embodiments, are methods of treatment, comprising administering to a subject in need thereof an effective amount of a composition or siRNA described herein. In some embodiments, the administration comprises subcutaneous, intravitreal, intrathecal, or intracerebroventricular administration. In some embodiments, the siRNA targets an mRNA encoding a protein that mediates a disease of the subject. In some embodiments, the mRNA is in a tissue of the subject, the tissue comprising an eye, liver, fat, brain, or spinal cord.

Described herein, in some embodiments, are methods of reducing an amount of a target RNA or protein encoded by the RNA in a cell, comprising administering a composition or siRNA described herein to the cell, wherein the antisense strand comprises a sequence that is complementary to and binds to the RNA. In some embodiments, administering the composition the cell comprises administering the composition to a subject comprising the cell. In some embodiments, the administration comprises subcutaneous, intravitreal, intrathecal, or intracerebroventricular administration. In some embodiments, the administration reduces a measurement of the target RNA or protein encoded by the RNA, by at least 10% relative to a baseline measurement or control. In some embodiments, the cell comprises an eye, liver, fat, brain, or spinal cord cell.

DETAILED DESCRIPTION OF THE INVENTION

Disclosed herein, in some embodiments, are modified oligonucleotides. The modified oligonucleotide may be an siRNA that includes modifications to the ribose rings, and phosphate linkages. The modifications may be in particular patterns that maximize cell delivery, stability, and efficiency. The siRNA may also include a vinyl phosphonate and a hydrophobic group. These modifications may aid in delivery to a cell or tissue within a subject. The modified oligonucleotide may be used in a method such as a treatment method or a method of reducing gene expression.

In some embodiments, the oligonucleotide comprises a duplex consisting of 21 nucleotide single strands with base pairing between 19 of the base pairs. In some embodiments, the duplex comprises single-stranded 2 nucleotide overhangs are at the 3' ends of each strand. One strand (antisense strand) is complementary to target mRNA. Each end of the antisense strand has one to two phosphorothioate bonds. The 5' end has an optional phosphate mimic such as a vinyl phosphonate. In some embodiments, the oligonucleotide is used to knock down a target mRNA or a target protein. In some embodiments, the sense strand has the same sequence as the target mRNA. In some embodiments, there are 1-2 phosphorothioates at the 3' end. In some embodiments, there are 1 or no phosphorothioates at the 5' end. In some embodiments, there is a hydrophobic conjugate of 12 to 25 carbons attached at the 5' end via a phosphodiester bond.

I. COMPOSITIONS

Disclosed herein, in some embodiments, are compositions comprising an oligonucleotide. In some embodiments, the composition comprises an oligonucleotide that targets a target oligonucleotide. The target oligonucleotide may include a target RNA. In some embodiments, the composition consists of an oligonucleotide that targets the target RNA. The target RNA may include a target mRNA. In some embodiments, the oligonucleotide reduces a target mRNA expression in the subject. In some embodiments, the oligonucleotide reduces target protein expression in the subject. The oligonucleotide may include an RNA duplex. The oligonucleotide may include a small interfering RNA (siRNA). The oligonucleotide may include an antisense oligonucleotide (ASO). In some embodiments, a composition is used in a method of treating a disorder in a subject in need thereof. Some embodiments relate to a composition comprising an oligonucleotide for use in a method of treating a disorder. Some embodiments relate to use of a composition comprising an oligonucleotide, in a method of treating a disorder.

Targets may be identified by a variety of ways. In some instances, a target oligonucleotide comprises an mRNA that has expression levels that are associated with incidence of a disorder (e.g. an adipose-related or eye-related disorder). In some instances, the target oligonucleotide comprises an mRNA that is encoded by a gene that has a particular genotype associated with the disorder. Large-scale human genetic data can improve the success rate of pharmaceutical discovery and development. A Genome Wide Association Study (GWAS) may detect associations between genetic variants and traits in a population sample. A GWAS may enable better understanding of the biology of disease, and provide applicable treatments. A GWAS can utilize genotyping and/or sequencing data, and often involves an evaluation of millions of genetic variants that are relatively evenly distributed across the genome. The most common GWAS design is the case-control study, which involves comparing variant frequencies in cases versus controls. If a variant has a significantly different frequency in cases versus controls, that variant is said to be associated with disease. Association statistics that may be used in a GWAS are p-values, as a measure of statistical significance; odds ratios (OR), as a measure of effect size; or beta coefficients (beta), as a measure of effect size. Researchers often assume an additive genetic model and calculate an allelic odds ratio, which is the increased (or decreased) risk of disease conferred by each additional copy of an allele (compared to carrying no copies of that allele). An additional concept in design and interpretation of GWAS is that of linkage disequilibrium, which is the non-random association of alleles. The presence of linkage disequilibrium can obfuscate which variant is "causal."

Functional annotation of variants and/or wet lab experimentation is used to identify a causal genetic variant identified via GWAS, and in many cases leads to identification of disease-causing genes. In particular, understanding the functional effect of a causal genetic variant (for example, loss of protein function, gain of protein function, increase in gene expression, or decrease in gene expression) allows that variant to be used as a proxy for therapeutic modulation of the target gene, or to gain insight into potential therapeutic efficacy and safety of a therapeutic that modulates that target.

Identification of such gene-disease associations has provided insights into disease biology and is used to identify novel therapeutic targets for the pharmaceutical industry. In order to translate the therapeutic insights derived from human genetics, disease biology in patients are exogenously 'programmed' into replicating the observation from human genetics. There are several options for therapeutic modalities that may be brought to bear in translating therapeutic targets identified via human genetics into novel medicines. These include well established therapeutic modalities such as small molecules and monoclonal antibodies, maturing modalities such as oligonucleotides, and emerging modalities such as gene therapy and gene editing. The choice of therapeutic modality depends on factors such as the location of a target (for example, intracellular, extracellular, or secreted), a relevant tissue (for example, lung or eye) and a relevant indication. Such studies may be conducted to identify specific disorder-related targets for siRNA inhibition by a composition or compound described herein. In some cases, the target may be related to a particular tissue.

Disclosed herein are compositions comprising an oligonucleotide that targets the target RNA. Where inhibition or targeting of target RNA is disclosed, it is contemplated that some embodiments may include inhibiting or targeting a target protein or target RNA. For example, by inhibiting or targeting an RNA (e.g. mRNA) encoded by the target gene using an oligonucleotide described herein, the target protein may be inhibited or targeted as a result of there being less production of the target protein by translation of the target RNA; or a target protein may be targeted or inhibited by an oligonucleotide that binds or interacts with a target RNA and reduces production of the target protein from the target RNA. Thus, targeting may refer to binding a target RNA and reducing target RNA or protein levels. The oligonucleotide may include a small interfering RNA (siRNA) or an antisense oligonucleotide (ASO). Also provided herein are methods of treating target disorder by providing an oligonucleotide that targets target to a subject in need thereof.

Some embodiments include a composition comprising an oligonucleotide that targets an mRNA and when administered to a subject in an effective amount decreases target mRNA or protein levels in a cell, fluid or tissue. In some embodiments, the composition comprises an oligonucleotide that targets the target RNA and when administered to a subject in an effective amount decreases target mRNA levels in a cell or tissue. In some embodiments, the target mRNA levels are decreased by about 2.5% or more, about 5% or more, or about 7.5% or more, as compared to prior to administration. In some embodiments, the target mRNA levels are decreased by about 10% or more, as compared to prior to administration. In some embodiments, the target mRNA levels are decreased by about 20% or more, about 30% or more, about 40% or more, about 50% or more, about 60% or more, about 70% or more, about 80% or more, about 90% or more, or about 100%, as compared to prior to administration. In some embodiments, the target mRNA levels are decreased by no more than about 2.5%, no more than about 5%, or no more than about 7.5%, as compared to prior to administration. In some embodiments, the target mRNA levels are decreased by no more than about 10%, as compared to prior to administration. In some embodiments, the target mRNA levels are decreased by no more than about 20%, no more than about 30%, no more than about 40%, no more than about 50%, no more than about 60%, no more than about 70%, no more than about 80%, or no more than about 90%, as compared to prior to administration. In some embodiments, the target mRNA levels are decreased by 2.5%, 5%, 7.5%, 10%, 15%, 20%, 25%, 30%, 35%, 40%, 45%, 50%, 55%, 60%, 65%, 70%, 75%, 80%, 85%, 90%, 95%, or 100%, or by a range defined by any of the two aforementioned percentages.

In some embodiments, the composition comprises an oligonucleotide that targets the target mRNA and when administered to a subject in an effective amount decreases target protein levels in a cell, fluid or tissue. In some embodiments, the target protein levels are decreased by about 2.5% or more, about 5% or more, or about 7.5% or more, as compared to prior to administration. In some embodiments, the target protein levels are decreased by about 10% or more, as compared to prior to administration. In some embodiments, the target protein levels are decreased by about 20% or more, about 30% or more, about 40% or more, about 50% or more, about 60% or more, about 70% or more, about 80% or more, about 90% or more, or about 100%, as compared to prior to administration. In some embodiments, the target protein levels are decreased by no more than about 2.5%, no more than about 5%, or no more than about 7.5%, as compared to prior to administration. In some embodiments, the target protein levels are decreased by no more than about 10%, as compared to prior to administration. In some embodiments, the target protein levels are decreased by no more than about 20%, no more than about 30%, no more than about 40%, no more than about 50%, no more than about 60%, no more than about 70%, no more than about 80%, or no more than about 90%, as compared to prior to administration. In some embodiments, the target protein levels are decreased by 2.5%, 5%, 7.5%, 10%, 15%, 20%, 25%, 30%, 35%, 40%, 45%, 50%, 55%, 60%, 65%, 70%, 75%, 80%, 85%, 90%, 95%, or 100%, or by a range defined by any of the two aforementioned percentages.

In some embodiments, the composition comprises an oligonucleotide that targets an mRNA and when administered to a subject in an effective amount diminishes a disease phenotype. In some embodiments, the disease phenotype is decreased by about 2.5% or more, about 5% or more, or about 7.5% or more, as compared to prior to administration. In some embodiments, the disease phenotype is decreased by about 10% or more, as compared to prior to administration. In some embodiments, the disease phenotype is decreased by about 20% or more, about 30% or more, about 40% or more, about 50% or more, about 60% or more, about 70% or more, about 80% or more, about 90% or more, or about 100%, as compared to prior to administration. In some embodiments, the disease phenotype is decreased by no more than about 2.5%, no more than about 5%, or no more than about 7.5%, as compared to prior to administration. In some embodiments, the disease phenotype is decreased by no more than about 10%, as compared to prior to administration. In some embodiments, the disease phenotype is decreased by no more than about 20%, no more than about 30%, no more than about 40%, no more than about 50%, no more than about 60%, no more than about 70%, no more than about 80%, or no more than about 90%, as compared to prior to administration. In some embodiments, the disease phenotype is decreased by 2.5%, 5%, 7.5%, 10%, 15%, 20%, 25%, 30%, 35%, 40%, 45%, 50%, 55%, 60%, 65%, 70%, 75%, 80%, 85%, 90%, 95%, or 100%, or by a range defined by any of the two aforementioned percentages.

In some embodiments, the composition comprises an oligonucleotide that targets an mRNA and when administered to a subject in an effective amount enhances a protective phenotype against a disease in the subject. In some embodiments, the protective phenotype is increased by about 2.5% or more, about 5% or more, or about 7.5% or more, as compared to prior to administration. In some embodiments, the protective phenotype is increased by about 10% or more, as compared to prior to administration. In some embodiments, the protective phenotype is increased by about 20% or more, about 30% or more, about 40% or more, about 50% or more, about 60% or more, about 70% or more, about 80% or more, about 90% or more, or about 100% or more, as compared to prior to administration. In some embodiments, the protective phenotype is increased by about 200% or more, about 300% or more, about 400% or more, about 500% or more, about 600% or more, about 700% or more, about 800% or more, about 900% or more, or about 1000% or more, as compared to prior to administration. In some embodiments, the protective phenotype is increased by no more than about 2.5%, no more than about 5%, or no more than about 7.5%, as compared to prior to administration. In some embodiments, the protective phenotype is increased by no more than about 10%, as compared to prior to administration. In some embodiments, the protective phenotype is increased by no more than about 20%, no more than about 30%, no more than about 40%, no more than about 50%, no more than about 60%, no more than about 70%, no more than about 80%, no more than about 90%, or no more than about 100%, as compared to prior to administration. In some embodiments, the protective phenotype is increased by no more than about 200%, no more than about 300%, no more than about 400%, no more than about 500%, no more than about 600%, no more than about 700%, no more than about 800%, no more than about 900%, or no more than about 1000%, as compared to prior to administration. In some embodiments, the protective phenotype is increased by 2.5%, 5%, 7.5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 400%, 500%, 600%, 700%, 800%, 900%, or 1000%, or by a range defined by any of the two aforementioned percentages.

A. siRNAs

In some embodiments, the composition comprises an oligonucleotide that targets a target RNA such as mRNA, wherein the oligonucleotide comprises a small interfering RNA (siRNA). In some embodiments, the composition comprises an oligonucleotide that targets the target mRNA, wherein the oligonucleotide comprises a small interfering RNA (siRNA) comprising a sense strand and an antisense strand.

In some embodiments, the composition comprises an oligonucleotide that inhibits the expression of the target mRNA, wherein the oligonucleotide comprises an siRNA comprising a sense strand and an antisense strand, wherein the sense strand is 12-30 nucleosides in length. In some embodiments, the composition comprises a sense strand that is 10, 11, 12, 13, 14, 15, 16, 17, 18, 19, 20, 21, 22, 23, 24, 25, 26, 27, 28, 29, or 30 nucleosides in length, or a range defined by any of the two aforementioned numbers. The sense strand may be 14-30 nucleosides in length. In some embodiments, the composition comprises an antisense strand is 12-30 nucleosides in length. In some embodiments, the composition comprises an antisense strand that is 10, 11, 12, 13, 14, 15, 16, 17, 18, 19, 20, 21, 22, 23, 24, 25, 26, 27, 28, 29, or 30 nucleosides in length, or a range defined by any of the two aforementioned numbers. The antisense strand may be 14-30 nucleosides in length.

In some embodiments, the composition comprises an oligonucleotide that inhibits the expression of the target mRNA, wherein the oligonucleotide comprises an siRNA comprising a sense strand and an antisense strand, each strand is independently about 12-30 nucleosides in length, and at least one of the sense strand and the antisense strand comprises a nucleoside sequence comprising about 12-30 contiguous nucleosides of a full-length human target mRNA sequence. In some embodiments, at least one of the sense strand and the antisense strand comprise a nucleoside sequence comprising at least about 10, 11, 12, 13, 14, 15, 16, 17, 18, 19, 20, 21, 22, 23, 24, 25, 26, 27, 28, 29, 30, or more contiguous nucleosides of the target RNA.

In some embodiments, the composition comprises an oligonucleotide that inhibits the expression of a target mRNA, wherein the oligonucleotide comprises an siRNA comprising a sense strand and an antisense strand, wherein the sense strand and the antisense strand form a double-stranded RNA duplex. In some embodiments, the first base pair of the double-stranded RNA duplex is an AU base pair.

In some embodiments, the sense strand further comprises a 3' overhang. In some embodiments, the 3' overhang comprises 1, 2, 3, 4, 5, 6, 7, 8, 9, or 10 nucleosides, or a range of nucleotides defined by any two of the aforementioned numbers. In some embodiments, the 3' overhang comprises 1, 2, or more nucleosides. In some embodiments, the 3' overhang comprises 2 nucleosides. In some embodiments, the sense strand further comprises a 5' overhang. In some embodiments, the 5' overhang comprises 1, 2, 3, 4, 5, 6, 7, 8, 9, or 10 nucleosides, or a range of nucleotides defined by any two of the aforementioned numbers. In some embodiments, the 5' overhang comprises 1, 2, or more nucleosides. In some embodiments, the 5' overhang comprises 2 nucleosides.

In some embodiments, the antisense strand further comprises a 3' overhang. In some embodiments, the 3' overhang comprises 1, 2, 3, 4, 5, 6, 7, 8, 9, or 10 nucleosides, or a range of nucleotides defined by any two of the aforementioned numbers. In some embodiments, the 3' overhang comprises 1, 2, or more nucleosides. In some embodiments, the 3' overhang comprises 2 nucleosides. In some embodiments, the antisense strand further comprises a 5' overhang. In some embodiments, the 5' overhang comprises 1, 2, 3, 4, 5, 6, 7, 8, 9, or 10 nucleosides, or a range of nucleotides defined by any two of the aforementioned numbers. In some embodiments, the 5' overhang comprises 1, 2, or more nucleosides. In some embodiments, the 5' overhang comprises 2 nucleosides.

In some embodiments, the composition comprises an oligonucleotide that inhibits the expression of a target mRNA, wherein the oligonucleotide comprises an siRNA comprising a sense strand and an antisense strand, wherein the siRNA binds with a 19 mer in a human target mRNA. In some embodiments, the siRNA binds with a 12 mer, a 13 mer, a 14 mer, a 15 mer, a 16 mer, a 17 mer, a 18 mer, a 19 mer, a 20 mer, a 21 mer, a 22 mer, a 23 mer, a 24 mer, or a 25 mer in a human target mRNA.

In some embodiments, the composition comprises an oligonucleotide that inhibits the expression of a target mRNA, wherein the oligonucleotide comprises an siRNA comprising a sense strand and an antisense strand, wherein the siRNA binds with a 17 mer in a non-human primate target mRNA. In some embodiments, the siRNA binds with a 12 mer, a 13 mer, a 14 mer, a 15 mer, a 16 mer, a 17 mer, a 18 mer, a 19 mer, a 20 mer, a 21 mer, a 22 mer, a 23 mer, a 24 mer, or a 25 mer in a non-human primate target mRNA.

In some embodiments, the composition comprises an oligonucleotide that inhibits the expression of a target mRNA, wherein the oligonucleotide comprises an siRNA comprising a sense strand and an antisense strand, wherein the siRNA binds with a human target mRNA and less than or equal to 20 human off-targets, with no more than 2 mismatches in the antisense strand. In some embodiments, the siRNA binds with a human target mRNA and less than or equal to 10 human off-targets, with no more than 2 mismatches in the antisense strand. In some embodiments, the siRNA binds with a human target mRNA and less than or equal to 30 human off-targets, with no more than 2 mismatches in the antisense strand. In some embodiments, the siRNA binds with a human target mRNA and less than or equal to 40 human off-targets, with no more than 2 mismatches in the antisense strand. In some embodiments, the siRNA binds with a human target mRNA and less than or equal to 50 human off-targets, with no more than 2 mismatches in the antisense strand. In some embodiments, the siRNA binds with a human target mRNA and less than or equal to 10 human off-targets, with no more than 3 mismatches in the antisense strand. In some embodiments, the siRNA binds with a human target mRNA and less than or equal to 20 human off-targets, with no more than 3 mismatches in the antisense strand. In some embodiments, the siRNA binds with a human target mRNA and less than or equal to 30 human off-targets, with no more than 3 mismatches in the antisense strand. In some embodiments, the siRNA binds with a human target mRNA and less than or equal to 40 human off-targets, with no more than 3 mismatches in the antisense strand. In some embodiments, the siRNA binds with a human target mRNA and less than or equal to 50 human off-targets, with no more than 3 mismatches in the antisense strand.

In some embodiments, the composition comprises an oligonucleotide that inhibits the expression of a target mRNA, wherein the oligonucleotide comprises an siRNA comprising a sense strand and an antisense strand, siRNA binds with a human target mRNA target site that does not harbor an SNP, with a minor allele frequency (MAF) greater or equal to 1% (pos. 2-18). In some embodiments, the MAF is greater or equal to about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

B. ASOs

In some embodiments, the composition comprises an oligonucleotide that inhibits the expression of a target mRNA, wherein the oligonucleotide comprises an antisense oligonucleotide (ASO). In some embodiments, the ASO is 12-30 nucleosides in length. In some embodiments, the ASO is 14-30 nucleosides in length. In some embodiments, the ASO is at least about 10, 11, 12, 13, 14, 15, 16, 17, 18, 19, 20, 21, 22, 23, 24, 25, 26, 27, 28, 29, or 30 nucleosides in length, or a range defined by any of the two aforementioned numbers. In some embodiments, the ASO is 15-25 nucleosides in length. In some embodiments, the ASO is 20 nucleosides in length.

In some embodiments, the composition comprises an oligonucleotide that inhibits the expression of a target mRNA, wherein the oligonucleotide comprises an ASO about 12-30 nucleosides in length and comprising a nucleoside sequence complementary to about 12-30 contiguous nucleosides of a full-length human target mRNA sequence; wherein (i) the oligonucleotide comprises a modification comprising a modified nucleoside and/or a modified internucleoside linkage, and/or (ii) the composition comprises a pharmaceutically acceptable carrier. In some embodiments, the ASO comprise a nucleoside sequence complementary to at least about 10, 11, 12, 13, 14, 15, 16, 17, 18, 19, 20, 21, 22, 23, 24, 25, 26, 27, 28, 29, 30, or more contiguous nucleosides of a target mRNA.

C. Modifications

In some embodiments, the composition comprises an oligonucleotide that inhibits the expression of a target mRNA, wherein the oligonucleotide comprises a modification comprising a modified nucleoside and/or a modified internucleoside linkage, and/or (ii) the composition comprises a pharmaceutically acceptable carrier. In some embodiments, the oligonucleotide comprises a modification comprising a modified nucleoside and/or a modified internucleoside linkage. In some embodiments, the oligonucleotide comprises a modified internucleoside linkage. In some embodiments, the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof. In some embodiments, the modified internucleoside linkage comprises one or more phosphorothioate linkages. A phosphorothioate may include a nonbridging oxygen atom in a phosphate backbone of the oligonucleotide that is replaced by sulfur. Modified internucleoside linkages may be included in siRNAs or ASOs. Benefits of the modified internucleoside linkage may include decreased toxicity or improved pharmacokinetics.

In some embodiments, the composition comprises an oligonucleotide that inhibits the expression of a target mRNA, wherein the oligonucleotide comprises a modified internucleoside linkage, wherein the oligonucleotide comprises 1, 2, 3, 4, 5, 6, 7, 8, 9, 10, 11, 12, 13, 14, 15, 16, 17, 18, 19, or 20 modified internucleoside linkages, or a range of modified internucleoside linkages defined by any two of the aforementioned numbers. In some embodiments, the oligonucleotide comprises no more than 18 modified internucleoside linkages. In some embodiments, the oligonucleotide comprises no more than 20 modified internucleoside linkages. In some embodiments, the oligonucleotide comprises 2 or more modified internucleoside linkages, 3 or more modified internucleoside linkages, 4 or more modified internucleoside linkages, 5 or more modified internucleoside linkages, 6 or more modified internucleoside linkages, 7 or more modified internucleoside linkages, 8 or more modified internucleoside linkages, 9 or more modified internucleoside linkages, 10 or more modified internucleoside linkages, 11 or more modified internucleoside linkages, 12 or more modified internucleoside linkages, 13 or more modified internucleoside linkages, 14 or more modified internucleoside linkages, 15 or more modified internucleoside linkages, 16 or more modified internucleoside linkages, 17 or more modified internucleoside linkages, 18 or more modified internucleoside linkages, 19 or more modified internucleoside linkages, or 20 or more modified internucleoside linkages.

In some embodiments, the composition comprises an oligonucleotide that inhibits the expression of a target mRNA, wherein the oligonucleotide comprises the modified nucleoside. In some embodiments, the modified nucleoside comprises a locked nucleic acid (LNA), hexitol nucleic acid (HLA), cyclohexene nucleic acid (CeNA), 2'-methoxyethyl, 2'-O-alkyl, 2'-O-allyl, 2'-fluoro, or 2'-deoxy, or a combination thereof. In some embodiments, the modified nucleoside comprises a LNA. In some embodiments, the modified nucleoside comprises a 2',4' constrained ethyl nucleic acid. In some embodiments, the modified nucleoside comprises HLA. In some embodiments, the modified nucleoside comprises CeNA. In some embodiments, the modified nucleoside comprises a 2'-methoxyethyl group. In some embodiments, the modified nucleoside comprises a 2'-O-alkyl group. In some embodiments, the modified nucleoside comprises 2'-methoxyethyl. In some embodiments, the modified nucleoside comprises a methoxyethyl. For example, position 4 of the sense strand may comprise a methoxyethyl nucleoside such as a 2'-methoxyethyl thymine. In some embodiments, the modified nucleoside comprises 2'-O-methyl. In some embodiments, the modified nucleoside comprises a 2'-O-allyl group. In some embodiments, the modified nucleoside comprises a 2'-fluoro group. In some embodiments, the modified nucleoside comprises a 2'-deoxy group. In some embodiments, the modified nucleoside comprises a 2'-O-methyl nucleoside, 2'-deoxyfluoro nucleoside, 2'-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside, or 2'-ara-F, or a combination thereof. In some embodiments, the modified nucleoside comprises a 2'-O-methyl nucleoside. In some embodiments, the modified nucleoside comprises a 2'-deoxyfluoro nucleoside. In some embodiments, the modified nucleoside comprises a 2'-O-NMA nucleoside. In some embodiments, the modified nucleoside comprises a 2'-O-DMAEOE nucleoside. In some embodiments, the modified nucleoside comprises a 2'-O-aminopropyl (2'-O-AP) nucleoside. In some embodiments, the modified nucleoside comprises 2'-ara-F. In some embodiments, the modified nucleoside comprises one or more 2'fluoro modified nucleosides. In some embodiments, the modified nucleoside comprises a 2' O-alkyl modified nucleoside. Benefits of the modified nucleoside may include decreased toxicity or improved pharmacokinetics.

In some embodiments, the oligonucleotide comprises 1, 2, 3, 4, 5, 6, 7, 8, 9, 10, 11, 12, 13, 14, 15, 16, 17, 18, 19, 20, or 21 modified nucleosides, or a range of nucleosides defined by any two of the aforementioned numbers. In some embodiments, the oligonucleotide comprises no more than 19 modified nucleosides. In some embodiments, the oligonucleotide comprises no more than 21 modified nucleosides. In some embodiments, the oligonucleotide comprises 2 or more modified nucleosides, 3 or more modified nucleosides, 4 or more modified nucleosides, 5 or more modified nucleosides, 6 or more modified nucleosides, 7 or more modified nucleosides, 8 or more modified nucleosides, 9 or more modified nucleosides, 10 or more modified nucleosides, 11 or more modified nucleosides, 12 or more modified nucleosides, 13 or more modified nucleosides, 14 or more modified nucleosides, 15 or more modified nucleosides, 16 or more modified nucleosides, 17 or more modified nucleosides, 18 or more modified nucleosides, 19 or more modified nucleosides, 20 or more modified nucleosides, or 21 or more modified nucleosides.

In some embodiments, the composition comprises an oligonucleotide that inhibits the expression of a target mRNA, wherein the oligonucleotide comprises a moiety attached at a 3' or 5' terminus of the oligonucleotide. Examples of moieties include a hydrophobic moiety or a sugar moiety, or a combination thereof. In some embodiments, the oligonucleotide is an siRNA having a sense strand, and the moiety is attached to a 5' end of the sense strand. In some embodiments, the oligonucleotide is an siRNA having a sense strand, and the moiety is attached to a 3' end of the sense strand. In some embodiments, the oligonucleotide is an siRNA having an antisense strand, and the moiety is attached to a 5' end of the antisense strand. In some embodiments, the oligonucleotide is an siRNA having an antisense strand, and the moiety is attached to a 3' end of the antisense strand. In some embodiments, the oligonucleotide is an ASO, and the moiety is attached to a 5' end of the ASO. In some embodiments, the oligonucleotide is an ASO, and the moiety is attached to a 3' end of the ASO.

In some embodiments, the composition comprises an oligonucleotide that inhibits the expression of the target mRNA, wherein the oligonucleotide comprises a hydrophobic moiety. An oligonucleotide comprising a hydrophobic moiety may include, or be referred to as a hydrophobic conjugate. Hydrophobic moieties may be useful for enhancing cellular uptake. The hydrophobic moiety may be attached at a 3' or 5' terminus of the oligonucleotide. The hydrophobic moiety may include a lipid such as a fatty acid. The hydrophobic moiety may include a hydrocarbon. The hydrocarbon may be linear. The hydrocarbon may be non-linear. The hydrophobic moiety may include a lipid moiety or a cholesterol moiety, or a combination thereof. In some embodiments, the hydrophobic moiety includes a cyclohexanyl. In some embodiments, the hydrophobic moiety includes a lipid. In some embodiments, the hydrophobic moiety is used in a specific format described herein. In some embodiments, the hydrophobic moiety is attached at a 5' end of a sense strand without any phosphorothioate groups or linkages at the 5' end. The hydrophobic moiety may include an esterified lipid.

The hydrophobic moiety may be or include a lipid moiety. In some embodiments, the composition comprises an oligonucleotide that inhibits the expression of the target mRNA, wherein the oligonucleotide comprises a lipid attached at a 3' or 5' terminus of the oligonucleotide. In some embodiments, the lipid comprises cholesterol, myristyl, palmityl, stearyl, lithocholyl, docosanyl, docosahexaenyl, myristyl, palmityl stearyl, or α-tocopheryl, or a combination thereof. In some embodiments, the lipid comprises stearol, t-butylphenol, n-butylphenol, octylphenyl, dodecylphenyl, phenyl n-dodecyl, octadecylbenzamide, hexadecylbenzamide, or octadecylcyclohexyl. In some embodiments, the lipid comprises phenyl para C12. The lipid moiety may be esterified.

In some embodiments, the oligonucleotide comprises any aspect of the following structure:

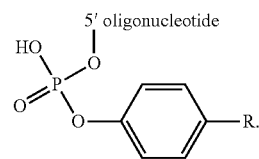

In some embodiments, R is not octane. In some embodiments, R is not an octane. In some embodiments, R is an alkyl group containing 4-7 or 9-18 carbons. In some embodiments, the oligonucleotide comprises any aspect of the following structure:

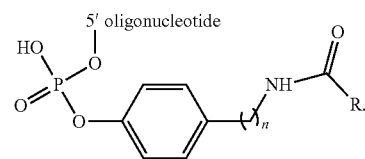

In some embodiments, the oligonucleotide comprises any aspect of the following structure:

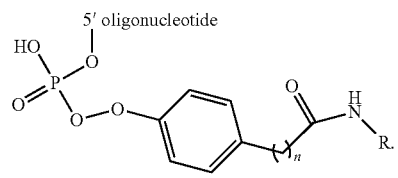

In some embodiments, the oligonucleotide comprises any aspect of the following structure:

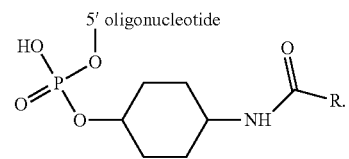

The aspect included in the oligonucleotide may include the entire structure, or may include the lipid moiety, of any of the structures shown. In some embodiments, n is 1-3. In some embodiments, n is 1. In some embodiments, n is 2. In some embodiments, n is 3. In some embodiments, R is an alkyl group. In some embodiments, the alkyl group contains 1, 2, 3, 4, 5, 6, 7, 8, 9, 10, 11, 12, 13, 14, 15, 16, 17, 18, 19, or 20 carbons. In some embodiments, the alkyl group contains 4, 5, 6, 7, 8, 9, 10, 11, 12, 13, 14, 15, 16, 17, or 18 carbons, or a range defined by any two of the aforementioned numbers of carbons. In some embodiments, the alkyl group contains 4-18 carbons. In some embodiments, R is not an octane (C8). In some embodiments, R is $C_{4-7}$ alkyl. In some embodiments, R is $C_{9-18}$ alkyl. In some embodiments, R is $C_{4-7}$ alkyl and $C_{9-18}$ alkyl. In some embodiments, the alkyl group contains 11 carbons. In some embodiments, the alkyl group contains 12 carbons. In some embodiments, the alkyl group contains 13 carbons. In some embodiments, the alkyl group contains 14 carbons. In some embodiments, the alkyl group contains 15 carbons. In some embodiments, the alkyl group contains 16 carbons. In some embodiments, the alkyl group contains 17 carbons. In some embodiments, the alkyl group contains 18 carbons. In some embodiments, R is not an octane ($C_8$). In some embodiments, R includes a branched carbon chain. In some embodiments, R includes an unbranched carbon chain. In some embodiments, the lipid moiety comprises an alcohol or ether. In some embodiments, the lipid moiety has at least one degree of unsaturation. In some embodiments, the lipid moiety is an omega fatty acid, such as an omega-3, omega-5, omega-6, omega-7, or omega-9 fatty acid.

In some embodiments, the lipid includes a fatty acid. In some embodiments, the lipid comprises a lipid depicted in Table 1. The example lipid moieties in Table 1 are shown attached at a 5' end of an oligonucleotide, in which the 5' terminal phosphate of the oligonucleotide is shown with the lipid moiety. In some embodiments, a lipid moiety in Table 1 may be attached at a different point of attachment than shown. For example, the point of attachment of any of the lipid moieties in the table may be at a 3' oligonucleotide end. In some embodiments, the lipid is used for targeting the oligonucleotide to a non-hepatic cell or tissue.

TABLE 1

Lipid moiety examples

| Description | Name | Example depiction attached to an oligonucleotide |
|---|---|---|
| stearyl | ETL3 | |
| t-butylphenyl | ETL7 | |
| n-butylphenyl | ETL8 | |
| octylphenyl | ETL9 | |
| dodecylphenyl | ETL10 | |
| phenyl n-dodecyl | ETL12 | |

TABLE 1-continued

Lipid moiety examples

| Description | Name | Example depiction attached to an oligonucleotide |
|---|---|---|
| octadecylbenzamido | ETL13 | 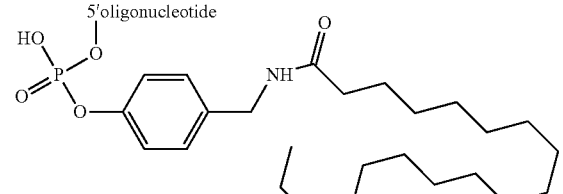 |
| hexadecylbenz-amido | ETL15 | 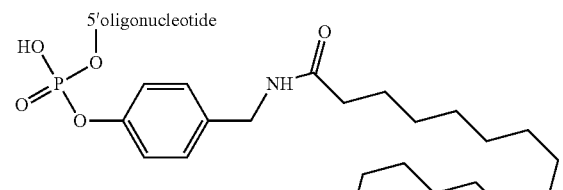 |
| octadecyl-cyclohexyl | ETL16 | 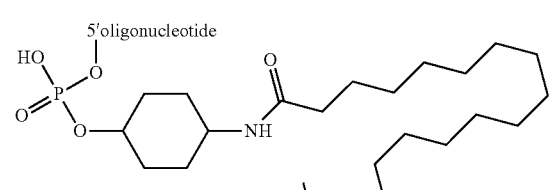 |
| myristamido methylphenyl | ETL18 | 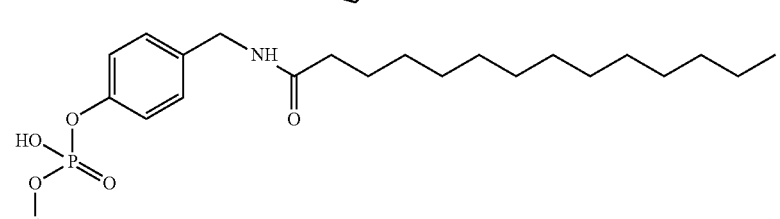 |
| lauramido methylphenyl | ETL19 | 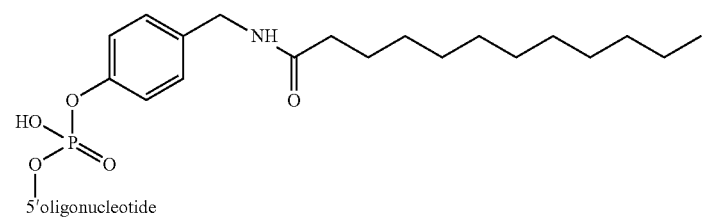 |
| phenethyl-palmityl | ETL20 | 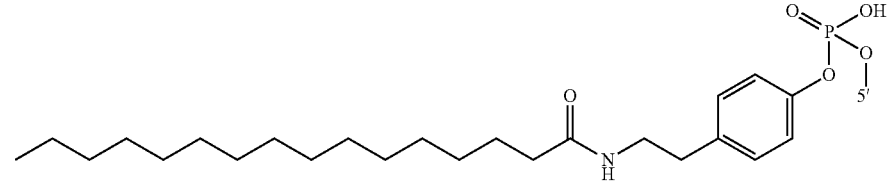 |

In some embodiments, the lipid or lipid moiety includes 16 to 18 carbons. In some embodiments, the lipid includes 16 carbons. In some embodiments, the lipid includes 17 carbons. In some embodiments, the lipid includes 18 carbons. In some embodiments, the lipid moiety includes 16 carbons. In some embodiments, the lipid moiety includes 17 carbons. In some embodiments, the lipid moiety includes 18 carbons. In some embodiments, the lipid moiety includes 19 carbons. In some embodiments, the lipid moiety includes 20 carbons.

The hydrophobic moiety may include a linker that comprises a carbocycle. The carbocycle may be six-membered. Some examples of a carbocycle include phenyl or cyclohexyl. The linker may include a phenyl. The linker may include a cyclohexyl. The lipid may be attached to the carbocycle, which may in turn be attached at a phosphate (e.g. 5' or 3' phosphate) of the oligonucleotide. In some embodiments, the lipid or hydrocarbon, and the end of the sense are connected to the phenyl or cyclohexyl linker in the 1,4; 1,3; or 1,2 substitution pattern (e.g. the para, meta, or ortho phenyl configuration). In some embodiments, the lipid or hydrocarbon, and the end of the sense are connected to the phenyl or cyclohexyl linker in the 1,4 substitution pattern (e.g. the para phenyl configuration). The lipid may be attached to the carbocycle in the ortho orientation relative to the oligonucleotide. The lipid may be attached to the carbocycle in the para orientation relative to the oligonucleotide. The lipid may be attached to the carbocycle in the meta orientation relative to the oligonucleotide. The lipid may be attached to the carbocycle in the in the 1,4 orientation relative to the oligonucleotide. The lipid may be attached to the carbocycle in the in the 1,3 orientation relative to the oligonucleotide. The lipid may be attached to the carbocycle in the in the 1,2 orientation relative to the oligonucleotide.

The lipid moiety may comprise or consist of the following structure

In some embodiments, the lipid moiety comprises or consists of the following structure:

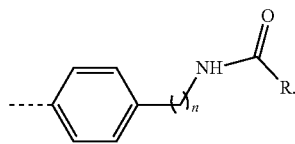

In some embodiments, the lipid moiety comprises or consists of the following structure:

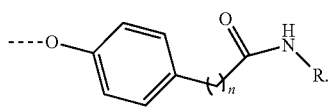

In some embodiments, the lipid moiety comprises or consist of the following structure:

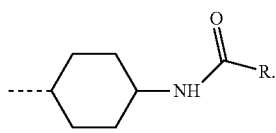

In some embodiments, the dotted line indicates a covalent connection. The covalent connection may between an end of the sense or antisense strand. For example, the connection may be to the 5' end of the sense strand. In some embodiments, n is 0-3. In some embodiments, n is 1-3. In some embodiments, n is 0. In some embodiments, n is 1. In some embodiments, n is 2. In some embodiments, n is 3. In some embodiments, n is 4. In some embodiments, n is 5. In some embodiments, n is 1, 2, 3, 4, 5, 6, 7, 8, 9, or 10. In some embodiments, R includes a branched carbon chain. In some embodiments, R includes an unbranched carbon chain. In some embodiments, R is an alkyl group. In some embodiments, the alkyl group contains 1, 2, 3, 4, 5, 6, 7, 8, 9, 10, 11, 12, 13, 14, 15, 16, 17, 18, 19, or 20 carbons. In some embodiments, the alkyl group contains 4, 5, 6, 7, 8, 9, 10, 11, 12, 13, 14, 15, 16, 17, or 18 carbons, or a range defined by any two of the aforementioned numbers of carbons. In some embodiments, the alkyl group contains 11 carbons. In some embodiments, the alkyl group contains 12 carbons. In some embodiments, the alkyl group contains 13 carbons. In some embodiments, the alkyl group contains 14 carbons. In some embodiments, the alkyl group contains 15 carbons. In some embodiments, the alkyl group contains 16 carbons. In some embodiments, the alkyl group contains 17 carbons. In some embodiments, the alkyl group contains 18 carbons. In some embodiments, R comprises or consists of an alkyl group containing 4-18 carbons. In some embodiments, the lipid moiety is not a phenyloctyl group. In some embodiments, R is not octane. In some embodiments, R is $C_{4-7}$ alkyl. In some embodiments, R is $C_{9-18}$ alkyl. In some embodiments, R is $C_{4-7}$ alkyl and $C_{9-18}$ alkyl. In some embodiments, the lipid moiety is not a phenyloctyl group.

In some embodiments, the 5' hydrophobic moiety comprises any one of the following structures:

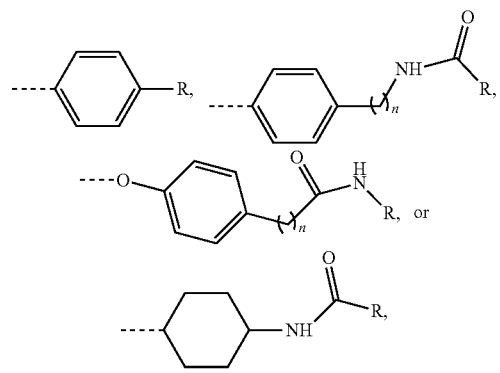

wherein the dotted line indicates a covalent connection to the end of the 5' end of the sense strand, n is 1-3, and R is an alkyl group containing 4-18 carbons. In some embodiments, R is not an octane. In some embodiments, the alkyl group contains 4-7 or 9-18 carbons. In some embodiments, the alkyl group contains 14 carbons. In some embodiments, the alkyl group contains 15 carbons. In some embodiments, the alkyl group contains 16 carbons. In some embodiments, the alkyl group contains 17 carbons. In some embodiments, the alkyl group contains 18 carbons. In some embodiments, the 5' hydrophobic moiety comprises a hydrophobic moiety in Table 1. In some embodiments, the 5' hydrophobic moiety comprises phenyl para C12. In some embodiments, n is 1, 2, 3, 4, 5, 6, 7, 8, 9, 10, 11, 12, 13, or 14. In some embodiments, n is 0-3. In some embodiments, n is 1-3. In some embodiments, n is 1. In some embodiments n is 2. In some embodiments, the hydrophobic moiety comprises an alcohol or an ether. In some embodiments, R is an unsaturated alkyl group. In some embodiments, the unsaturated alkyl group may be monounsaturated. In some embodiments, the unsaturated alkyl group may be unsaturated at the omega-3, position, omega-4 position, omega-5 position, omega-6 position, omega-7 position, omega-8 position, omega-9 position, or a combination thereof. In some embodiments, the 5' hydrophobic moiety is not a phenyloctyl group.

The hydrophobic moiety may include a linker that comprises a carbocycle. The carbocycle may be six-membered. Some examples of a carbocycle include phenyl or cyclohexyl. The linker may include a phenyl. The linker may include a cyclohexyl. The lipid may be attached to the carbocycle, which may in turn be attached at a phosphate (e.g. 5' or 3' phosphate) of the oligonucleotide. In some embodiments, the lipid or hydrocarbon, and the end of the sense are connected to the phenyl or cyclohexyl linker in the 1,4; 1,3; or 1,2 substitution pattern (e.g. the para, meta, or ortho phenyl configuration). In some embodiments, the lipid or hydrocarbon, and the end of the sense are connected to the phenyl or cyclohexyl linker in the 1,4 substitution pattern (e.g. the para phenyl configuration). The lipid may be attached to the carbocycle in the ortho orientation relative to the oligonucleotide. The lipid may be attached to the carbocycle in the para orientation relative to the oligonucleotide. The lipid may be attached to the carbocycle in the meta orientation relative to the oligonucleotide. The lipid may be attached to the carbocycle in the in the 1,4 orientation relative to the oligonucleotide. The lipid may be attached to the carbocycle in the in the 1,3 orientation relative to the oligonucleotide. The lipid may be attached to the carbocycle in the in the 1,2 orientation relative to the oligonucleotide.

The lipid moiety may be attached at a 5' end of the oligonucleotide. The 5' end may have one phosphate linking the lipid moiety to a 5' carbon of a sugar of the oligonucleotide. The 5' end may have two phosphates linking the lipid moiety to a 5' carbon of a sugar of the oligonucleotide. The 5' end may have three phosphates linking the lipid moiety to a 5' carbon of a sugar of the oligonucleotide. The 5' end may have one phosphate connected to the 5' carbon of a sugar of the oligonucleotide, where the one phosphate is connected to the lipid moiety. The 5' end may have two phosphates connected to the 5' carbon of a sugar of the oligonucleotide, where the one of the two phosphates is connected to the lipid moiety. The 5' end may have three phosphates connected to the 5' carbon of a sugar of the oligonucleotide, where the one of the three phosphates is connected to the lipid moiety. The sugar may include a ribose. The sugar may include a deoxyribose. The sugar may be modified a such as a 2' modified sugar (e.g. a 2' O-methyl or 2' fluoro ribose). A phosphate of the 5' end may include a modification such as a sulfur in place of an oxygen. Two phosphates of the 5' end may include a modification such as a sulfur in place of an oxygen. Three phosphates of the 5' end may include a modification such as a sulfur in place of an oxygen. In some embodiments, the oligonucleotide is not d(pT-G-G-G-G-G).

In some embodiments, the oligonucleotide includes 1 lipid moiety. In some embodiments, the oligonucleotide includes 2 lipid moieties. In some embodiments, the oligonucleotide includes 3 lipid moieties. In some embodiments, the oligonucleotide includes 4 lipid moieties.

Some embodiments relate to a method of making an oligonucleotide comprising a hydrophobic conjugate. A strategy for making hydrophobic conjugates may include use of a phosphoramidite reagent based upon a 6-membered ring alcohol such as a phenol or cyclohexanol. The phosphoramidite may be reacted to a nucleotide to connect the nucleotide to the hydrophobic moiety, and thereby produce the hydrophobic conjugate. Some examples of phosphoramidite reagents that may be used to produce a hydrophobic conjugate are provided as follows:

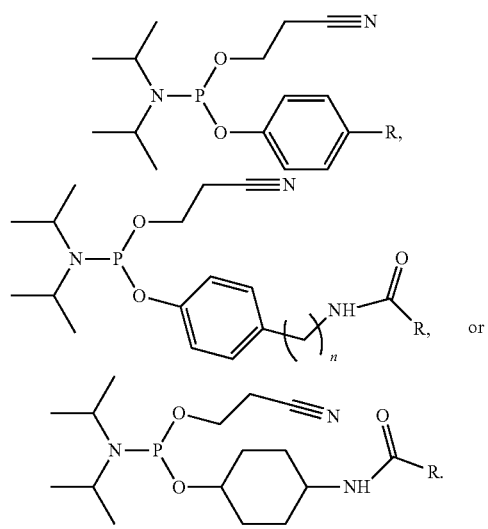

In some embodiments, n is 1-3. In some embodiments, n is 1. In some embodiments, n is 2. In some embodiments, n is 3. In some embodiments, R is an alkyl group. In some embodiments, the alkyl group contains 1, 2, 3, 4, 5, 6, 7, 8, 9, 10, 11, 12, 13, 14, 15, 16, 17, 18, 19, or 20 carbons. In some embodiments, the alkyl group contains 4, 5, 6, 7, 8, 9, 10, 11, 12, 13, 14, 15, 16, 17, or 18 carbons, or a range defined by any two of the aforementioned numbers of carbons. In some embodiments, R comprises or consists of an alkyl group containing 4-18 carbons. Any one of the phosphoramidite reagents may be reacted to a 5' end of an oligonucleotide to produce an oligonucleotide comprising a hydrophobic moiety. In some embodiments, the phosphoramidite reagents is reacted to a 5' end of a sense strand of an siRNA. The sense strand may then be hybridized to an antisense strand to form a duplex. The hybridization may be performed by incubating the sense and antisense strands in solution at a given temperature. The temperature may be gradually reduced. The temperature may comprise or include a temperature comprising an annealing temperature for the sense and antisense strands. The temperature may be below or include a temperature below the annealing temperature for the sense and antisense strands. The temperature may be below a melting temperature of the sense and antisense strands.

In some embodiments, the oligonucleotide includes a negatively charged group. The negatively charged group may aid in cell or tissue penetration. The negatively charged group may be attached at a 5' or 3' end (e.g. a 5' end) of the oligonucleotide. This may be referred to as an end group. The end group may be or include a phosphorothioate, phosphorodithioate, vinylphosphonate, methylphosphonate, cyclopropyl phosphonate, or a deoxy-C-malonyl. The end group may include an extra 5' phosphate such as an extra 5' phosphate. A combination of end groups may be used.

In some embodiments, the oligonucleotide includes a phosphate mimic. In some embodiments, the phosphate mimic comprises vinyl phosphonate. In some embodiments, the vinyl phosphonate comprises a trans-vinylphosphonate. In some embodiments, the vinyl phosphonate comprises a cis-vinylphosphonate. An example of a nucleotide that includes a vinyl phosphonate is shown below.

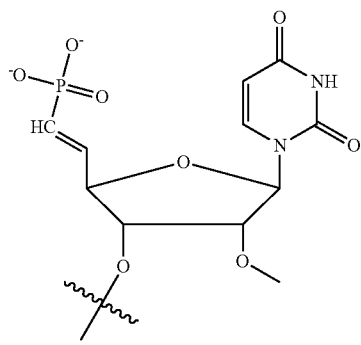

5' vinylphosphonate 2' O Methyl Uridine

In some embodiments, the vinyl phosphonate increases the stability of the oligonucleotide. In some embodiments, the vinyl phosphonate increases the accumulation of the oligonucleotide in tissues. In some embodiments, the vinyl phosphonate protects the oligonucleotide from an exonuclease or a phosphatase. In some embodiments, the vinyl phosphonate improves the binding affinity of the oligonucleotide with the siRNA processing machinery.

In some embodiments, the oligonucleotide includes 1 vinyl phosphonate. In some embodiments, the oligonucleotide includes 2 vinyl phosphonates. In some embodiments, the oligonucleotide includes 3 vinyl phosphonates. In some embodiments, the oligonucleotide includes 4 vinyl phosphonates. In some embodiments, the antisense strand of the oligonucleotide comprises a vinyl phosphonate at the 5' end. In some embodiments, the antisense strand of the oligonucleotide comprises a vinyl phosphonate at the 3' end. In some embodiments, the sense strand of the oligonucleotide comprises a vinyl phosphonate at the 5' end. In some embodiments, the sense strand of the oligonucleotide comprises a vinyl phosphonate at the 3' end.

The oligonucleotide may include purines. Examples of purines include adenine (A) or guanine (G), or modified versions thereof. The oligonucleotide may include pyrimidines. Examples of pyrimidines include cytosine (C), thymine (T), or uracil (U), or modified versions thereof.

In some embodiments, purines of the oligonucleotide comprise 2' fluoro modified purines. In some embodiments, purines of the oligonucleotide comprise 2'-O-methyl modified purines. In some embodiments, purines of the oligonucleotide comprise a mixture of 2' fluoro and 2'-O-methyl modified purines. In some embodiments, all purines of the oligonucleotide comprise 2' fluoro modified purines. In some embodiments, all purines of the oligonucleotide comprise 2'-O-methyl modified purines. In some embodiments, all purines of the oligonucleotide comprise a mixture of 2' fluoro and 2'-O-methyl modified purines. In some embodiments, 2'-O-methyl includes 2' O-methyl.

In some embodiments, pyrimidines of the oligonucleotide comprise 2' fluoro modified pyrimidines. In some embodiments, pyrimidines of the oligonucleotide comprise 2'-O-methyl modified pyrimidines. In some embodiments, pyrimidines of the oligonucleotide comprise a mixture of 2' fluoro and 2'-O-methyl modified pyrimidines. In some embodiments, all pyrimidines of the oligonucleotide comprise 2' fluoro modified pyrimidines. In some embodiments, all pyrimidines of the oligonucleotide comprise 2'-O-methyl modified pyrimidines. In some embodiments, all pyrimidines of the oligonucleotide comprise a mixture of 2' fluoro and 2'-O-methyl modified pyrimidines.

In some embodiments, purines of the oligonucleotide comprise 2' fluoro modified purines, and pyrimidines of the oligonucleotide comprise a mixture of 2' fluoro and 2'-O-methyl modified pyrimidines. In some embodiments, purines of the oligonucleotide comprise 2'-O-methyl modified purines, and pyrimidines of the oligonucleotide comprise a mixture of 2' fluoro and 2'-O-methyl modified pyrimidines. In some embodiments, purines of the oligonucleotide comprise 2' fluoro modified purines, and pyrimidines of the oligonucleotide comprise 2'-O-methyl modified pyrimidines. In some embodiments, purines of the oligonucleotide comprise 2'-O-methyl modified purines, and pyrimidines of the oligonucleotide comprise 2' fluoro modified pyrimidines. In some embodiments, pyrimidines of the oligonucleotide comprise 2' fluoro modified pyrimidines, and purines of the oligonucleotide comprise a mixture of 2' fluoro and 2'-O-methyl modified purines. In some embodiments, pyrimidines of the oligonucleotide comprise 2'-O-methyl modified pyrimidines, and purines of the oligonucleotide comprise a mixture of 2' fluoro and 2'-O-methyl modified purines. In some embodiments, pyrimidines of the oligonucleotide comprise 2' fluoro modified pyrimidines, and purines of the oligonucleotide comprise 2'-O-methyl modified purines. In some embodiments, pyrimidines of the oligonucleotide comprise 2'-O-methyl modified pyrimidines, and purines of the oligonucleotide comprise 2' fluoro modified purines.

In some embodiments, all purines of the oligonucleotide comprise 2' fluoro modified purines, and all pyrimidines of the oligonucleotide comprise a mixture of 2' fluoro and 2'-O-methyl modified pyrimidines. In some embodiments, all purines of the oligonucleotide comprise 2'-O-methyl modified purines, and all pyrimidines of the oligonucleotide comprise a mixture of 2' fluoro and 2'-O-methyl modified pyrimidines. In some embodiments, all purines of the oligonucleotide comprise 2' fluoro modified purines, and all pyrimidines of the oligonucleotide comprise 2'-O-methyl modified pyrimidines. In some embodiments, all purines of the oligonucleotide comprise 2'-O-methyl modified purines, and all pyrimidines of the oligonucleotide comprise 2' fluoro modified pyrimidines. In some embodiments, all pyrimidines of the oligonucleotide comprise 2' fluoro modified pyrimidines, and all purines of the oligonucleotide comprise a mixture of 2' fluoro and 2'-O-methyl modified purines. In some embodiments, all pyrimidines of the oligonucleotide comprise 2'-O-methyl modified pyrimidines, and all purines of the oligonucleotide comprise a mixture of 2' fluoro and 2'-O-methyl modified purines. In some embodiments, all pyrimidines of the oligonucleotide comprise 2' fluoro modified pyrimidines, and all purines of the oligonucleotide comprise 2'-O-methyl modified purines. In some embodiments, all pyrimidines of the oligonucleotide comprise 2'-O-methyl modified pyrimidines, and all purines of the oligonucleotide comprise 2' fluoro modified purines.

In some embodiments, position nine of the sense strand comprises a 2' fluoro-modified pyrimidine. In some embodiments, all purines of the sense strand comprise 2'-O-methyl modified purines. In some embodiments, 1, 2, 3, 4, or 5 pyrimidines between positions 5 and 11 comprise a 2'flouro-modified pyrimidine, provided there are not three 2' fluoro-modified pyrimidines in a row. In some embodiments, the odd-numbered positions of the antisense strand comprise 2'-O-methyl modified nucleotides. In some embodiments, the even-numbered positions of the antisense strand comprise 2'flouro-modified nucleotides and unmodified deoxyribonucleotide. In some embodiments, position nine of the sense strand comprises a 2' fluoro-modified pyrimidine; all purines of the sense strand comprises 2'-O-methyl modified purines; 1, 2, 3, 4, or 5 pyrimidines between positions 5 and 11 comprise a 2'flouro-modified pyrimidine, provided there are not three 2' fluoro-modified pyrimidines in a row; the odd-numbered positions of the antisense strand comprise 2'-O-methyl modified nucleotides; and the even-numbered positions of the antisense strand comprise 2'flouro-modified nucleotides and unmodified deoxyribonucleotides.

In some embodiments, position nine of the sense strand comprises a 2' fluoro-modified purine. In some embodiments, all pyrimidines of the sense strand comprise 2'-O-methyl modified purines. In some embodiments, 1, 2, 3, 4, or 5 purines between positions 5 and 11 comprise a 2'flouro-modified purine, provided there are not three 2' fluoro-modified purine in a row. In some embodiments, the odd-numbered positions of the antisense strand comprise 2'-O-methyl modified nucleotides. In some embodiments, the even-numbered positions of the antisense strand comprise 2'flouro-modified nucleotides and unmodified deoxyribonucleotide. In some embodiments, position nine of the sense strand comprises a 2' fluoro-modified purine; all pyrimidine of the sense strand comprises 2'-O-methyl modified pyrimidines; 1, 2, 3, 4, or 5 purines between positions 5 and 11 comprise a 2'flouro-modified purines, provided there are not three 2' fluoro-modified purines in a row; the odd-numbered positions of the antisense strand comprise 2'-O-methyl modified nucleotides; and the even-numbered positions of the antisense strand comprise 2'flouro-modified nucleotides and unmodified deoxyribonucleotides. In some embodiments, there are not three 2' fluoro-modified purines in a row. In some embodiments, there are not three 2' fluoro-modified pyrimidines in a row.

In some embodiments, position nine of the sense strand comprises an unmodified deoxyribonucleotide. In some embodiments, positions 5, 7, and 8 of the sense strand comprise 2'fluoro-modified nucleotides. In some embodiments, all pyrimidines in positions 10 to 21 of the sense strand comprise 2'-O-methyl modified pyrimidines and all purines in positions 10 to 21 of the comprise 2'-O-methyl modified purines or 2'fluoro-modified purines. In some embodiments, the odd-numbered positions of the antisense strand comprise 2'-O-methyl modified nucleotides. In some embodiments, the even-numbered positions of the antisense strand comprise 2'flouro-modified nucleotides and unmodified deoxyribonucleotides. In some embodiments, position nine of the sense strand comprises an unmodified deoxyribonucleotide; positions 5, 7, and 8 of the sense strand comprise 2'fluoro-modified nucleotides; all pyrimidines in positions 10 to 21 of the sense strand comprise 2'-O-methyl modified pyrimidines and all purines in positions 10 to 21 of the comprise 2'-O-methyl modified purines or 2'fluoro-modified purines; the odd-numbered positions of the antisense strand comprise 2'-O-methyl modified nucleotides; and the even-numbered positions of the antisense strand comprise 2'flouro-modified nucleotides and unmodified deoxyribonucleotides.

In some embodiments, position nine of the sense strand comprises an unmodified deoxyribonucleotide. In some embodiments, positions 5, 7, and 8 of the sense strand comprise 2'fluoro-modified nucleotides. In some embodiments, all purines in positions 10 to 21 of the sense strand comprise 2'-O-methyl modified purines and all pyrimidines in positions 10 to 21 of the comprise 2'-O-methyl modified pyrimidines or 2'fluoro-modified pyrimidines. In some embodiments, the odd-numbered positions of the antisense strand comprise 2'-O-methyl modified nucleotides. In some embodiments, the even-numbered positions of the antisense strand comprise 2'flouro-modified nucleotides and unmodified deoxyribonucleotides. In some embodiments, position nine of the sense strand comprises an unmodified deoxyribonucleotide; positions 5, 7, and 8 of the sense strand comprise 2'fluoro-modified nucleotides; all purines in positions 10 to 21 of the sense strand comprise 2'-O-methyl modified purines and all pyrimidines in positions 10 to 21 of the comprise 2'-O-methyl modified pyrimidines or 2'fluoro-modified pyrimidines; the odd-numbered positions of the antisense strand comprise 2'-O-methyl modified nucleotides; and the even-numbered positions of the antisense strand comprise 2'flouro-modified nucleotides and unmodified deoxyribonucleotide.

The modifications described herein may be useful for delivery to a cell or tissue, for example, extrahepatic delivery or targeting of an oligonucleotide composition. The modifications described herein may be useful for targeting an oligonucleotide composition to a cell or tissue.

1. Modified siRNAs

In some embodiments, the composition comprises an oligonucleotide that inhibits the expression of a target nucleic acid, wherein the oligonucleotide comprises an siRNA comprising a sense strand and an antisense strand, wherein the sense strand comprises modification pattern 1S: 5'-NfsnNfnNfnNfnNfnNfnNfnNfnNfnNfnNfsnsn-3', wherein "Nf" is a 2' fluoro-modified nucleoside, "n" is a 2' O-methyl modified nucleoside, and "s" is a phosphorothioate linkage. In some embodiments, the sense strand comprises modification pattern 2S: 5'-NfsnNfnNfnNfnNfnNfnNfnNfnNfnNfnNfsnsn-3', wherein "Nf" is a 2' fluoro-modified nucleoside, "n" is a 2' O-methyl modified nucleoside, and "s" is a phosphorothioate linkage. In some embodiments, the sense strand comprises modification pattern 3S: 5'-NfnNfnNfnNfnNfnNfnNfnNfnNfnNfnNfsnsn-3', wherein "Nf" is a 2' fluoro-modified nucleoside, "n" is a 2' O-methyl modified nucleoside, and "s" is a phosphorothioate linkage. In some embodiments, the sense strand comprises modification pattern 4S: 5'-NfsnsNfnNfnNfnNfnNfnNfnNfnNfnNfnNfsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 5S: 5'-nnnnnnnNfnNfnnnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 6S: 5'-nnnnnnnNfNfNfNfnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 7S: 5'-nnnnNfnnnNfnNfnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 8S: 5'-nnnnnnnNfnNfnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 9S: 5'-nnnnnnnNfNfNfNfNfnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 10S: 5'-nnnnNfnNfNfNfnnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 11S: 5'-nnnnnNfNfNfNfnNfnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 12S: 5'-nnnnnNfNfNfNfnnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 13S: 5'-nnnnNfNfNfNfNfnnnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 14S: 5'-nnnnnnnnNfNfnnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 15S: 5'-nnnnnnNfNfNfNfnnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 16S: 5'-nnnnNfnNfnnNfnNfnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 17S: 5'-nnnnNfnNfnNfnNfnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 18S: 5'-nnnnnNfnnNfnNfNfnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 19S: 5'-nnnnnNfnNfNfnnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 20S: 5'-nnnnnnNfNfNfnnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 21S: 5'-nNfnNfnNfnNfnNfnnnnnNfnNfNfnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 22S: 5'-snnnnNfNfNfnNfnNfnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 23S: 5'-snnnnNfNfNfNfnnnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 24S: 5'-snnnnNfNfNfNfNfnnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 25S: 5'-snnnnnnnnNfNfnnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 26S: 5'-snnnnNfnnNfnNfnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 27S: 5'-snNfnNfnNfnNfnNfnnnnnNfnNfNfnsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 28S: 5'-NfnNfnNfnNfnNfNfnNfnNfnNfnNfnNfsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 29S: 5'-nnNfnNfnNfnNfnNfnNfnnnNfnNfsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 30S: 5'-nnnnnNfNfNfNfnnnnnnnnnnsnsn-3', wherein "Nf" is a 2' fluoro-modified nucleoside, "n" is a 2' O-methyl modified nucleoside, "s" is a phosphorothioate linkage, and N comprises one or more nucleosides.

In some embodiments, the composition comprises an oligonucleotide that inhibits the expression of the target mRNA, wherein the oligonucleotide comprises an siRNA comprising a sense strand and an antisense strand, wherein the antisense strand comprises modification pattern 1AS: 5'-nsNfsnNfnNfnNfnNfnNfnNfnNfnNfnsnsn-3', wherein "Nf" is a 2' fluoro-modified nucleoside, "n" is a 2' O-methyl modified nucleoside, and "s" is a phosphorothioate linkage. In some embodiments, the antisense strand comprises modification pattern 2AS: 5'-nsNfsnNfnNfnNfnNfnnnNfnNfnNfsnsn-3', wherein "Nf" is a 2' fluoro-modified nucleoside, "n" is a 2' O-methyl modified nucleoside, and "s" is a phosphorothioate linkage. In some embodiments, the antisense strand comprises modification pattern 3AS: 5'-nsnsnNfnNfnNfnNfnNfnNfnNfnNfnsnsn-3', wherein "Nf" is a 2' fluoro-modified nucleoside, "n" is a 2' O-methyl modified nucleoside, and "s" is a phosphorothioate linkage. In some embodiments, the antisense strand comprises modification pattern 4AS: 5'-nsNfsnnnNfnNfnnnnnNfnNfnnnsnsn-3', wherein "Nf" is a 2' fluoro-modified nucleoside, "n" is a 2' O-methyl modified nucleoside, and "s" is a phosphorothioate linkage. In some embodiments, the antisense strand comprises modification pattern 5AS: 5'-nsNfsnnnNfnNfnNfnNfnNfnNfnNfnsnsn-3', wherein "Nf" is a 2' fluoro-modified nucleoside, "n" is a 2' O-methyl modified nucleoside, and "s" is a phosphorothioate linkage.

In some embodiments, the composition comprises an oligonucleotide that inhibits the expression of a target nucleic acid, wherein the oligonucleotide comprises an siRNA comprising a sense strand and an antisense strand, wherein the sense strand comprises pattern 1S and the antisense strand comprises pattern 1AS, 2AS, 3AS, 4AS, or 5AS. In some embodiments, the sense strand comprises pattern 2S and the antisense strand comprises pattern 1AS, 2AS, 3AS, 4AS, or 5AS. In some embodiments, the sense strand comprises pattern 3S and the antisense strand comprises 1AS, 2AS, 3AS, 4AS, or 5AS. In some embodiments, the sense strand comprises pattern 4S and the antisense strand comprises 1AS, 2AS, 3AS, 4AS, or 5AS. In some embodiments, the sense strand comprises pattern 5S and the antisense strand comprises 1AS, 2AS, 3AS, 4AS, or 5AS. In some embodiments, the sense strand comprises pattern 6S and the antisense strand comprises 1AS, 2AS, 3AS, 4AS, or 5AS. In some embodiments, the sense strand comprises pattern 7S and the antisense strand comprises 1AS, 2AS, 3AS, 4AS, or 5AS. In some embodiments, the sense strand comprises pattern 8S and the antisense strand comprises 1AS, 2AS, 3AS, 4AS, or 5AS. In some embodiments, the sense strand comprises pattern 9S and the antisense strand comprises 1AS, 2AS, 3AS, 4AS, or 5AS. In some embodiments, the sense strand comprises pattern 10S and the antisense strand comprises 1AS, 2AS, 3AS, 4AS, or 5AS. In some embodiments, the sense strand comprises pattern 11S and the antisense strand comprises pattern 1AS, 2AS, 3AS, 4AS, or 5AS. In some embodiments, the sense strand comprises pattern 12S and the antisense strand comprises pattern 1AS, 2AS, 3AS, 4AS, or 5AS. In some embodiments, the sense strand comprises pattern 13S and the antisense strand comprises 1AS, 2AS, 3AS, 4AS, or 5AS. In some embodiments, the sense strand comprises pattern 14S and the antisense strand comprises 1AS, 2AS, 3AS, 4A5, or 5AS. In some embodiments, the sense strand comprises pattern 15S and the antisense strand comprises 1AS, 2AS, 3AS, 4AS, or 5AS. In some embodiments, the sense strand comprises pattern 16S and the antisense strand comprises 1AS, 2AS, 3AS, 4AS, or 5AS. In some embodiments, the sense strand comprises pattern 17S and the antisense strand comprises 1AS, 2AS, 3AS, 4AS, or 5AS. In some embodiments, the sense strand comprises pattern 18S and the antisense strand comprises 1AS, 2AS, 3AS, 4AS, or 5AS. In some embodiments, the sense strand comprises pattern 19S and the antisense strand comprises 1AS, 2AS, 3AS, 4AS, or 5AS. In some embodiments, the sense strand comprises pattern 20S and the antisense strand comprises 1AS, 2AS, 3AS, 4AS, or 5AS. In some embodiments, the sense strand comprises pattern 21S and the antisense strand comprises pattern 1AS, 2AS, 3AS, 4AS, or 5AS. In some embodiments, the sense strand comprises pattern 22S and the antisense strand comprises pattern 1AS, 2AS, 3AS, 4AS, or 5AS. In some embodiments, the sense strand comprises pattern 23S and the antisense strand comprises 1AS, 2AS, 3AS, 4AS, or 5AS. In some embodiments, the sense strand comprises pattern 24S and the antisense strand comprises 1AS, 2AS, 3AS, 4AS, or 5AS. In some embodiments, the sense strand comprises pattern 25S and the antisense strand comprises 1AS, 2AS, 3AS, 4AS, or 5AS. In some embodiments, the sense strand comprises pattern 26S and the antisense strand comprises 1AS, 2AS, 3AS, 4AS, or 5AS. In some embodiments, the sense strand comprises pattern 27S and the antisense strand comprises 1AS, 2AS, 3AS, 4AS, or 5AS. In some embodiments, the sense strand comprises pattern 28S and the antisense strand comprises 1AS, 2AS, 3AS, 4AS, or 5AS. In some embodiments, the sense strand comprises pattern 29S and the antisense strand comprises 1AS, 2AS, 3AS, 4AS, or 5AS. In some embodiments, the sense strand comprises pattern 30S and the antisense strand comprises 1AS, 2AS, 3AS, 4AS, or 5AS.

In some embodiments, the sense strand comprises pattern 1S, 2S, 3S, 4S, 5S, 6S, 7S, 8S, 9S, 10S, 11S, 12S, 13S, 14S, 15S, 16S, 17S, 18S, 19S, 20S, 21S, 22S, 23S, 24S, 25S, 26S, 27S, 28S, 29S, or 30S and the antisense strand comprises pattern 1AS. In some embodiments, the sense strand comprises pattern 1S, 2S, 3S, 4S, 5S, 6S, 7S, 8S, 9S, 10S, 11S, 12S, 13S, 14S, 15S, 16S, 17S, 18S, 19S, 20S, 21S, 22S, 23S, 24S, 25S, 26S, 27S, 28S, 29S, or 30S and the antisense strand comprises pattern 2AS. In some embodiments, the sense strand comprises pattern 1S, 2S, 3S, 4S, 5S, 6S, 7S, 8S, 9S, 10S, 11S, 12S, 13S, 14S, 15S, 16S, 17S, 18S, 19S, 20S, 21S, 22S, 23S, 24S, 25S, 26S, 27S, 28S, 29S, or 30S and the antisense strand comprises pattern 3AS. In some embodiments, the sense strand comprises pattern 1S, 2S, 3S, 4S, 5S, 6S, 7S, 8S, 9S, 10S, 11S, 12S, 13S, 14S, 15S, 16S, 17S, 18S, 19S, 20S, 21S, 22S, 23S, 24S, 25S, 26S, 27S, 28S, 29S, or 30S and the antisense strand comprises pattern 4AS. In some embodiments, the sense strand comprises pattern 1S, 2S, 3S, 4S, 5S, 6S, 7S, 8S, 9S, 10S, 11S, 12S, 13S, 14S, 15S, 16S, 17S, 18S, 19S, 20S, 21S, 22S, 23S, 24S, 25S, 26S, 27S, 28S, 29S, or 30S and the antisense strand comprises pattern 5A5.

In some embodiments, the sense strand comprises modification pattern 1AS, 2AS, 3AS, or 4AS. In some embodiments, the sense strand or antisense strand comprises modification pattern 1AS, 2AS, 3AS, 4AS, or 5S. In some embodiments, the antisense strand comprises modification pattern 1S, 2S, 3S, 4S, 5S, 6S, 7S, 8S, 9S, 10S, 11S, 12S, 13S, 14S, 15S, 16S, 17S, 18S, 19S, 20S, 21S, 22S, 23S, 24S, 25S, 26S, 27S, 28S, or 29S. In some embodiments, the sense strand or antisense strand comprises modification pattern 1S, 2S, 3S, 4S, 5S, 6S, 7S, 8S, 9S, 10S, 11S, 12S, 13S, 14S, 15S, 16S, 17S, 18S, 19S, 20S, 21S, 22S, 23S, 24S, 25S, 26S, 27S, 28S, 29S, or 30AS.

In some embodiments, purines of the sense strand comprise 2' fluoro modified purines. In some embodiments, purines of the sense strand comprise 2'-O-methyl modified purines. In some embodiments, purines of the sense strand comprise a mixture of 2' fluoro and 2'-O-methyl modified purines. In some embodiments, all purines of the sense strand comprise 2' fluoro modified purines. In some embodiments, all purines of the sense strand comprise 2'-O-methyl modified purines. In some embodiments, all purines of the sense strand comprise a mixture of 2' fluoro and 2'-O-methyl modified purines.

In some embodiments, pyrimidines of the sense strand comprise 2' fluoro modified pyrimidines. In some embodiments, pyrimidines of the sense strand comprise 2'-O-methyl modified pyrimidines. In some embodiments, pyrimidines of the sense strand comprise a mixture of 2' fluoro and 2'-O-methyl modified pyrimidines. In some embodiments, all pyrimidines of the sense strand comprise 2' fluoro modified pyrimidines. In some embodiments, all pyrimidines of the sense strand comprise 2'-O-methyl modified pyrimidines. In some embodiments, all pyrimidines of the sense strand comprise a mixture of 2' fluoro and 2'-O-methyl modified pyrimidines.

In some embodiments, purines of the sense strand comprise 2' fluoro modified purines, and pyrimidines of the sense strand comprise a mixture of 2' fluoro and 2'-O-methyl modified pyrimidines. In some embodiments, purines of the sense strand comprise 2'-O-methyl modified purines, and pyrimidines of the sense strand comprise a mixture of 2' fluoro and 2'-O-methyl modified pyrimidines. In some embodiments, purines of the sense strand comprise 2' fluoro modified purines, and pyrimidines of the sense strand comprise 2'-O-methyl modified pyrimidines. In some embodiments, purines of the sense strand comprise 2'-O-methyl modified purines, and pyrimidines of the sense strand comprise 2' fluoro modified pyrimidines. In some embodiments, pyrimidines of the sense strand comprise 2' fluoro modified pyrimidines, and purines of the sense strand comprise a mixture of 2' fluoro and 2'-O-methyl modified purines. In some embodiments, pyrimidines of the sense strand comprise 2'-O-methyl modified pyrimidines, and purines of the sense strand comprise a mixture of 2' fluoro and 2'-O-methyl modified purines. In some embodiments, pyrimidines of the sense strand comprise 2' fluoro modified pyrimidines, and purines of the sense strand comprise 2'-O-methyl modified purines. In some embodiments, pyrimidines of the sense strand comprise 2'-O-methyl modified pyrimidines, and purines of the sense strand comprise 2' fluoro modified purines.

In some embodiments, all purines of the sense strand comprise 2' fluoro modified purines, and all pyrimidines of the sense strand comprise a mixture of 2' fluoro and 2'-O-methyl modified pyrimidines. In some embodiments, all purines of the sense strand comprise 2'-O-methyl modified purines, and all pyrimidines of the sense strand comprise a mixture of 2' fluoro and 2'-O-methyl modified pyrimidines. In some embodiments, all purines of the sense strand comprise 2' fluoro modified purines, and all pyrimidines of the sense strand comprise 2'-O-methyl modified pyrimidines. In some embodiments, all purines of the sense strand comprise 2'-O-methyl modified purines, and all pyrimidines of the sense strand comprise 2' fluoro modified pyrimidines. In some embodiments, all pyrimidines of the sense strand comprise 2' fluoro modified pyrimidines, and all purines of the sense strand comprise a mixture of 2' fluoro and 2'-O-methyl modified purines. In some embodiments, all pyrimidines of the sense strand comprise 2'-O-methyl modified pyrimidines, and all purines of the sense strand comprise a mixture of 2' fluoro and 2'-O-methyl modified purines. In some embodiments, all pyrimidines of the sense strand comprise 2' fluoro modified pyrimidines, and all purines of the sense strand comprise 2'-O-methyl modified purines. In some embodiments, all pyrimidines of the sense strand comprise 2'-O-methyl modified pyrimidines, and all purines of the sense strand comprise 2' fluoro modified purines.

In some embodiments, purines of the antisense strand comprise 2' fluoro modified purines. In some embodiments, purines of the antisense strand comprise 2'-O-methyl modified purines. In some embodiments, purines of the antisense strand comprise a mixture of 2' fluoro and 2'-O-methyl modified purines. In some embodiments, all purines of the antisense strand comprise 2' fluoro modified purines. In some embodiments, all purines of the antisense strand comprise 2'-O-methyl modified purines. In some embodiments, all purines of the antisense strand comprise a mixture of 2' fluoro and 2'-O-methyl modified purines.

In some embodiments, pyrimidines of the antisense strand comprise 2' fluoro modified pyrimidines. In some embodiments, pyrimidines of the antisense strand comprise 2'-O-methyl modified pyrimidines. In some embodiments, pyrimidines of the antisense strand comprise a mixture of 2' fluoro and 2'-O-methyl modified pyrimidines. In some embodiments, all pyrimidines of the antisense strand comprise 2' fluoro modified pyrimidines. In some embodiments, all pyrimidines of the antisense strand comprise 2'-O-methyl modified pyrimidines. In some embodiments, all pyrimidines of the antisense strand comprise a mixture of 2' fluoro and 2'-O-methyl modified pyrimidines.

In some embodiments, purines of the antisense strand comprise 2' fluoro modified purines, and pyrimidines of the antisense strand comprise a mixture of 2' fluoro and 2'-O-methyl modified pyrimidines. In some embodiments, purines of the antisense strand comprise 2'-O-methyl modified purines, and pyrimidines of the antisense strand comprise a mixture of 2' fluoro and 2'-O-methyl modified pyrimidines. In some embodiments, purines of the antisense strand comprise 2' fluoro modified purines, and pyrimidines of the antisense strand comprise 2'-O-methyl modified pyrimidines. In some embodiments, purines of the antisense strand comprise 2'-O-methyl modified purines, and pyrimidines of the antisense strand comprise 2' fluoro modified pyrimidines. In some embodiments, pyrimidines of the antisense strand comprise 2' fluoro modified pyrimidines, and purines of the antisense strand comprise a mixture of 2' fluoro and 2'-O-methyl modified purines. In some embodiments, pyrimidines of the antisense strand comprise 2'-O-methyl modified pyrimidines, and purines of the antisense strand comprise a mixture of 2' fluoro and 2'-O-methyl modified purines. In some embodiments, pyrimidines of the antisense strand comprise 2' fluoro modified pyrimidines, and purines of the antisense strand comprise 2'-O-methyl modified purines. In some embodiments, pyrimidines of the antisense strand comprise 2'-O-methyl modified pyrimidines, and purines of the antisense strand comprise 2' fluoro modified purines.

In some embodiments, all purines of the antisense strand comprise 2' fluoro modified purines, and all pyrimidines of the antisense strand comprise a mixture of 2' fluoro and 2'-O-methyl modified pyrimidines. In some embodiments, all purines of the antisense strand comprise 2'-O-methyl modified purines, and all pyrimidines of the antisense strand comprise a mixture of 2' fluoro and 2'-O-methyl modified pyrimidines. In some embodiments, all purines of the antisense strand comprise 2' fluoro modified purines, and all pyrimidines of the antisense strand comprise 2'-O-methyl modified pyrimidines. In some embodiments, all purines of the antisense strand comprise 2'-O-methyl modified purines, and all pyrimidines of the antisense strand comprise 2' fluoro modified pyrimidines. In some embodiments, all pyrimidines of the antisense strand comprise 2' fluoro modified pyrimidines, and all purines of the antisense strand comprise a mixture of 2' fluoro and 2'-O-methyl modified purines. In some embodiments, all pyrimidines of the antisense strand comprise 2'-O-methyl modified pyrimidines, and all purines of the antisense strand comprise a mixture of 2' fluoro and 2'-O-methyl modified purines. In some embodiments, all pyrimidines of the antisense strand comprise 2' fluoro modified pyrimidines, and all purines of the antisense strand comprise 2'-O-methyl modified purines. In some embodiments, all pyrimidines of the antisense strand comprise 2'-O-methyl modified pyrimidines, and all purines of the antisense strand comprise 2' fluoro modified purines.

In some embodiments, the siRNA comprises a sense strand, an antisense strand, and a lipid moiety connected to an end of the sense or antisense strand; wherein the lipid moiety comprises a phenyl or cyclohexanyl linker, wherein the linker is connected to a lipid and to the end of the sense or antisense strand. In some embodiments, any one of the following is true with regard to the sense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2' fluoro modified purines, and all pyrimidines comprise 2'-O-methyl modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2' fluoro modified pyrimidines, and all purines comprise 2'-O-methyl modified purines. In some embodiments, any one of the following is true with regard to the antisense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2'-O-methyl modified purines, and all pyrimidines comprise 2' fluoro modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2'-O-methyl modified pyrimidines, and all purines comprise 2' fluoro modified purines. In some embodiments, the siRNA comprises comprising a sense strand and an antisense strand; wherein the antisense strand comprises a 5' end comprising a vinyl phosphonate and 2 phosphorothioate linkages, and a 3' end comprising 2 phosphorothioate linkages; wherein the sense strand comprises a 5' end comprising a hydrophobic moiety, and a 3' end comprising 2 phosphorothioate linkages; wherein any one of the following is true with regard to the sense strand: all purines comprise 2' fluoro modified purines, and all pyrimidines comprise a mixture of 2' fluoro and 2'-O-methyl modified pyrimidines, all purines comprise 2'-O-methyl modified purines, and all pyrimidines comprise a mixture of 2' fluoro and 2'-O-methyl modified pyrimidines, all purines comprise 2' fluoro modified purines, and all pyrimidines comprise 2'-O-methyl modified pyrimidines, all pyrimidines comprise 2' fluoro modified pyrimidines, and all purines comprise a mixture of 2' fluoro and 2'-O-methyl modified purines, all pyrimidines comprise 2'-O-methyl modified pyrimidines, and all purines comprise a mixture of 2' fluoro and 2'-O-methyl modified purines, or all pyrimidines comprise 2' fluoro modified pyrimidines, and all purines comprise 2'-O-methyl modified purines; and wherein any one of the following is true with regard to the antisense strand: all purines comprise 2' fluoro modified purines, and all pyrimidines comprise a mixture of 2' fluoro and 2'-O-methyl modified pyrimidines, all purines comprise 2'-O-methyl modified purines, and all pyrimidines comprise a mixture of 2' fluoro and 2'-O-methyl modified pyrimidines, all purines comprise 2'-O-methyl modified purines, and all pyrimidines comprise 2' fluoro modified pyrimidines, all pyrimidines comprise 2' fluoro modified pyrimidines, and all purines comprise a mixture of 2' fluoro and 2'-O-methyl modified purines, all pyrimidines comprise 2'-O-methyl modified pyrimidines, and all purines comprise a mixture of 2' fluoro and 2'-O-methyl modified purines, or all pyrimidines comprise 2'-O-methyl modified pyrimidines, and all purines comprise 2' fluoro modified purines.

In some embodiments, any one of the following is true with regard to the sense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2' fluoro modified purines, and all pyrimidines comprise 2'-O-methyl modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2' fluoro modified pyrimidines, and all purines comprise 2'-O-methyl modified purines; with the proviso that in any of the foregoing, the sense strand may include a deoxy nucleoside. In some embodiments, all purines comprise 2' fluoro modified purines, and all pyrimidines comprise a mixture of 2' fluoro and 2'-O-methyl modified pyrimidines; with the proviso that a deoxy nucleoside may be included in the sense strand. In some embodiments, in the sense strand, all purines comprise 2'-O-methyl modified purines, and all pyrimidines comprise a mixture of 2' fluoro and 2'-O-methyl modified pyrimidines; with the proviso that a deoxy nucleoside may be included in the sense strand. In some embodiments, in the sense strand, all purines comprise 2' fluoro modified purines, and all pyrimidines comprise 2'-O-methyl modified pyrimidines; with the proviso that a deoxy nucleoside may be included in the sense strand. In some embodiments, all pyrimidines comprise 2' fluoro modified pyrimidines, and all purines comprise a mixture of 2' fluoro and 2'-O-methyl modified purines; with the proviso that a deoxy nucleoside may be included in the sense strand. In some embodiments, in the sense strand, all pyrimidines comprise 2'-O-methyl modified pyrimidines, and all purines comprise a mixture of 2' fluoro and 2'-O-methyl modified purines; with the proviso that a deoxy nucleoside may be included in the sense strand. In some embodiments, in the sense strand, all pyrimidines comprise 2' fluoro modified pyrimidines, and all purines comprise 2'-O-methyl modified purines; with the proviso that a deoxy nucleoside may be included in the sense strand. In some embodiments, the sense strand includes the deoxy nucleoside. The deoxy nucleoside may be at nucleoside position 9 of the sense strand. In some embodiments, the sense strand does not include a deoxy nucleoside. The deoxy nucleoside of the sense strand may be otherwise unmodified.

In some embodiments, any one of the following is true with regard to the antisense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2'-O-methyl modified purines, and all pyrimidines comprise 2' fluoro modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2'-O-methyl modified pyrimidines, and all purines comprise 2' fluoro modified purines; with the proviso that in any of the foregoing, the sense strand may include a deoxy nucleoside. In some embodiments, all purines comprise 2' fluoro modified purines, and all pyrimidines comprise a mixture of 2' fluoro and 2'-O-methyl modified pyrimidines; with the proviso that a deoxy nucleoside may be included in the antisense strand. In some embodiments, in the antisense strand, all purines comprise 2'-O-methyl modified purines, and all pyrimidines comprise a mixture of 2' fluoro and 2'-O-methyl modified pyrimidines; with the proviso that a deoxy nucleoside may be included in the antisense strand. In some embodiments, in the antisense strand, all purines comprise 2'-O-methyl modified purines, and all pyrimidines comprise 2' fluoro modified pyrimidines; with the proviso that a deoxy nucleoside may be included in the antisense strand. In some embodiments, in the antisense strand, all pyrimidines comprise 2' fluoro modified pyrimidines, and all purines comprise a mixture of 2' fluoro and 2'-O-methyl modified purines; with the proviso that a deoxy nucleoside may be included in the antisense strand. In some embodiments, in the antisense strand, all pyrimidines comprise 2'-O-methyl modified pyrimidines, and all purines comprise a mixture of 2' fluoro and 2'-O-methyl modified purines; with the proviso that a deoxy nucleoside may be included in the antisense strand. In some embodiments, in the antisense strand, all pyrimidines comprise 2'-O-methyl modified pyrimidines, and all purines comprise 2' fluoro modified purines; with the proviso that a deoxy nucleoside may be included in the antisense strand. In some embodiments, the antisense strand includes the deoxy nucleoside. The deoxy nucleoside may be at nucleoside position 9 of the antisense strand. In some embodiments, the antisense strand does not include a deoxy nucleoside. The deoxy nucleoside of the antisense strand may be otherwise unmodified.

In some embodiments, any one of the following is true with regard to the sense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2' fluoro modified purines, and all pyrimidines comprise 2'-O-methyl modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2' fluoro modified pyrimidines, and all purines comprise 2'-O-methyl modified purines; with the proviso that in any of the foregoing, the sense strand may include a deoxy nucleoside or a 2'-O-methoxyethyl nucleoside. In some embodiments, all purines comprise 2' fluoro modified purines, and all pyrimidines comprise a mixture of 2' fluoro and 2'-O-methyl modified pyrimidines; with the proviso that a deoxy nucleoside or a 2'-O-methoxyethyl nucleoside may be included in the sense strand. In some embodiments, in the sense strand, all purines comprise 2'-O-methyl modified purines, and all pyrimidines comprise a mixture of 2' fluoro and 2'-O-methyl modified pyrimidines; with the proviso that a deoxy nucleoside or a 2'-O-methoxyethyl nucleoside may be included in the sense strand. In some embodiments, in the sense strand, all purines comprise 2' fluoro modified purines, and all pyrimidines comprise 2'-O-methyl modified pyrimidines; with the proviso that a deoxy nucleoside or a 2'-O-methoxyethyl nucleoside may be included in the sense strand. In some embodiments, all pyrimidines comprise 2' fluoro modified pyrimidines, and all purines comprise a mixture of 2' fluoro and 2'-O-methyl modified purines; with the proviso that a deoxy nucleoside or a 2'-O-methoxyethyl nucleoside may be included in the sense strand. In some embodiments, in the sense strand, all pyrimidines comprise 2'-O-methyl modified pyrimidines, and all purines comprise a mixture of 2' fluoro and 2'-O-methyl modified purines; with the proviso that a deoxy nucleoside or a 2'-O-methoxyethyl nucleoside may be included in the sense strand. In some embodiments, in the sense strand, all pyrimidines comprise 2' fluoro modified pyrimidines, and all purines comprise 2'-O-methyl modified purines; with the proviso that a deoxy nucleoside or a 2'-O-methoxyethyl nucleoside may be included in the sense strand. In some embodiments, the sense strand includes the deoxy nucleoside. The deoxy nucleoside may be at nucleoside position 9 of the sense strand. In some embodiments, the sense strand does not include a deoxy nucleoside. The deoxy nucleoside of the sense strand may be otherwise unmodified. In some embodiments, the sense strand includes the a 2'-O-methoxyethyl nucleoside. The 2'-O-methoxyethyl nucleoside may be at nucleoside position 4 of the sense strand. The 2'-O-methoxyethyl nucleoside may include a 2'-O-methoxyethyl thymine nucleoside. In some embodiments, the sense strand does not include the a 2'-O-methoxyethyl nucleoside. The 2'-O-methoxyethyl nucleoside of the sense strand may be otherwise unmodified.

In some embodiments, any one of the following is true with regard to the antisense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2'-O-methyl modified purines, and all pyrimidines comprise 2' fluoro modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2'-O-methyl modified pyrimidines, and all purines comprise 2' fluoro modified purines; with the proviso that in any of the foregoing, the sense strand may include a deoxy nucleoside or a 2'-O-methoxyethyl nucleoside. In some embodiments, all purines comprise 2' fluoro modified purines, and all pyrimidines comprise a mixture of 2' fluoro and 2'-O-methyl modified pyrimidines; with the proviso that a deoxy nucleoside or a 2'-O-methoxyethyl nucleoside may be included in the antisense strand. In some embodiments, in the antisense strand, all purines comprise 2'-O-methyl modified purines, and all pyrimidines comprise a mixture of 2' fluoro and 2'-O-methyl modified pyrimidines; with the proviso that a deoxy nucleoside or a 2'-O-methoxyethyl nucleoside may be included in the antisense strand. In some embodiments, in the antisense strand, all purines comprise 2'-O-methyl modified purines, and all pyrimidines comprise 2' fluoro modified pyrimidines; with the proviso that a deoxy nucleoside or a 2'-O-methoxyethyl nucleoside may be included in the antisense strand. In some embodiments, in the antisense strand, all pyrimidines comprise 2' fluoro modified pyrimidines, and all purines comprise a mixture of 2' fluoro and 2'-O-methyl modified purines; with the proviso that a deoxy nucleoside or a 2'-O-methoxyethyl nucleoside may be included in the antisense strand. In some embodiments, in the antisense strand, all pyrimidines comprise 2'-O-methyl modified pyrimidines, and all purines comprise a mixture of 2' fluoro and 2'-O-methyl modified purines; with the proviso that a deoxy nucleoside or a 2'-O-methoxyethyl nucleoside may be included in the antisense strand. In some embodiments, in the antisense strand, all pyrimidines comprise 2'-O-methyl modified pyrimidines, and all purines comprise 2' fluoro modified purines; with the proviso that a deoxy nucleoside or a 2'-O-methoxyethyl nucleoside may be included in the antisense strand. In some embodiments, the antisense strand includes the deoxy nucleoside. The deoxy nucleoside may be at nucleoside position 9 of the antisense strand. In some embodiments, the antisense strand does not include a deoxy nucleoside. The deoxy nucleoside of the antisense strand may be otherwise unmodified. In some embodiments, the antisense strand includes the a 2'-O-methoxyethyl nucleoside. The 2'-O-methoxyethyl nucleoside may be at nucleoside position 4 of the sense strand. The 2'-O-methoxyethyl nucleoside may include a 2'-O-methoxyethyl thymine nucleoside. In some embodiments, the antisense strand does not include the a 2'-O-methoxyethyl nucleoside. The 2'-O-methoxyethyl nucleoside of the antisense strand may be otherwise unmodified.

In some embodiments, any one of the following is true with regard to the sense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2' fluoro modified purines, and all pyrimidines comprise 2'-O-methyl modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2' fluoro modified pyrimidines, and all purines comprise 2'-O-methyl modified purines; with the proviso that in any of the foregoing, the sense strand may include a 2'-O-methoxyethyl nucleoside. In some embodiments, all purines comprise 2' fluoro modified purines, and all pyrimidines comprise a mixture of 2' fluoro and 2'-O-methyl modified pyrimidines; with the proviso that a 2'-O-methoxyethyl nucleoside may be included in the sense strand. In some embodiments, in the sense strand, all purines comprise 2'-O-methyl modified purines, and all pyrimidines comprise a mixture of 2' fluoro and 2'-O-methyl modified pyrimidines; with the proviso that a 2'-O-methoxyethyl nucleoside may be included in the sense strand. In some embodiments, in the sense strand, all purines comprise 2' fluoro modified purines, and all pyrimidines comprise 2'-O-methyl modified pyrimidines; with the proviso that a 2'-O-methoxyethyl nucleoside may be included in the sense strand. In some embodiments, all pyrimidines comprise 2' fluoro modified pyrimidines, and all purines comprise a mixture of 2' fluoro and 2'-O-methyl modified purines; with the proviso that a 2'-O-methoxyethyl nucleoside may be included in the sense strand. In some embodiments, in the sense strand, all pyrimidines comprise 2'-O-methyl modified pyrimidines, and all purines comprise a mixture of 2' fluoro and 2'-O-methyl modified purines; with the proviso that a 2'-O-methoxyethyl nucleoside may be included in the sense strand. In some embodiments, in the sense strand, all pyrimidines comprise 2' fluoro modified pyrimidines, and all purines comprise 2'-O-methyl modified purines; with the proviso that a 2'-O-methoxyethyl nucleoside may be included in the sense strand. In some embodiments, the sense strand includes the a 2'-O-methoxyethyl nucleoside. The 2'-O-methoxyethyl nucleoside may be at nucleoside position 4 of the sense strand. The 2'-O-methoxyethyl nucleoside may include a 2'-O-methoxyethyl thymine nucleoside. In some embodiments, the sense strand does not include the a 2'-O-methoxyethyl nucleoside. The 2'-O-methoxyethyl nucleoside of the sense strand may be otherwise unmodified.

In some embodiments, any one of the following is true with regard to the antisense strand: all purines comprise 2' fluoro modified purines, and all pyrimidines comprise a mixture of 2' fluoro and 2'-O-methyl modified pyrimidines; all purines comprise 2'-O-methyl modified purines, and all pyrimidines comprise a mixture of 2' fluoro and 2'-O-methyl modified pyrimidines; all purines comprise 2'-O-methyl modified purines, and all pyrimidines comprise 2' fluoro modified pyrimidines; all pyrimidines comprise 2' fluoro modified pyrimidines, and all purines comprise a mixture of 2' fluoro and 2'-O-methyl modified purines; all pyrimidines comprise 2'-O-methyl modified pyrimidines, and all purines comprise a mixture of 2' fluoro and 2'-O-methyl modified purines; or all pyrimidines comprise 2'-O-methyl modified pyrimidines, and all purines comprise 2' fluoro modified purines; with the proviso that in any of the foregoing, the sense strand may include a deoxy nucleoside or a 2'-O-methoxyethyl nucleoside. In some embodiments, all purines comprise 2' fluoro modified purines, and all pyrimidines comprise a mixture of 2' fluoro and 2'-O-methyl modified pyrimidines; with the proviso that a 2'-O-methoxyethyl nucleoside may be included in the antisense strand. In some embodiments, in the antisense strand, all purines comprise 2'-O-methyl modified purines, and all pyrimidines comprise a mixture of 2' fluoro and 2'-O-methyl modified pyrimidines; with the proviso that a 2'-O-methoxyethyl nucleoside may be included in the antisense strand. In some embodiments, in the antisense strand, all purines comprise 2'-O-methyl modified purines, and all pyrimidines comprise 2' fluoro modified pyrimidines; with the proviso that a 2'-O-methoxyethyl nucleoside may be included in the antisense strand. In some embodiments, in the antisense strand, all pyrimidines comprise 2' fluoro modified pyrimidines, and all purines comprise a mixture of 2' fluoro and 2'-O-methyl modified purines; with the proviso that a 2'-O-methoxyethyl nucleoside may be included in the antisense strand. In some embodiments, in the antisense strand, all pyrimidines comprise 2'-O-methyl modified pyrimidines, and all purines comprise a mixture of 2' fluoro and 2'-O-methyl modified purines; with the proviso that a 2'-O-methoxyethyl nucleoside may be included in the antisense strand. In some embodiments, in the antisense strand, all pyrimidines comprise 2'-O-methyl modified pyrimidines, and all purines comprise 2' fluoro modified purines; with the proviso that a 2'-O-methoxyethyl nucleoside may be included in the antisense strand. In some embodiments, the antisense strand includes the a 2'-O-methoxyethyl nucleoside. The 2'-O-methoxyethyl nucleoside may be at nucleoside position 4 of the sense strand. The 2'-O-methoxyethyl nucleoside may include a 2'-O-methoxyethyl thymine nucleoside. In some embodiments, the antisense strand does not include the a 2'-O-methoxyethyl nucleoside. The 2'-O-methoxyethyl nucleoside of the antisense strand may be otherwise unmodified.

In some embodiments, any one of the following is true with regard to the sense strand, with the proviso that the sense strand may include a 2' deoxy nucleoside: all purine nucleosides comprise 2' fluoro, and all pyrimidine nucleosides are modified with a mixture of 2' fluoro and 2'-O-methyl, all purine nucleosides comprise 2'-O-methyl, and all pyrimidine nucleosides are modified with a mixture of 2' fluoro and 2'-O-methyl, all purine nucleosides comprise 2' fluoro, and all pyrimidine nucleosides comprise 2'-O-methyl, all pyrimidine nucleosides comprise 2' fluoro, and all purine nucleosides are modified with a mixture of 2' fluoro and 2'-O-methyl, all pyrimidine nucleosides comprise 2'-O-methyl, and all purine nucleosides are modified with a mixture of 2' fluoro and 2'-O-methyl, or all pyrimidine nucleosides comprise 2' fluoro, and all purine nucleosides comprise 2'-O-methyl. In some embodiments, in the sense strand, all purine nucleosides comprise 2' fluoro, and all pyrimidine nucleosides are modified with a mixture of 2' fluoro and 2'-O-methyl, with the proviso that the sense strand may include a 2' deoxy nucleoside. In some embodiments, in the sense strand, all purine nucleosides comprise 2'-O-methyl, and all pyrimidine nucleosides are modified with a mixture of 2' fluoro and 2'-O-methyl, with the proviso that the sense strand may include a 2' deoxy nucleoside. In some embodiments, in the sense strand, all purine nucleosides comprise 2' fluoro, and all pyrimidine nucleosides comprise 2'-O-methyl, with the proviso that the sense strand may include a 2' deoxy nucleoside. In some embodiments, in the sense strand, all pyrimidine nucleosides comprise 2' fluoro, and all purine nucleosides are modified with a mixture of 2' fluoro and 2'-O-methyl, with the proviso that the sense strand may include a 2' deoxy nucleoside. In some embodiments, in the sense strand, all pyrimidine nucleosides comprise 2'-O-methyl, and all purine nucleosides are modified with a mixture of 2' fluoro and 2'-O-methyl, with the proviso that the sense strand may include a 2' deoxy nucleoside. In some embodiments, in the sense strand, all pyrimidine nucleosides comprise 2' fluoro, and all purine nucleosides comprise 2'-O-methyl, with the proviso that the sense strand may include a 2' deoxy nucleoside. In some embodiments, the sense strand includes the 2' deoxy nucleoside. In some embodiments, the sense strand does not include the 2' deoxy nucleoside. Some embodiments include a proviso that the sense strand may include a 2'-O-methoxyethyl nucleoside (e.g. at position 4, counting from 5' to 3'). Some embodiments include the 2'-O-methoxyethyl nucleoside in the sense strand. Some embodiments do not include the 2'-O-methoxyethyl nucleoside in the sense strand.

In some embodiments, any one of the following is true with regard to the sense strand: all purine nucleosides comprise 2' fluoro, and all pyrimidine nucleosides are modified with a mixture of 2' fluoro and 2'-O-methyl, all purine nucleosides comprise 2'-O-methyl, and all pyrimidine nucleosides are modified with a mixture of 2' fluoro and 2'-O-methyl, all purine nucleosides comprise 2' fluoro, and all pyrimidine nucleosides comprise 2'-O-methyl, all pyrimidine nucleosides comprise 2' fluoro, and all purine nucleosides are modified with a mixture of 2' fluoro and 2'-O-methyl, all pyrimidine nucleosides comprise 2'-O-methyl, and all purine nucleosides are modified with a mixture of 2' fluoro and 2'-O-methyl, or all pyrimidine nucleosides comprise 2' fluoro, and all purine nucleosides comprise 2'-O-methyl. In some embodiments, in the sense strand, all purine nucleosides comprise 2' fluoro, and all pyrimidine nucleosides are modified with a mixture of 2' fluoro and 2'-O-methyl. In some embodiments, in the sense strand, all purine nucleosides comprise 2'-O-methyl, and all pyrimidine nucleosides are modified with a mixture of 2' fluoro and 2'-O-methyl. In some embodiments, in the sense strand, all purine nucleosides comprise 2' fluoro, and all pyrimidine nucleosides comprise 2'-O-methyl. In some embodiments, in the sense strand, all pyrimidine nucleosides comprise 2' fluoro, and all purine nucleosides are modified with a mixture of 2' fluoro and 2'-O-methyl. In some embodiments, in the sense strand, all pyrimidine nucleosides comprise 2'-O-methyl, and all purine nucleosides are modified with a mixture of 2' fluoro and 2'-O-methyl. In some embodiments, in the sense strand, all pyrimidine nucleosides comprise 2' fluoro, and all purine nucleosides comprise 2'-O-methyl. Some embodiments include a proviso that the sense strand may include a 2'-O-methoxyethyl nucleoside (e.g. at position 4, counting from 5' to 3'). Some embodiments include the 2'-O-methoxyethyl nucleoside in the sense strand. Some embodiments do not include the 2'-O-methoxyethyl nucleoside in the sense strand.

In some embodiments, any one of the following is true with regard to the antisense strand, with the proviso that the antisense strand may include a 2' deoxy nucleoside: all purine nucleosides comprise 2' fluoro, and all pyrimidine nucleosides are modified with a mixture of 2' fluoro and 2'-O-methyl, all purine nucleosides comprise 2'-O-methyl, and all pyrimidine nucleosides are modified with a mixture of 2' fluoro and 2'-O-methyl, all purine nucleosides comprise 2'-O-methyl, and all pyrimidine nucleosides comprise 2' fluoro, all pyrimidine nucleosides comprise 2' fluoro, and all purine nucleosides are modified with a mixture of 2' fluoro and 2'-O-methyl, all pyrimidine nucleosides comprise 2'-O-methyl, and all purine nucleosides are modified with a mixture of 2' fluoro and 2'-O-methyl, or all pyrimidine nucleosides comprise 2'-O-methyl, and all purine nucleosides comprise 2' fluoro. In some embodiments, in the antisense strand, all purine nucleosides comprise 2' fluoro, and all pyrimidine nucleosides are modified with a mixture of 2' fluoro and 2'-O-methyl, with the proviso that the antisense strand may include a 2' deoxy nucleoside. In some embodiments, in the antisense strand, all purine nucleosides comprise 2'-O-methyl, and all pyrimidine nucleosides are modified with a mixture of 2' fluoro and 2'-O-methyl, with the proviso that the antisense strand may include a 2' deoxy nucleoside. In some embodiments, in the antisense strand, all purine nucleosides comprise 2' fluoro, and all pyrimidine nucleosides comprise 2'-O-methyl, with the proviso that the antisense strand may include a 2' deoxy nucleoside. In some embodiments, in the antisense strand, all pyrimidine nucleosides comprise 2' fluoro, and all purine nucleosides are modified with a mixture of 2' fluoro and 2'-O-methyl, with the proviso that the antisense strand may include a 2' deoxy nucleoside. In some embodiments, in the antisense strand, all pyrimidine nucleosides comprise 2'-O-methyl, and all purine nucleosides are modified with a mixture of 2' fluoro and 2'-O-methyl, with the proviso that the antisense strand may include a 2' deoxy nucleoside. In some embodiments, in the antisense strand, all pyrimidine nucleosides comprise 2' fluoro, and all purine nucleosides comprise 2'-O-methyl, with the proviso that the antisense strand may include a 2' deoxy nucleoside. In some embodiments, the antisense strand includes the 2' deoxy nucleoside. In some embodiments, the antisense strand does not include the 2' deoxy nucleoside. Some embodiments include a proviso that the antisense strand may include a 2'-O-methoxyethyl nucleoside (e.g. at position 4, counting from 5' to 3'). Some embodiments include the 2'-O-methoxyethyl nucleoside in the antisense strand. Some embodiments do not include the 2'-O-methoxyethyl nucleoside in the antisense strand.

In some embodiments, any one of the following is true with regard to the antisense strand: all purine nucleosides comprise 2' fluoro, and all pyrimidine nucleosides are modified with a mixture of 2' fluoro and 2'-O-methyl, all purine nucleosides comprise 2'-O-methyl, and all pyrimidine nucleosides are modified with a mixture of 2' fluoro and 2'-O-methyl, all purine nucleosides comprise 2'-O-methyl, and all pyrimidine nucleosides comprise 2' fluoro, all pyrimidine nucleosides comprise 2' fluoro, and all purine nucleosides are modified with a mixture of 2' fluoro and 2'-O-methyl, all pyrimidine nucleosides comprise 2'-O-methyl, and all purine nucleosides are modified with a mixture of 2' fluoro and 2'-O-methyl, or all pyrimidine nucleosides comprise 2'-O-methyl, and all purine nucleosides comprise 2' fluoro. In some embodiments, in the antisense strand, all purine nucleosides comprise 2' fluoro, and all pyrimidine nucleosides are modified with a mixture of 2' fluoro and 2'-O-methyl. In some embodiments, in the antisense strand, all purine nucleosides comprise 2'-O-methyl, and all pyrimidine nucleosides are modified with a mixture of 2' fluoro and 2'-O-methyl. In some embodiments, in the antisense strand, all purine nucleosides comprise 2' fluoro, and all pyrimidine nucleosides comprise 2'-O-methyl. In some embodiments, in the antisense strand, all pyrimidine nucleosides comprise 2' fluoro, and all purine nucleosides are modified with a mixture of 2' fluoro and 2'-O-methyl. In some embodiments, in the antisense strand, all pyrimidine nucleosides comprise 2'-O-methyl, and all purine nucleosides are modified with a mixture of 2' fluoro and 2'-O-methyl. In some embodiments, in the antisense strand, all pyrimidine nucleosides comprise 2' fluoro, and all purine nucleosides comprise 2'-O-methyl. Some embodiments include a proviso that the antisense strand may include a 2'-O-methoxyethyl nucleoside (e.g. at position 4, counting from 5' to 3'). Some embodiments include the 2'-O-methoxyethyl nucleoside in the antisense strand. Some embodiments do not include the 2'-O-methoxyethyl nucleoside in the antisense strand.

In some embodiments, the antisense strand comprises one or two 3' phosphorothioate linkages. For example, there may be a phosphorothioate linkage between the first and second nucleotides from the 3' end of the antisense strand, or there may be phosphorothioate linkages between the first, second and third nucleotides from the 3' end of the antisense strand. In some embodiments, the sense strand comprises one or two 5' phosphorothioate linkages. For example, there may be a phosphorothioate linkage between the first and second nucleotides from the 5' end of the sense strand, or there may be phosphorothioate linkages between the first, second and third nucleotides from the 5' end of the sense strand. In some embodiments, the sense strand does not comprise one or two 5' phosphorothioate linkages. For example, in some embodiments, there are no phosphorothioate linkages between the last 3 nucleotides at the 5' end of the sense strand. In some embodiments, the sense strand comprises 5' phosphate linkages. In some embodiments, the sense strand comprises one or two 3' phosphorothioate linkages. For example, there may be a phosphorothioate linkage between the first and second nucleotides from the 3' end of the sense strand, or there may be phosphorothioate linkages between the first, second and third nucleotides from the 3' end of the sense strand.

In some embodiments, the antisense strand comprises a 5' end comprising 2 phosphorothioate linkages. The 5' end may comprise 3 nucleosides separated by the 2 phosphorothioate linkages. In some embodiments, the antisense strand comprises a 3' end comprising 2 phosphorothioate linkages. The 3' end may comprise 3 nucleosides separated by the 2 phosphorothioate linkages.

In some embodiments, the composition comprises an oligonucleotide that inhibits the expression of a target nucleic acid, wherein the oligonucleotide comprises an siRNA comprising a sense strand and an antisense strand, wherein the oligonucleotide comprises a hydrophobic moiety. In some embodiments, the hydrophobic moiety may be attached at the 5' end of the sense strand. In some embodiments, the hydrophobic moiety may be attached at the 3' end of the sense strand. In some embodiments, the hydrophobic moiety may be attached at the 5' end of the antisense strand. In some embodiments, the hydrophobic moiety may be attached at the 3' end of the antisense strand.

In some embodiments, the composition comprises an oligonucleotide that inhibits the expression of a target nucleic acid, wherein the oligonucleotide comprises an siRNA comprising a sense strand and an antisense strand, wherein the oligonucleotide comprises one or more vinyl phosphonate. In some embodiments, the one or more vinyl phosphonate may be attached at the 5' end of the sense strand. In some embodiments, the one or more vinyl phosphonate may be attached at the 3' end of the sense strand. In some embodiments, the one or more vinyl phosphonate may be attached at the 5' end of the antisense strand. In some embodiments, the one or more vinyl phosphonate may be attached at the 3' end of the antisense strand.

In some embodiments, the sense strand comprises or consists of RNA or modified RNA nucleotides. In some embodiments, the sense strand comprises a deoxy nucleoside. The deoxy nucleoside may include a DNA nucleoside. In some embodiments, the deoxy nucleoside comprises or consists of a 2' deoxy nucleoside. The deoxy nucleoside may be at a position within the sense strand (5' to 3', where the 5' position is 1). The position within the sense strand may be or include position 2, 4, 6, 8, 9, 10, 12, 14, 16, or 18, or a combination of said positions. The position within the sense strand may be or include position 2, 4, 6, 8, 10, 12, 14, 16, or 18, or a combination of said positions. The position within the sense strand may be or include position 2, 6, 9, 10, 14, or 18, or a combination of said positions. The position within the sense strand may be or include position 2, 6, 10, 14, or 18, or a combination of said positions. The position within the sense strand may be or include position 4, 8, 9, 12, or 16, or a combination of said positions. The position within the sense strand may be or include position 4, 8, 12, or 16, or a combination of said positions. The position within the sense strand may include position 9. The position within the sense strand may be position 9. The sense strand may include 1, 2, 3, 4, 5, 6, 7, 8, 9, 10, 11, 12, 13, 14, 15, 16, 17, 18, or 19 deoxy nucleosides. In some embodiments, the sense strand includes 1 deoxy nucleoside. The sense strand may include 1, 2, 3, 4, 5, 6, 7, 8, 9, 10, 11, 12, 13, 14, 15, 16, 17, 18, or 19 deoxy nucleosides, or a range of deoxy nucleosides defined by any two of the aforementioned numbers of deoxy nucleosides. The sense strand may include deoxy nucleosides at all even positions. The sense strand may include deoxy nucleosides at some even positions. The sense strand may include deoxy nucleosides at every other even position. The sense strand may include 1 deoxy nucleoside. The sense strand may include at least 1 deoxy nucleoside. The sense strand may include at least 2 deoxy nucleosides. The sense strand may include at least 3 deoxy nucleosides. The sense strand may include at least 4 deoxy nucleosides. The sense strand may include at least 5 deoxy nucleosides. The sense strand may include at least 6 deoxy nucleosides. The sense strand may include at least 7 deoxy nucleosides. The sense strand may include at least 8 deoxy nucleosides. The sense strand may include at least 9 deoxy nucleosides. The sense strand may include at least 10 deoxy nucleosides. The sense strand may include no greater than 2 deoxy nucleosides. The sense strand may include no greater than 3 deoxy nucleosides. The sense strand may include no greater than 4 deoxy nucleosides. The sense strand may include no greater than 5 deoxy nucleosides. The sense strand may include no greater than 6 deoxy nucleosides. The sense strand may include no greater than 7 deoxy nucleosides. The sense strand may include no greater than 8 deoxy nucleosides. The sense strand may include no greater than 9 deoxy nucleosides. The sense strand may include no greater than 10 deoxy nucleosides.

In some embodiments, the antisense strand comprises or consists of RNA or modified RNA nucleotides. In some embodiments, the antisense strand comprises a deoxy nucleoside. The deoxy nucleoside may include a DNA nucleoside. In some embodiments, the deoxy nucleoside comprises or consists of a 2' deoxy nucleoside. The antisense strand may include 1, 2, 3, 4, 5, 6, 7, 8, 9, 10, 11, 12, 13, 14, 15, 16, 17, 18, or 19 deoxy nucleosides, or a range of deoxy nucleosides defined by any two of the aforementioned numbers of deoxy nucleosides.

In some embodiments in which a deoxy nucleoside is included in the sense strand (e.g. at the 9th nucleotide counting from 5' end), nucleosides at positions 1-8 include a mixture of 2' fluoro and 2'-O-methyl modified nucleosides. In some embodiments in which a deoxy nucleoside is included in the sense strand, purines at positions 1-8 include a mixture of 2' fluoro and 2'-O-methyl modified nucleosides. In some embodiments in which a deoxy nucleoside is included in the sense strand, pyrimidines at positions 1-8 include a mixture of 2' fluoro and 2'-O-methyl modified nucleosides. In some embodiments in which a deoxy nucleoside is included in the sense strand, nucleosides at positions 1-8 all include 2'-O-methyl modified nucleosides. In some embodiments in which a deoxy nucleoside is included in the sense strand, purines at positions 1-8 all include 2'-O-methyl modified nucleosides. In some embodiments in which a deoxy nucleoside is included in the sense strand, pyrimidines at positions 1-8 all include 2'-O-methyl modified nucleosides. In some embodiments in which a deoxy nucleoside is included in the sense strand, purines at positions 1-8 include a mixture of 2' fluoro and 2'-O-methyl modified nucleosides, and pyrimidines at positions 1-8 all include 2'-O-methyl modified nucleosides. In some embodiments in which a deoxy nucleoside is included in the sense strand, pyrimidines at positions 1-8 include a mixture of 2' fluoro and 2'-O-methyl modified nucleosides, and purines at positions 1-8 all include 2'-O-methyl modified nucleosides.

An antisense strand may start with an alternating pattern wherein the even numbered nucleosides include 2' fluoro modified nucleosides, and odd numbered nucleosides include 2'-O-methyl modified nucleosides. The sense strand may then be optimized by replacing some 2' fluoro modifications with 2'-O-methyl modifications. The antisense strand may include a mixture of 2' fluoro modifications and 2'-O-methyl modifications.

2. Modified ASOs

In some embodiments, the composition comprises an oligonucleotide that inhibits the expression of a target nucleic acid, wherein the oligonucleotide comprises an antisense oligonucleotide (ASO). In some embodiments, the ASO comprises modification pattern 1S, 2S, 3S, 4S, 1AS, or 2AS, or any other combination of modifications described herein. In some embodiments, the ASO comprises modification pattern 1S, 2S, 3S, 4S, 5S, 6S, 7S, 8S, 9S, 10S, 11S, 12S, 13S, 14S, 15S, 16S, 17S, 18S, 19S, 20S, 21S, 22S, 23S, 24S, 25S, 26S, 27S, 28S, 29S, 30S, 1AS, 2AS, 3AS, 4AS, or 5A5.

D. Formulations

In some embodiments, the composition is a pharmaceutical composition. In some embodiments, the composition is sterile. In some embodiments, the composition further comprises a pharmaceutically acceptable carrier.

In some embodiments, the pharmaceutically acceptable carrier comprises water. In some embodiments, the pharmaceutically acceptable carrier comprises a buffer. In some embodiments, the pharmaceutically acceptable carrier comprises a saline solution. In some embodiments, the pharmaceutically acceptable carrier comprises water, a buffer, or a saline solution. In some embodiments, the composition comprises a liposome. In some embodiments, the pharmaceutically acceptable carrier comprises liposomes, lipids, nanoparticles, proteins, protein-antibody complexes, peptides, cellulose, nanogel, or a combination thereof In some embodiments, the composition is formulated to cross the blood brain barrier. In some embodiments, the composition is formulated for central nervous system (CNS) delivery. In some embodiments, the composition includes a lipophilic compound. The lipophilic compound may be useful for crossing the blood brain barrier or for CNS delivery.

In some embodiments, the composition is formulated for administration. The administration may be systemic. In some embodiments, the administration is intravenous. In some embodiments, the administration is by injection. In some embodiments, the injection is subcutaneous. In some embodiments, the injection is subcutaneous. In some embodiments, the injection is intraperitoneal. In some embodiments, the injection is intramuscular. In some embodiments, the injection is intrathecal. The administration may be to an eye (e.g. intravitreal). The administration may be to a neural tissue. The administration may be to a brain. The administration may be intracerebroventricular. The administration may be intrathecal. The administration may be to a spinal cord or a spinal canal. In some embodiments, the formulation allows for delivery of a compound such as an oligonucleotide to an eye cell. In some embodiments, the formulation allows for delivery of a compound such as an oligonucleotide to a neural cell.

E. Kits

Described herein, in some embodiments, are kits. The kit may include an oligonucleotide such as an siRNA described herein. The oligonucleotide may be conjugated to a lipid moiety. The kit may include a lipid moiety described herein. The oligonucleotide may comprise nucleoside modifications or modified internucleoside linkages. The oligonucleotide may include any modifications described herein, such as modifications from a base sequence. The kit may include a delivery reagent such as a needle. The kit may include instructions for use, such as methods for use in a method described herein.

II. METHODS AND USES

Disclosed herein, in some embodiments, are methods of administering a composition described herein to a subject. Some embodiments relate to use a composition described herein, such as administering the composition to a subject.

Some embodiments relate to a method of treating a disorder in a subject in need thereof. Some embodiments relate to use of a composition described herein in the method of treatment. Some embodiments include administering a composition described herein to a subject with the disorder. In some embodiments, the administration treats the disorder in the subject. In some embodiments, the composition treats the disorder in the subject.

In some embodiments, the treatment comprises prevention, inhibition, or reversion of the disorder in the subject. Some embodiments relate to use of a composition described herein in the method of preventing, inhibiting, or reversing the disorder. Some embodiments relate to a method of preventing, inhibiting, or reversing a disorder a disorder in a subject in need thereof. Some embodiments include administering a composition described herein to a subject with the disorder. In some embodiments, the administration prevents, inhibits, or reverses the disorder in the subject. In some embodiments, the composition prevents, inhibits, or reverses the disorder in the subject.

Some embodiments relate to a method of preventing a disorder a disorder in a subject in need thereof. Some embodiments relate to use of a composition described herein in the method of preventing the disorder. Some embodiments include administering a composition described herein to a subject with the disorder. In some embodiments, the administration prevents the disorder in the subject. In some embodiments, the composition prevents the disorder in the subject.

Some embodiments relate to a method of inhibiting a disorder a disorder in a subject in need thereof. Some embodiments relate to use of a composition described herein in the method of inhibiting the disorder. Some embodiments include administering a composition described herein to a subject with the disorder. In some embodiments, the administration inhibits the disorder in the subject. In some embodiments, the composition inhibits the disorder in the subject.

Some embodiments relate to a method of reversing a disorder a disorder in a subject in need thereof. Some embodiments relate to use of a composition described herein in the method of reversing the disorder. Some embodiments include administering a composition described herein to a subject with the disorder. In some embodiments, the administration reverses the disorder in the subject. In some embodiments, the composition reverses the disorder in the subject.

In some embodiments, the administration is systemic. In some embodiments, the administration is intravenous. In some embodiments, the administration is by injection. In some embodiments, the injection is subcutaneous. In some embodiments, the injection is subcutaneous. In some embodiments, the injection is intraperitoneal. In some embodiments, the injection is intramuscular. The administration may be to an eye (e.g. intravitreal). The administration may be to a neural tissue. The administration may be to a brain. The administration may be intracerebroventricular. In some embodiments, the injection is intrathecal. The administration may be intrathecal. The administration may be to the spinal cord or the spinal canal.

Disclosed herein, in some embodiments, are methods of targeting an siRNA to a cell or tissue. The method may include conjugating the siRNA (e.g. the sense strand of the siRNA) to a lipid moiety described herein. The method may comprise delivering the siRNA conjugated to the lipid moiety to the tissue or cell. The method may comprise contacting the tissue or cell with the siRNA conjugated to the lipid moiety.

Disclosed herein, in some embodiments, are methods of reducing an amount of a target RNA or protein in a cell or tissue, comprising administering or delivering a composition described herein the cell or tissue. The composition may include an siRNA with an antisense strand that has a sequence complementary to the RNA. The antisense strand may bind to the RNA.

Disclosed herein, in some embodiments, are methods of making an siRNA composition. The method may include conjugating an siRNA to a lipid moiety. The siRNA and lipid moiety may include any siRNA or lipid moiety described herein. The method may include synthesizing the siRNA. The method may include synthesizing the lipid moiety.

A. Disorders

Some embodiments of the methods described herein include treating a disorder in a subject in need thereof. In some embodiments, the disorder is an ocular disorder. In some embodiments, the disorder is an adipose-related disorder. In some embodiments, the disorder is a kidney disorder. In some embodiments, the disorder is a brain disorder. In some embodiments, the disorder is a vascular disorder. In some embodiments, the disorder is a muscle disorder. In some embodiments, the disorder is a lung disorder.

B. Subjects

Some embodiments of the methods described herein include treatment of a subject. Non-limiting examples of subjects include vertebrates, animals, mammals, dogs, cats, cattle, rodents, mice, rats, primates, monkeys, and humans. In some embodiments, the subject is a vertebrate. In some embodiments, the subject is an animal. In some embodiments, the subject is a mammal. In some embodiments, the subject is a dog. In some embodiments, the subject is a cat. In some embodiments, the subject is a cattle. In some embodiments, the subject is a mouse. In some embodiments, the subject is a rat. In some embodiments, the subject is a primate. In some embodiments, the subject is a monkey. In some embodiments, the subject is an animal, a mammal, a dog, a cat, cattle, a rodent, a mouse, a rat, a primate, or a monkey. In some embodiments, the subject is a human.

In some embodiments, the subject is male. In some embodiments, the subject is female. In some embodiments, the subject is an adult (e.g. at least 18 years old).

C. Baseline Measurements

Some embodiments of the methods described herein include obtaining a baseline measurement from a subject. For example, in some embodiments, a baseline measurement is obtained from the subject prior to treating the subject.

In some embodiments, the baseline measurement is obtained directly from the subject. In some embodiments, the baseline measurement is obtained by observation, for example by observation of the subject or of the subject's tissue. In some embodiments, the baseline measurement is obtained noninvasively using an imaging device.

In some embodiments, the baseline measurement is obtained in a sample from the subject. In some embodiments, the baseline measurement is obtained in one or more histological tissue sections. In some embodiments, the baseline measurement is obtained by performing an assay such as an immunoassay, a colorimetric assay, or a fluorescence assay, on the sample obtained from the subject. In some embodiments, the baseline measurement is obtained by an immunoassay, a colorimetric assay, a fluorescence assay, or a chromatography (e.g. HPLC) assay. In some embodiments, the baseline measurement is obtained by PCR.

In some embodiments, the baseline measurement is a baseline target protein measurement. In some embodiments, the baseline target protein measurement comprises a baseline target protein level. In some embodiments, the baseline target protein level is indicated as a mass or percentage of target protein per sample weight. In some embodiments, the baseline target protein level is indicated as a mass or percentage of target protein per sample volume. In some embodiments, the baseline target protein level is indicated as a mass or percentage of target protein per total protein within the sample. In some embodiments, the baseline target protein measurement is a baseline circulating/tissue target protein measurement. In some embodiments, the baseline target protein measurement is obtained by an assay such as an immunoassay, a colorimetric assay, or a fluorescence assay.

In some embodiments, the baseline measurement is a baseline target mRNA measurement. In some embodiments, the baseline target mRNA measurement comprises a baseline target mRNA level. In some embodiments, the baseline target mRNA level is indicated as an amount or percentage of target mRNA per sample weight. In some embodiments, the baseline target mRNA level is indicated as an amount or percentage of target mRNA per sample volume. In some embodiments, the baseline target mRNA level is indicated as an amount or percentage of target mRNA per total mRNA within the sample. In some embodiments, the baseline target mRNA level is indicated as an amount or percentage of target mRNA per total nucleic acids within the sample. In some embodiments, the baseline target mRNA level is indicated relative to another mRNA level, such as an mRNA level of a housekeeping gene, within the sample. In some embodiments, the baseline target mRNA measurement is a baseline tissue target mRNA measurement. In some embodiments, the baseline target mRNA measurement is obtained by an assay such as a polymerase chain reaction (PCR) assay. In some embodiments, the PCR comprises quantitative PCR (qPCR). In some embodiments, the PCR comprises reverse transcription of the target mRNA.

Some embodiments of the methods described herein include obtaining a sample from a subject. In some embodiments, the baseline measurement is obtained in a sample obtained from the subject. In some embodiments, the sample is obtained from the subject prior to administration or treatment of the subject with a composition described herein. In some embodiments, a baseline measurement is obtained in a sample obtained from the subject prior to administering the composition to the subject. In some embodiments, the sample is obtained from the subject in a fasted state. In some embodiments, the sample is obtained from the subject after an overnight fasting period. In some embodiments, the sample is obtained from the subject in a fed state.

In some embodiments, the sample comprises a fluid. In some embodiments, the sample is a fluid sample. In some embodiments, the sample is a blood, plasma, or serum sample. In some embodiments, the sample comprises blood. In some embodiments, the sample is a blood sample. In some embodiments, the sample is a whole-blood sample. In some embodiments, the blood is fractionated or centrifuged. In some embodiments, the sample comprises plasma. In some embodiments, the sample is a plasma sample. A blood sample may be a plasma sample. In some embodiments, the sample comprises serum. In some embodiments, the sample is a serum sample. A blood sample may be a serum sample. In some embodiments, the fluid comprises cerebrospinal fluid (CSF). For example, the fluid may be obtained by a spinal tap. In some embodiments, the fluid comprises spinal fluid. In some embodiments, the fluid comprises cerebral fluid. In some embodiments, the fluid comprises cerebral fluid.

In some embodiments, the sample comprises a tissue. In some embodiments, the sample is a tissue sample. In some embodiments, the tissue comprises eye, kidney, muscle, adipose, brain, lung, or vascular tissue. For example, the baseline target mRNA measurement, or the baseline target protein measurement, may be obtained in a kidney, adipose, brain, lung, or vascular sample obtained from the patient. In some embodiments, the tissue comprises kidney tissue. The kidney tissue may include renal medullary cells, or renal proximal tubule cells. In some embodiments, the tissue comprises adipose tissue. In some embodiments, the adipose tissue comprises white adipose tissue. The adipose tissue may include adipocytes. In some embodiments, the tissue comprises liver tissue. The liver may include hepatocytes. In some embodiments, the tissue is non-liver tissue. In some embodiments, the tissue comprises eye tissue. In some embodiments, the eye tissue comprises retinal tissue. In some embodiments, the tissue comprises brain tissue. The brain tissue may include neurons or glial cells. The brain tissue may comprise cerebellum. The brain tissue may comprise frontal cortex. The brain tissue may comprise temporal cortex. The brain tissue may comprise tissue from the right hemisphere of the brain (e.g. right frontal cortex or right temporal cortex). The brain tissue may comprise tissue from the left hemisphere of the brain (e.g. left frontal cortex or left temporal cortex). The brain tissue may comprise hippocampal tissue. In some embodiments, the tissue comprises nerve tissue. In some embodiments, the tissue comprises a nerve. In some embodiments, the tissue comprises spinal tissue. In some embodiments, the tissue comprises tissue of the spinal cord or spinal canal. In some embodiments, the tissue comprises lung tissue. In some embodiments, the tissue comprises vascular tissue. The vascular tissue may include vascular endothelial cells.

In some embodiments, the sample includes cells. In some embodiments, the sample comprises a cell. In some embodiments, the cell comprises an eye cell, a renal cell, muscle cell, an adipose cell, a brain cell, or a vasculature cell. In some embodiments, the cell is a renal cell. In some embodiments, the renal cell is a renal medullary cell. In some embodiments, the renal cell is a renal proximal tubule cell. In some embodiments, the cell is an adipose cell. In some embodiments, the adipose cell is an adipocyte. In some embodiments, the cell is a liver cell. In some embodiments, the liver cell is a hepatocyte. In some embodiments, the cell is a non-liver cell, or is not a hepatocyte. In some embodiments, the cell is an eye cell. In some embodiments, the eye cell is a retinal cell. In some embodiments, the eye cell is a rod cell. In some embodiments, the eye cell is a cone cell. In some embodiments, the cell is a brain cell. In some embodiments, the brain cell is from a brain tissue such as cerebellum, cortex, hippocampal tissue. In some embodiments, the brain cell is a neuron. In some embodiments, the brain cell is a glial cell. In some embodiments, the cell is a spinal cell. In some embodiments, the cell is a spinal cord cell. In some embodiments, the cell is a lung cell. In some embodiments, the cell is a vasculature cell. In some embodiments, the vasculature cell is an endothelial cell.

D. Effects

In some embodiments, the composition or administration of the composition affects a measurement such as a target protein measurement or a target mRNA measurement, relative to the baseline measurement.

Some embodiments of the methods described herein include obtaining the measurement from a subject. For example, the measurement may be obtained from the subject after treating the subject. In some embodiments, the measurement is obtained in a second sample (such as a fluid or tissue sample described herein) obtained from the subject after the composition is administered to the subject. In some embodiments, the measurement is an indication that the disorder has been treated.

In some embodiments, the measurement is obtained directly from the subject. In some embodiments, the measurement is obtained noninvasively using an imaging device. In some embodiments, the measurement is obtained in a second sample from the subject. In some embodiments, the measurement is obtained in one or more histological tissue sections. In some embodiments, the measurement is obtained by performing an assay on the second sample obtained from the subject. In some embodiments, the measurement is obtained by an assay, such as an assay described herein. In some embodiments, the assay is an immunoassay, a colorimetric assay, a fluorescence assay, a chromatography (e.g. HPLC) assay, or a PCR assay. In some embodiments, the measurement is obtained by an assay such as an immunoassay, a colorimetric assay, a fluorescence assay, or a chromatography (e.g. HPLC) assay. In some embodiments, the measurement is obtained by PCR. In some embodiments, the measurement is obtained by histology. In some embodiments, the measurement is obtained by observation. In some embodiments, additional measurements are made, such as in a 3rd sample, a 4th sample, or a fifth sample.

In some embodiments, the measurement is obtained within 1 hour, within 2 hours, within 3 hours, within 4 hours, within 5 hours, within 6 hours, within 12 hours, within 18 hours, or within 24 hours after the administration of the composition. In some embodiments, the measurement is obtained within 1 day, within 2 days, within 3 days, within 4 days, within 5 days, within 6 days, or within 7 days after the administration of the composition. In some embodiments, the measurement is obtained within 1 week, within 2 weeks, within 3 weeks, within 1 month, within 2 months, within 3 months, within 6 months, within 1 year, within 2 years, within 3 years, within 4 years, or within 5 years after the administration of the composition. In some embodiments, the measurement is obtained after 1 hour, after 2 hours, after 3 hours, after 4 hours, after 5 hours, after 6 hours, after 12 hours, after 18 hours, or after 24 hours after the administration of the composition. In some embodiments, the measurement is obtained after 1 day, after 2 days, after 3 days, after 4 days, after 5 days, after 6 days, or after 7 days after the administration of the composition. In some embodiments, the measurement is obtained after 1 week, after 2 weeks, after 3 weeks, after 1 month, after 2 months, after 3 months, after 6 months, after 1 year, after 2 years, after 3 years, after 4 years, or after 5 years, following the administration of the composition.

In some embodiments, the composition reduces the measurement relative to the baseline measurement. In some embodiments, the reduction is measured in a second sample obtained from the subject after administering the composition to the subject. In some embodiments, the reduction is measured directly in the subject after administering the composition to the subject. In some embodiments, the measurement is decreased by about 2.5% or more, about 5% or more, or about 7.5% or more, relative to the baseline measurement. In some embodiments, the measurement is decreased by about 10% or more, relative to the baseline measurement. In some embodiments, the measurement is decreased by about 20% or more, about 30% or more, about 40% or more, about 50% or more, about 60% or more, about 70% or more, about 80% or more, about 90% or more, relative to the baseline measurement. In some embodiments, the measurement is decreased by no more than about 2.5%, no more than about 5%, or no more than about 7.5%, relative to the baseline measurement. In some embodiments, the measurement is decreased by no more than about 10%, relative to the baseline measurement. In some embodiments, the measurement is decreased by no more than about 20%, no more than about 30%, no more than about 40%, no more than about 50%, no more than about 60%, no more than about 70%, no more than about 80%, no more than about 90%, or no more than about 100% relative to the baseline measurement. In some embodiments, the measurement is decreased by 2.5%, 5%, 7.5%, 10%, 20%, 30%, 40%, 50%, 60%, 70%, 80%, 90%, or 100%, or by a range defined by any of the two aforementioned percentages.

In some embodiments, the composition increases the measurement relative to the baseline measurement. In some embodiments, the increase is measured in a second sample obtained from the subject after administering the composition to the subject. In some embodiments, the increase is measured directly in the subject after administering the composition to the subject. In some embodiments, the measurement is increased by about 2.5% or more, about 5% or more, or about 7.5% or more, relative to the baseline measurement. In some embodiments, the measurement is increased by about 10% or more, relative to the baseline measurement. In some embodiments, the measurement is increased by about 20% or more, about 30% or more, about 40% or more, about 50% or more, about 60% or more, about 70% or more, about 80% or more, about 90% or more, relative to the baseline measurement. In some embodiments, the measurement is increased by about 100% or more, increased by about 250% or more, increased by about 500% or more, increased by about 750% or more, or increased by about 1000% or more, relative to the baseline measurement. In some embodiments, the measurement is increased by no more than about 2.5%, no more than about 5%, or no more than about 7.5%, relative to the baseline measurement. In some embodiments, the measurement is increased by no more than about 10%, relative to the baseline measurement. In some embodiments, the measurement is increased by no more than about 20%, no more than about 30%, no more than about 40%, no more than about 50%, no more than about 60%, no more than about 70%, no more than about 80%, no more than about 90%, or no more than about 100% relative to the baseline measurement. In some embodiments, the measurement is increased by no more than about 100%, increased by no more than about 250%, increased by no more than about 500%, increased by no more than about 750%, or increased by no more than about 1000%, relative to the baseline measurement. In some embodiments, the measurement is increased by 2.5%, 5%, 7.5%, 10%, 20%, 30%, 40%, 50%, 60%, 70%, 80%, 90%, 100%, 250%, 500%, 750%, or 1000%, or by a range defined by any of the two aforementioned percentages.

In some embodiments, the measurement is an target protein measurement. In some embodiments, the target protein measurement comprises an target protein level. In some embodiments, the target protein level is indicated as a mass or percentage of target protein per sample weight. In some embodiments, the target protein level is indicated as a mass or percentage of target protein per sample volume. In some embodiments, the target protein level is indicated as a mass or percentage of target protein per total protein within the sample. In some embodiments, the target protein measurement is a circulating/tissue target protein measurement. In some embodiments, the target protein measurement is obtained by an assay such as an immunoassay, a colorimetric assay, or a fluorescence assay.

In some embodiments, the composition reduces the target protein measurement relative to the baseline target protein measurement. In some embodiments, the composition reduces circulating target protein levels relative to the baseline target protein measurement. In some embodiments, the composition reduces tissue target protein levels relative to the baseline target protein measurement. In some embodiments, the reduced target protein levels are measured in a second sample obtained from the subject after administering the composition to the subject. In some embodiments, the target protein measurement is decreased by about 2.5% or more, about 5% or more, or about 7.5% or more, relative to the baseline target protein measurement. In some embodiments, the target protein measurement is decreased by about 10% or more, relative to the baseline target protein measurement. In some embodiments, the target protein measurement is decreased by about 20% or more, about 30% or more, about 40% or more, about 50% or more, about 60% or more, about 70% or more, about 80% or more, about 90% or more, or about 100%, relative to the baseline target protein measurement. In some embodiments, the target protein measurement is decreased by no more than about 2.5%, no more than about 5%, or no more than about 7.5%, relative to the baseline target protein measurement. In some embodiments, the target protein measurement is decreased by no more than about 10%, relative to the baseline target protein measurement. In some embodiments, the target protein measurement is decreased by no more than about 20%, no more than about 30%, no more than about 40%, no more than about 50%, no more than about 60%, no more than about 70%, no more than about 80%, no more than about 90%, or no more than about 100% relative to the baseline target protein measurement. In some embodiments, the target protein measurement is decreased by 2.5%, 5%, 7.5%, 19%, 20%, 30%, 40%, 50%, 60%, 70%, 80%, 90%, or 100%, or by a range defined by any of the two aforementioned percentages.

In some embodiments, the measurement is an target mRNA measurement. In some embodiments, the target mRNA measurement comprises an target mRNA level. In some embodiments, the target mRNA level is indicated as an amount or percentage of target mRNA per sample weight. In some embodiments, the target mRNA level is indicated as an amount or percentage of target mRNA per sample volume. In some embodiments, the target mRNA level is indicated as an amount or percentage of target mRNA per total mRNA within the sample. In some embodiments, the target mRNA level is indicated as an amount or percentage of target mRNA per total nucleic acids within the sample. In some embodiments, the target mRNA level is indicated relative to another mRNA level, such as an mRNA level of a housekeeping gene, within the sample. In some embodiments, the target mRNA measurement is a circulating/tissue target mRNA measurement. In some embodiments, the target mRNA measurement is obtained by an assay such as a PCR assay. In some embodiments, the PCR comprises qPCR. In some embodiments, the PCR comprises reverse transcription of the target mRNA.

In some embodiments, the composition reduces the target mRNA measurement relative to the baseline target mRNA measurement. In some embodiments, the target mRNA measurement is obtained in a second sample obtained from the subject after administering the composition to the subject. In some embodiments, the composition reduces target mRNA levels relative to the baseline target mRNA levels. In some embodiments, the reduced target mRNA levels are measured in a second sample obtained from the subject after administering the composition to the subject. In some embodiments, the second sample is a liver sample. In some embodiments, the second sample is an adipose sample. In some embodiments, the target mRNA measurement is reduced by about 2.5% or more, about 5% or more, or about 7.5% or more, relative to the baseline target mRNA measurement. In some embodiments, the target mRNA measurement is decreased by about 10% or more, relative to the baseline target mRNA measurement. In some embodiments, the target mRNA measurement is decreased by about 20% or more, about 30% or more, about 40% or more, about 50% or more, about 60% or more, about 70% or more, about 80% or more, about 90% or more, or about 100%, relative to the baseline target mRNA measurement. In some embodiments, the target mRNA measurement is decreased by no more than about 2.5%, no more than about 5%, or no more than about 7.5%, relative to the baseline target mRNA measurement. In some embodiments, the target mRNA measurement is decreased by no more than about 10%, relative to the baseline target mRNA measurement. In some embodiments, the target mRNA measurement is decreased by no more than about 20%, no more than about 30%, no more than about 40%, no more than about 50%, no more than about 60%, no more than about 70%, no more than about 80%, no more than about 90%, or no more than about 100%, relative to the baseline target mRNA measurement. In some embodiments, the target mRNA measurement is decreased by 2.5%, 5%, 7.5%, 10%, 20%, 30%, 40%, 50%, 60%, 70%, 80%, 90%, or 100% or by a range defined by any of the two aforementioned percentages.

III. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," and "patient" may be used interchangeably herein. A "subject" can be a biological entity containing expressed genetic materials. The biological entity can be a plant, animal, or microorganism, including, for example, bacteria, viruses, fungi, and protozoa. The subject can be a mammal. The mammal can be a human. The subject may be diagnosed or suspected of being at high risk for a disease. In some cases, the subject is not necessarily diagnosed or suspected of being at high risk for the disease.

As used herein, the term "about" a number refers to that number plus or minus 10% of that number. The term "about" a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

"Treatment" or "treating" may include an approach for obtaining beneficial or desired results with respect to a disease, disorder, or medical condition including but not limited to a therapeutic benefit and/or a prophylactic benefit. A therapeutic benefit can include, for example, the eradication or amelioration of the underlying disorder being treated. Also, a therapeutic benefit can include, for example, the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treatment via administration of a compound described herein does not require the involvement of a medical professional.

Some embodiments refer to nucleic acid sequence information. It is contemplated that in some embodiments, thymine (T) may be interchanged with uracil (U), or vice versa. For example, some sequences in the sequence listing may recite Ts, but these may be replaced with Us in some embodiments. In some oligonucleotides with nucleic acid sequences that include uracil, the uracil may be replaced with thymine. Similarly, in some oligonucleotides with nucleic acid sequences that include thymine, the thymine may be replaced with uracil. In some embodiments, an oligonucleotide such as an siRNA comprises or consists of RNA. In some embodiments, the oligonucleotide may include DNA. For example, the oligonucleotide may include 2' deoxyribonucleotides. An ASO may comprise or consist of DNA. To any extent that the sequence listing contradicts the disclosure in the specification, the specification takes precedent.

Some aspects include sequences with nucleotide modifications or modified internucleoside linkages. Generally, and unless otherwise specified, Nf (e.g. Af, Cf, Gf, Tf, or Uf) refers to a 2' fluoro-modified nucleoside, dN (e.g. dA, dC, dG, dT, or dU) refers to a 2' deoxy nucleoside, n (e.g. a, c, g, t, or u) refers to a 2' O-methyl modified nucleoside, and "s" refers to a phosphorothioate linkage.

A pyrimidine may include cytosine (C), thymine (T), or uracil (U). A pyrimidine may include C or U. A pyrimidine may include C or T. A reference to a pyrimidine may include a nucleoside or nucleotide comprising the pyrimidine. A purine may include guanine (G) or adenine (A). A reference to a purine may include a nucleoside or nucleotide comprising a purine.

The section headings used herein are for organizational purposes only and are not to be construed as limiting the subject matter described.

The term "$C_{x-y}$" or "$C_x$-$C_y$" when used in conjunction with a chemical moiety, such as alkyl, alkenyl, or alkynyl is meant to include groups that contain from x to y carbons in the chain. For example, the term "$C_{1-6}$alkyl" refers to substituted or unsubstituted saturated hydrocarbon groups, including straight-chain alkyl and branched-chain alkyl groups that contain from 1 to 6 carbons.

The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond, respectively.

The term "carbocycle" as used herein refers to a saturated, unsaturated or aromatic ring in which each atom of the ring is carbon. Carbocycle includes 3- to 10-membered monocyclic rings, 5- to 12-membered bicyclic rings, 5- to 12-membered spiro bicycles, and 5- to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle further includes spiro bicyclic rings such as spiropentane. A bicyclic carbocycle includes any combination of ring sizes such as 3-3 spiro ring systems, 4-4 spiro ring systems, 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, naphthyl, and bicyclo[1.1.1]pentanyl.

The term "aryl" refers to an aromatic monocyclic or aromatic multicyclic hydrocarbon ring system. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene.

The term "cycloalkyl" refers to a saturated ring in which each atom of the ring is carbon. Cycloalkyl may include monocyclic and polycyclic rings such as 3- to 10-membered monocyclic rings, 5- to 12-membered bicyclic rings, 5- to 12-membered spiro bicycles, and 5- to 12-membered bridged rings. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, spiropentane, norbornyl (i.e., bicyclo[2.2.1]heptanyl), decalinyl, 7,7 dimethyl bicyclo[2.2.1]heptanyl, bicyclo[1.1.1]pentanyl, and the like.

The term "cycloalkenyl" refers to a saturated ring in which each atom of the ring is carbon and there is at least one double bond between two ring carbons. Cycloalkenyl may include monocyclic and polycyclic rings such as 3- to 10-membered monocyclic rings, 6- to 12-membered bicyclic rings, and 5- to 12-membered bridged rings. In other embodiments, a cycloalkenyl comprises five to seven carbon atoms. The cycloalkenyl may be attached to the rest of the molecule by a single bond. Examples of monocyclic cycloalkenyls include, e.g., cyclopentenyl, cyclohexenyl, cycloheptenyl, and cyclooctenyl.

The term "halo" or, alternatively, "halogen" or "halide," means fluoro, chloro, bromo or iodo. In some embodiments, halo is fluoro, chloro, or bromo.

The term "haloalkyl" refers to an alkyl radical, as defined above, that is substituted by one or more halo radicals, for example, trifluoromethyl, dichloromethyl, bromomethyl, 2,2,2-trifluoroethyl, 1-chloromethyl-2-fluoroethyl, and the like. In some embodiments, the alkyl part of the haloalkyl radical is optionally further substituted as described herein.

The term "heterocycle" as used herein refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, 5- to 12-membered spiro bicycles, and 5- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. A bicyclic heterocycle further includes spiro bicyclic rings, e.g., 5 to 12-membered spiro bicycles, such as 2-oxa-6-azaspiro[3.3]heptane.

The term "heteroaryl" refers to a radical derived from a 5 to 18 membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is aromatic, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl).

The term "heterocycloalkyl" refers to a saturated ring with carbon atoms and at least one heteroatom. Exemplary heteroatoms include N, O, Si, P, B, and S atoms. Heterocycloalkyl may include monocyclic and polycyclic rings such as 3- to 10-membered monocyclic rings, 6- to 12-membered bicyclic rings, 5- to 12-membered spiro bicycles, and 5- to 12-membered bridged rings. The heteroatoms in the heterocycloalkyl radical are optionally oxidized. One or more nitrogen atoms, if present, are optionally quaternized. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 2-oxa-6-azaspiro[3.3]heptane, and 1,1-dioxo-thiomorpholinyl.

The term "heterocycloalkenyl" refers to an unsaturated ring with carbon atoms and at least one heteroatom and there is at least one double bond between two ring carbons. Heterocycloalkenyl does not include heteroaryl rings. Exemplary heteroatoms include N, O, Si, P, B, and S atoms. Heterocycloalkenyl may include monocyclic and polycyclic rings such as 3- to 10-membered monocyclic rings, 6- to 12-membered bicyclic rings, and 5- to 12-membered bridged rings. In other embodiments, a heterocycloalkenyl comprises five to seven ring atoms. The heterocycloalkenyl may be attached to the rest of the molecule by a single bond. Examples of monocyclic cycloalkenyls include, e.g., pyrroline (dihydropyrrole), pyrazoline (dihydropyrazole), imidazoline (dihydroimidazole), triazoline (dihydrotriazole), dihydrofuran, dihydrothiophene, oxazoline (dihydrooxazole), isoxazoline (dihydroisoxazole), thiazoline (dihydrothiazole), isothiazoline (dihydroisothiazole), oxadiazoline (dihydrooxadiazole), thiadiazoline (dihydrothiadiazole), dihydropyridine, tetrahydropyridine, dihydropyridazine, tetrahydropyridazine, dihydropyrimidine, tetrahydropyrimidine, dihydropyrazine, tetrahydropyrazine, pyran, dihydropyran, thiopyran, dihydrothiopyran, dioxine, dihydrodioxine, oxazine, dihydrooxazine, thiazine, and dihydrothiazine The term "substituted" refers to moieties having substituents replacing a hydrogen on one or more carbons or substitutable heteroatoms, e.g., an NH or NH$_2$ of a compound. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^a$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each W is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^a$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

Double bonds to oxygen atoms, such as oxo groups, are represented herein as both "=O" and "(O)". Double bonds to nitrogen atoms are represented as both "=NR" and "(NR)". Double bonds to sulfur atoms are represented as both "=S" and "(S)".

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

VI. EXAMPLES

Example 1: Intravitreal Injection of siRNA Duplexes

For intravitreal injection in mice (4-7 week-old ICR's, Envigo), a 33-gauge needle with a glass microsyringe (10-4, volume; Hamilton Company) was used. The eye was proptosed, and the needle was inserted through the equatorial sclera and inserted into the vitreous chamber at an angle of approximately 45 degrees, taking care to avoid touching the posterior part of the lens or the retina. 5 µg of siRNA duplex in 1 µL phosphate-buffered saline vehicle was injected into the vitreous. The siRNA duplexes injected are depicted in Table 2.

TABLE 2 siRNA duplexes

| Entity # | Duplexes Target | SEQ ID NO: | Sense Strand | SEQ ID NO: | Antisense Strand |
|---|---|---|---|---|---|
| ETD01206 | mANGPTL7 | 1 | [ETL3]CfsasAfcCfaGfAfUfuGfaCfaUfcAfuGfsusu | 24 | csAfsuGfaUfgUfcAfaucUfgGfuUfgsusu |
| ETD01207 | mANGPTL7 | 2 | [ETL3]CfsaAfcCfaGfAfUfuGfaCfaUfcAfuGfsusu | 25 | csAfsuGfaUfgUfcAfaucUfgGfuUfgsusu |
| ETD01208 | mANGPTL7 | 3 | [ETL3]CfaAfcCfaGfAfUfuGfaCfaUfcAfuGfsusu | 26 | csAfsuGfaUfgUfcAfaucUfgGfuUfgsusu |
| ETD01540 | mPLIN1 | 4 | [ETL3]CfsaAfcAfcUfcUfuUfcUfcGfaCfaAfsusu | 27 | usUfsgUfcGfaGfaAfaGfaGfuGfuUfgsusu |
| ETD01588 | mANGPTL7 | 5 | [ETL3]CfaAfcCfaGfAfUfuGfaCfaUfcAfuGfsusu | 28 | 5VPusAfsuGfaUfgUfcAfaucUfgGfuUfgsusu |
| ETD01589 | mANGPTL7 | 6 | [ETL3]CfaAfcCfaGfAfUfuGfaCfaUfcAfuGfsusu | 29 | usAfsuGfaUfgUfcAfaucUfgGfuUfgsusu |
| ETD01624 | mPLIN1 | 7 | [ETL3]CfsaAfcAfcUfcUfuUfcUfcGfaCfaAfsusu | 30 | 5VpusUfsgUfcGfaGfaAfaGfaGfuGfuUfgsusu |
| ETD01751 | mPLIN1 | 8 | [ETL3]CfaAfcAfcUfcUfuUfcUfcGfaCfaAfsusu | 31 | 5VpusUfsgUfcGfaGfaAfaGfaGfuGfuUfgsusu |
| ETD01716 | mANGPTL7 | 9 | [ETL3]CfaAfcCfaGfAfUfuGfaCfaUfcAfuAfsusu | 32 | 5VPusAfsuGfaUfgUfcAfaucUfgGfuUfgsusu |
| ETD01736 | mANGPTL7 | 10 | [ETL13]CfaAfcCfaGfAfUfuGfaCfaUfcAfuGfsusu | 33 | csAfsuGfaUfgUfcAfaucUfgGfuUfgsusu |
| ETD01778 | mANGPTL7 | 11 | [ETL13]CfaAfcCfaGfAfUfuGfaCfaUfcAfuAfsusu | 34 | 5VPusAfsuGfaUfgUfcAfaucUfgGfuUfgsusu |
| ETD01779 | mANGPTL7 | 12 | [ETL15]CfaAfcCfaGfAfUfuGfaCfaUfcAfuAfsusu | 35 | 5VPusAfsuGfaUfgUfcAfaucUfgGfuUfgsusu |
| ETD01786 | mANGPTL7 | 13 | [ETL13]CfaAfcCfaGfAfUfuGfaCfaUfcAfuAfsusu | 36 | usAfsuGfaUfgUfcAfaucUfgGfuUfgsusu |
| ETD01787 | mANGPTL7 | 14 | [ETL16]CfaAfcCfaGfAfUfuGfaCfaUfcAfuAfsusu | 37 | 5VPusAfsuGfaUfgUfcAfaucUfgGfuUfgsusu |
| ETD01313 | mANGPTL7 | 15 | [ETL7]CfsasAfcCfaGfAfUfuGfaCfaUfcAfuGfsusu | 38 | csAfsuGfaUfgUfcAfaucUfgGfuUfgsusu |
| ETD01503 | mANGPTL7 | 16 | [ETL8]CfsasAfcCfaGfAfUfuGfaCfaUfcAfuGfsusu | 39 | csAfsuGfaUfgUfcAfaucUfgGfuUfgsusu |
| ETD01504 | mANGPTL7 | 17 | [ETL9]CfsasAfcCfaGfAfUfuGfaCfaUfcAfuGfsusu | 40 | csAfsuGfaUfgUfcAfaucUfgGfuUfgsusu |
| ETD01505 | mANGPTL7 | 18 | [ETL10]CfsasAfcCfaGfAfUfuGfaCfaUfcAfuGfsusu | 41 | csAfsuGfaUfgUfcAfaucUfgGfuUfgsusu |

Mice were euthanized on day 14 post-injection. Both eyes from each animal were harvested and dissected along the equator, and the anterior and posterior hemispheres were placed in RNAlater. Total RNA was extracted from homogenized tissue and reverse transcribed to cDNA using a First-Strand III cDNA Synthesis kit. Normalized cDNA quantification was carried out by real-time TaqMan PCR using fluorescently labeled TaqMan probes/primers sets of selected genes (ANGPTL7, MYOC, COL1A1, COL5A1, VCAN, FN1, and PPIA). Reactions were carried out in 20 µL aliquots using TaqMan Universal PCR Master Mix No AmpErase UNG ran on an ABI Prism 7500 Fast Real-Time PCR System Sequence Detection System and analyzed by the 7500 System software. Relative Quantification (RQ) values between treated and untreated samples are calculated by the formula 2-ΔΔCT, where CT is the cycle at threshold (automatic measurement), ΔCT is CT of the assayed gene minus CT of the endogenous control (PPIA), and ΔΔCT is the ΔCT of the normalized assayed gene in the treated sample minus the ΔCT of the same gene in the untreated one (calibrator).

Results are depicted in Table 3. ETD1208 was more efficacious than ETD1207, which was more efficacious than EDT1206. This demonstrates that less (or no) phosphorothioates at the 5' end of sense strand was more efficacious than having 2 phosphorothioates at the end where the hydrophobic groups are attached.

ETD1588 was more active than ETD1589, which means that some sequences showed greater activity with 5' vinyl phosphonates on the antisense strand than without 5' vinyl phosphonates on the antisense strand.

The ETD1716-ETD1787 series enables different hydrophobic groups with 12-25 carbons. All conjugated with phosphorothioates at 5' end of sense strand.

TABLE 3 mRNA expression levels

| siRNA | Average mRNA relative to no treatment control animals |
|---|---|
| ETD01206 | 0.26 |
| ETD01207 | 0.20 |
| ETD01208 | 0.14 |
| ETD01588 | 0.43 |
| ETD01589 | 0.89 |
| ETD01716 | 0.44 |
| ETD01736 | 0.09 |
| ETD01778 | 0.34 |
| ETD01779 | 0.40 |
| ETD01786 | 0.29 |
| ETD01787 | 0.23 |

Example 2: Intravitreal Injection with mRNA and siRNA Quantitation

Intravitreal injections were performed as above with 20 µg siRNA in 1 µL. 14 days postinjection, the eyes were harvested and mRNA was quantified as shown in the previous example. siRNA was quantified using a stem loop assay according to published procedure (Cheng A, Li M, Liang Y, Wang Y, Wong L, Chen C, Vlassov A V, Magdaleno S 2009. Stem-loop RT-PCR quantification of siRNAs in vitro and in vivo. *Oligonucleotides* 19: 203-208).

Results are depicted in Table 4. There was a correlation between the size of the hydrophobic group, the percent knockdown and the levels of siRNA observed in the tissue. In general, hydrophobic groups with more carbons resulted in an increased percent knockdown and in more siRNA observed in the tissue.

TABLE 4 mRNA quantification

| Duplex | % KD relative to untreated animals | | µg siRNA/ mg of tissue | |
|---|---|---|---|---|
| | Anterior | Posterior | Anterior | Posterior |
| 1208 (stearyl) | 85 | 90 | 0.031 | 0.005 |
| 1313 (t-butyl) | 70 | 80 | 0.006 | 0.005 |
| 1503 (n-butyl) | 50 | 0 | 0.012 | 0.024 |
| 1504 (octyl) | 67 | 33 | 0.09 | 0.027 |
| 1505 (dodecyl) | 70 | 50 | 0.059 | 0.073 |

Example 3: siRNA-Mediated Knockdown of PLIN1 in Adipose Tissue in a Mice 4-7 week old ICR mice (Envigo Labs) mice in Group 1 (n=4) were given 100 uL of phosphate buffered saline (PBS) or given 500 ug of siRNA targeting mouse PLIN1 in 100 uL PBS by subcutaneous injection. On Day 14, the mice were then euthanized and an abdominal white fat sample from each was collected and placed in RNAlater (ThermoFisher Cat #AM7020). Total liver RNA was prepared by homogenizing the liver tissue in homogenization buffer (Maxwell RSC simplyRNA Tissue Kit) using a Percellys 24 tissue homogenizer (Bertin Instruments) set at 5000 rpm for two 10 second cycles. Total RNA from the lysate was purified on a Maxwell RSC 48 platform (Promega Corporation) according to the manufacturer's recommendations. The levels of liver PLIN1 mRNA were assessed by RT-qPCR using TaqMan assays for mouse PLIN1 and the mouse housekeeping gene PPIA (ThermoFisher, assay #Mm02342430_g1). Data were normalized to the level in animals receiving PBS.

The results are depicted in Table 5. Addition of 5' vinylphosphonate resulted in increased potency and enabled delivery to adipose tissue.

TABLE 5 mRNA expression levels

| siRNA | Average m RNA relative to no treatment control animals |
|---|---|
| ETD01540 | 1.7 |
| ETD01624 | 0.67 |
| ETD01751 | 0.53 |

Example 4: Delivery to Central Nervous System Injection siRNA's with modifications and hydrophobic conjugates as described are injected intracerebroventricularly or intrathecally according to published procedures (Alterman, J. F., Godinho, B. M. D. C., Hassler, M. R. et al. A divalent siRNA chemical scaffold for potent and sustained modulation of gene expression throughout the central nervous system. Nat Biotechnol 37,884-894 (2019). https://doi.org/10.1038/s41587-019-0205-0, Njoo, C., Heinl, C., Kuner, R. In Vivo SiRNA Transfection and Gene Knockdown in Spinal Cord via Rapid Noninvasive Lumbar Intrathecal Injections in Mice. J. Vis. Exp. (85), e51229, doi:10.3791/51229 (2014)). 14 days post injection, mice are euthanized, brain hemispheres are harvested, frozen, later homogenized, and tested for target mRNA and protein expression.

Example 5: Bullet Point Description of an siRNA

An example siRNA is described as follows:
21 mer:
  a. 19 base pairs
  b. 2 nt overhangs
antisense strand:
  a. vinyl phosphonate (VP) at 5' end
  b. 2 phosphorothioate bonds (PS) at each end
sense strand:
  a. hydrophobic group (C16-C18) at 5' end
  b. optional 0-2 PS at 5' end
  c. 2 PS at 3' end
modification pattern of 2' fluoro and 2' methyl groups.

Example 6: Modification Motif 1

An example siRNA includes a combination of the following modifications:
Position 9 (from 5' to 3') of the sense strand is 2' F.
If position 9 is a pyrimidine then all purines in the Sense Strand are 2'OMe, and 1-5 pyrimidines between positions 5 and 11 are 2' F provided that there are never three 2'F modifications in a row.
If position 9 is a purine then all pyrimidines in the Sense Strand are 2'OMe, and 1-5 purines between positions 5 and 11 are 2' F provided that there are never three 2'F modifications in a row.
Antisense strand odd-numbered positions are 2'OMe and even-numbered positions are a mixture of 2' F and 2' deoxy.

Example 7: Modification Motif 2

An example siRNA includes a combination of the following modifications:
Position 9 (from 5' to 3') of the sense strand is 2' deoxy.
Sense strand positions 5, 7 and 8 are 2' F.
All pyrimidines in positions 10-21 are 2' OMe, and purines are a mixture of 2' OMe and 2' F. Alternatively, all purines in positions 10-21 are 2' OMe and all pyrimidines in positions 10-21 are a mixture of 2' OMe and 2' F.
Antisense strand odd-numbered positions are 2'OMe and even-numbered positions are a mixture of 2' F and 2' deoxy.

Example 8: Synthesis of ETL Phosphoramidites

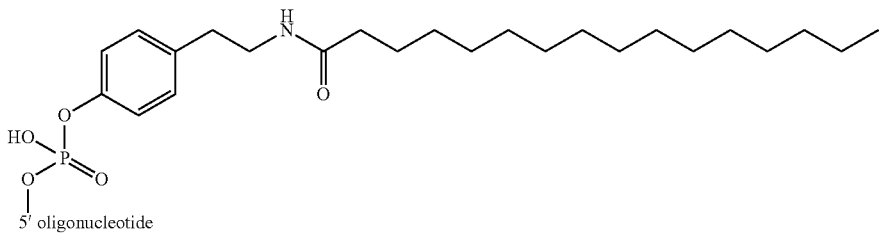

Example 8A: Synthesis of ETL20 Phosphoramidite

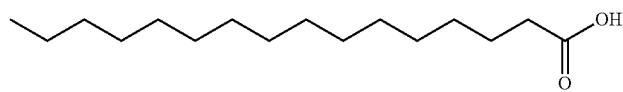

1
palmitic acid
Molecular Weight: 256.43

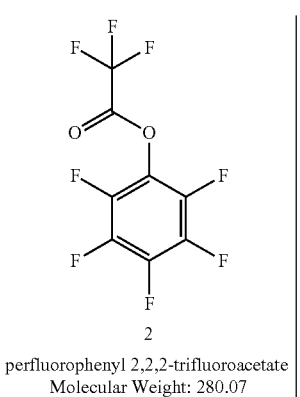

2
perfluorophenyl 2,2,2-trifluoroacetate
Molecular Weight: 280.07

-continued

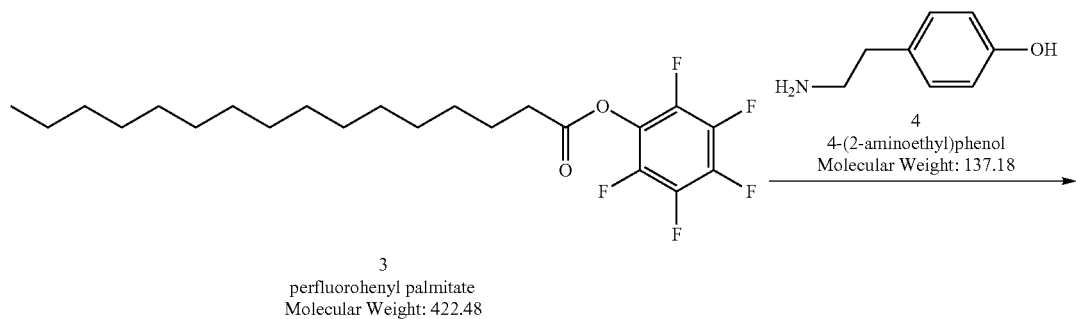

3
perfluorohenyl palmitate
Molecular Weight: 422.48

4
4-(2-aminoethyl)phenol
Molecular Weight: 137.18

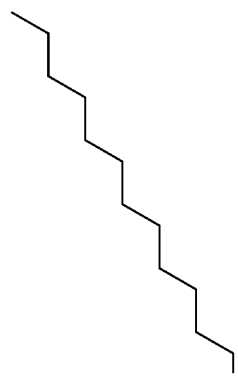
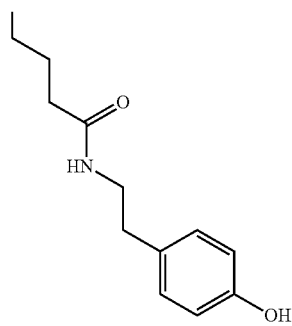

5
N-(4-hydroxyphenethyl)palmitamide
Molecular Weight: 375.60

Synthesis of N-(4-hydroxyphenethyl)palmitamide (5)

12.82 grams of 1 (palmitic acid) were weighed out and dissolved in 450 mL of $CH_2Cl_2$. 16.3 mL di-isopropyl ethyl amine (DIEA) was added to the solution of 1. Afterwards, 12.88 mL of 2 (perfluorophenyl 2,2,2-trifluoroaceate, "PFP") was added dropwise, and the reaction was stirred for 10 minutes after addition was completed. To the solution of PFP activated acid, 8.26 grams of 4 (4-(2-aminoethyl) phenol) was added via an addition funnel, and the addition funnel was rinsed with 50 mL $CH_2Cl_2$. The reaction was placed under Argon and stirred overnight. After stirring overnight 5 formed a precipitate. The precipitate was collected via filtration and washed with 75 mL MTBE, previously chilled to −20° C. The white to off-white solid was dried overnight under high vacuum. The product was used in the next step without further purification.

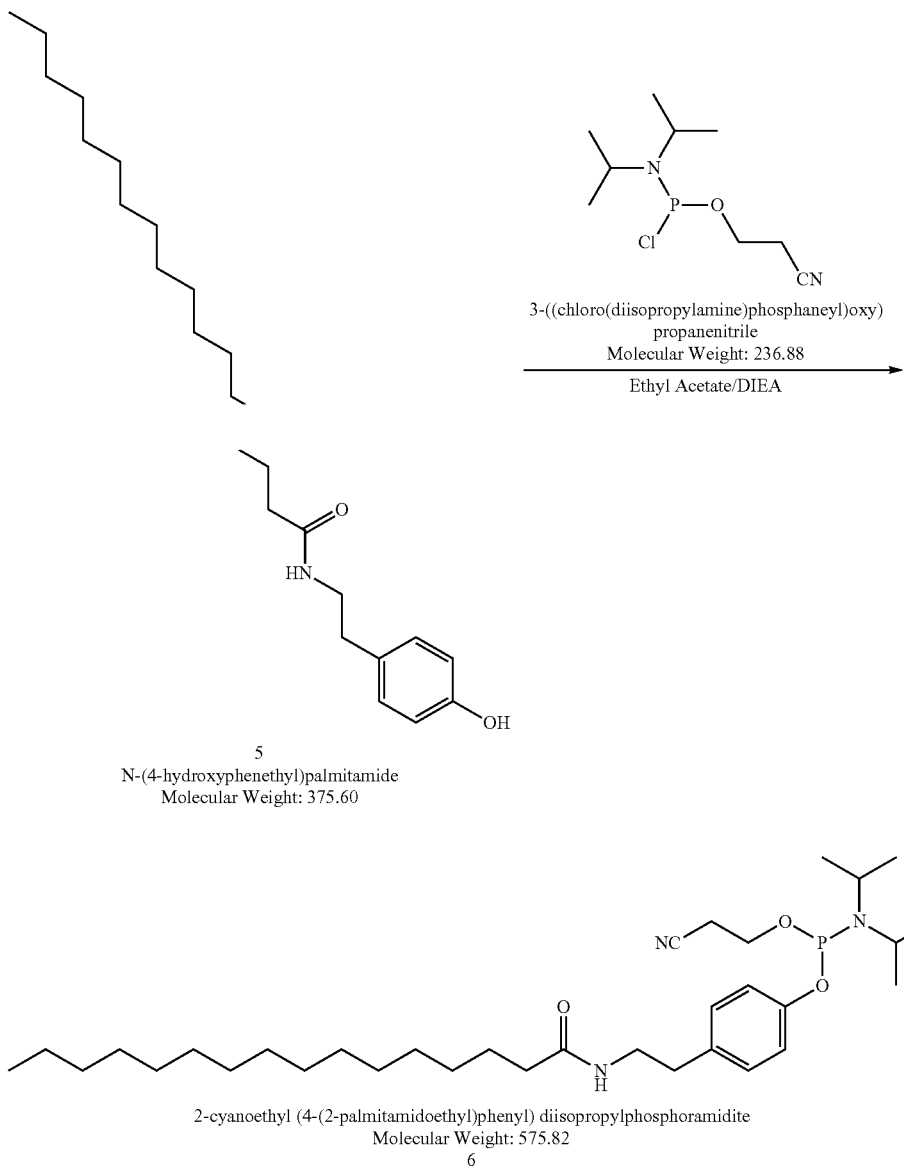

5
N-(4-hydroxyphenethyl)palmitamide
Molecular Weight: 375.60

2-cyanoethyl (4-(2-palmitamidoethyl)phenyl) diisopropylphosphoramidite
Molecular Weight: 575.82
6

Synthesis of ETL20 phosphoramidite (6): 100 mL anhydrous ethyl acetate was added to N-(4-hydroxyphenethyl) palmitamide 5 (5.2 grams), followed by addition of 250 mg 3-Angstrom molecular sieves.

The mixture was stirred for 1 hr. The mixture was heated at 50° C. to obtain a clear solution. 7.3 mL of DIEA was added, and mixture was placed into an ice bath, and the solution became cloudy. 3-((chloro(diisopropylamino)phosphaneyl)oxy)propanenitrile (3.5 mL) was slowly added to the cloudy solution. After addition was completed, the reaction mixture was removed from the ice bath and stirred at room temperature overnight under Ar. The reaction mixture was then diluted with ethyl acetate (200 mL), washed with saturated NaHCO$_3$ solution (2×50 mL) followed by brine (50 mL). The solution was dried over Na$_2$SO$_4$, filtered and concentrated under reduced pressure. The residue obtained was purified by silica gel column chromatography and eluted with 5-30% ethyl acetate in hexanes containing 2% triethylamine.

ETL18 ($C_{14}$) and ETL19 ($C_{12}$) phosphoramidites were synthesized using the procedure to generate ETL20 phosphoramidite with hydroxylbenzylamine and lauryl ($C_{12}$) or myristic ($C_{14}$) acids.

Example 9: Intravitreal Injection of siRNA Duplexes

For intravitreal injection in mice (4-7 week-old ICR's, Envigo), a 33-gauge needle with a glass microsyringe (10-4, volume; Hamilton Company) was used. The eye was proptosed, and the needle was inserted through the equatorial sclera and inserted into the vitreous chamber at an angle of approximately 45 degrees, taking care to avoid touching the posterior part of the lens or the retina. 2.5 or 1 μg of siRNA duplex in 1 μL phosphate-buffered saline vehicle was injected into the vitreous. The siRNA duplexes injected are described in Table 1.

TABLE 6 siRNA duplexes

| Entity # | Duplexes Target | SEQ ID NO: | Sense Strand | SEQ ID NO: | Antisense Strand |
|---|---|---|---|---|---|
| ETD01928 | mANGPTL7 | 19 | [ETL20]CfaAfcCfaGfAfUfuGfa CfaUfcAfuGfsusu | 42 | csAfsuGfaUfgUfcAfa ucUfgGfuUfgsusu |
| ETD01929 | mANGPTL7 | 20 | [ETL18]CfaAfcCfaGfAfUfuGfa CfaUfcAfuGfsusu | 43 | csAfsuGfaUfgUfcAfa ucUfgGfuUfgsusu |
| ETD01930 | mANGPTL7 | 21 | [ETL19]CfaAfcCfaGfAfUfuGfa CfaUfcAfuGfsusu | 44 | csAfsuGfaUfgUfcAfa ucUfgGfuUfgsusu |

Mice were euthanized on day 14 post-injection. Both eyes from each animal were harvested and dissected along the equator, and the anterior and posterior hemispheres were placed in RNAlater. Total RNA was extracted from homogenized tissue and reverse transcribed to cDNA using a First-Strand III cDNA Synthesis kit. Normalized cDNA quantification was carried out by real-time TaqMan PCR using fluorescently labeled TaqMan probes/primers sets of selected genes (ANGPTL7, MYOC, COL1A1, COL5A1, VCAN, FN1, and PPIA). Reactions were carried out in 20 µL aliquots using TaqMan Universal PCR Master Mix No AmpErase UNG ran on an ABI Prism 7500 Fast Real-Time PCR System Sequence Detection System and analyzed by the 7500 System software. Relative Quantification (RQ) values between treated and untreated samples are calculated by the formula 2-ΔΔCT, where CT is the cycle at threshold (automatic measurement), ΔCT is CT of the assayed gene minus CT of the endogenous control (PPIA), and ΔΔCT is the ΔCT of the normalized assayed gene in the treated sample minus the ΔCT of the same gene in the untreated one (calibrator).

Among other things, the ETD1928-1930 series shows the usefulness of different hydrophobic groups with 12-16 carbons attached to tyramine. The hydrophobic groups were conjugated without phosphorothioates at the 5' end of the sense strand.

TABLE 7 mRNA expression levels

| SIRNA | Average mRNA relative to no treatment control animals |
|---|---|
| | 2.5 µg dose |
| ETD01928 | 0.20 |
| ETD01929 | 0.09 |
| ETD01930 | 0.05 |

TABLE 7-continued mRNA expression levels

| SIRNA | Average mRNA relative to no treatment control animals |
|---|---|
| | 1 µg dose |
| ETD01928 | 0.71 |
| ETD01929 | 0.81 |
| ETD01930 | 0.76 |

Example 10: Intracerebroventricular Injections

Mice were induced to anesthetic states in an induction chamber with 1.2% isoflurane vaporized by oxygen of 1.0 L/min and then transferred and fixed to a stereotaxic frame while keeping anesthetized by 0.8% isoflurane through a mask. Skull was exposed and single intracerebroventricular injections (5 artificial cerebrospinal fluid as vehicle) were performed at 500 nl min$^{-1}$ after needle placement at the following coordinates from bregma: −0.2 mm anterior-posterior, 0.8 mm mediolateral and −2.5 mm dorsoventral using a Standard U-Frame Stereotaxic Instrument for Mouse (Harvard Apparatus 75-1808) and a Stereotaxic Anesthesia Adapters with Anesthesia Masks (Harvard Apparatus 75-1856).

татBLE 8 siRNA duplexes

| Entity # | Target | SEQ ID NO | Sense Strand | SEQ ID NO | Antisense Strand |
|---|---|---|---|---|---|
| ETD01917 | MTRES1 | 22 | [ETL3]cuAfcAfaAfgGfuGfa AfcucAfgAfsusu | 45 | usCfsugaGfuUfcaccuUfuGf uagsusu |
| ETD02209 | MTRES1 | 23 | [ETL20]cuAfcAfaAfgGfuGf aAfcucAfgAfsusu | 46 | usCfsugaGfuUfcaccuUfuGf uagsusu |

Where ETL3 is stearyl coupled to 5' of sense strand using stearyl phosphoramidite (Glen Research, 10-1979-90).

Mice were euthanized on day 14 post-injection. Brains from each animal were harvested and dissected into right and left hemispheres.

Total RNA was extracted from homogenized tissue and reverse transcribed to cDNA using a First-Strand III cDNA Synthesis kit. Normalized cDNA quantification was carried out by real-time TaqMan PCR using fluorescently labeled TaqMan probes/primers sets of selected genes (MTRES1, MYOC, COL1A1, COL5A1, VCAN, FN1, and PPIA).

Reactions were carried out in 20 µL aliquots using TaqMan Universal PCR Master Mix No AmpErase UNG ran on an ABI Prism 7500 Fast Real-Time PCR System Sequence Detection System and analyzed by the 7500 System software. Relative Quantification (RQ) values between treated and untreated samples were calculated by the formula 2-ΔΔCT, where CT is the cycle at threshold (automatic measurement), ΔCT is CT of the assayed gene minus CT of the endogenous control (PPIA), and ΔΔCT was the ΔCT of the normalized assayed gene in the treated sample minus the ΔCT of the same gene in the untreated one (calibrator).

TABLE 9 mRNA expression levels

| siRNA | Average m RNA relative to no treatment control animals |
|---|---|
| 25 µg dose | |
| ETD01917 | 0.90 |
| ETD02209 | 0.44 |
| 10 µg dose | |
| ETD01917 | 0.45 |
| ETD02209 | 0.22 |

Example 11: Rat Intrathecal Injection

Male Sprague Dawley rats (n=2) were used for intrathecal (IT) injection of siRNAs. Duplex ETD02273 was formulated at 30 mg ml$^{-1}$ in artificial cerebrospinal fluid (aCSF), and was administered as 30-µl IT injections by lumbar puncture in the dorsal region of the spine between the L3-L5 vertebral space to the rats. Duplex ETD02210 was formulated at 9 mg ml$^{-1}$ in artificial cerebrospinal fluid (aCSF), and was administered as 100-µl IT injections by lumbar puncture in the dorsal region of the spine between the L3-L5 vertebral space to the rats.

After the rats were anesthetized with isoflurane, the rats were placed on a warm heating pad. The IT injection site was shaved and disinfected. An incision was made to expose the spinal column. siRNA was administered with a 30-gauge insulin syringe. Proper placement of the needle was confirmed via CSF backflow in the hub of the needle and a tail flick. Once siRNA administration was completed, a gentle constant pressure on the plunger was maintained for 30 seconds. The incision was sutured and secured with tissue glue. The rats were placed in sternal recumbency on a heating pad until recovery.

The rats were euthanized on day 14 post-injection. Samples of liver, right and left (R/L) frontal cortex, R/L temporal cortex, hippocampus, cerebellum and the spinal cord from each rat were collected and placed in RNAlater (ThermoFisher Catalog #AM7020) until processing.

Total liver RNA was prepared by homogenizing the liver tissue in homogenization buffer (Maxwell RSC simplyRNA Tissue Kit) using a Percellys 24 tissue homogenizer (Bertin Instruments) set at 5000 rpm for two 10 second cycles. Total RNA from the lysate was purified on a Maxwell RSC 48 platform (Promega Corporation) according to the manufacturer's recommendations. Preparation of cDNA was performed using Quanta qScript cDNA SuperMix (VWR, Catalog #95048-500) according to the manufacturer's instructions.

The relative levels of liver MTRES1 mRNA were assessed by RT-qPCR in triplicate on a QuantStudio™ 6 Pro Real-Time PCR System using TaqMan assays for rat MTRES1 (ThermoFisher, assay #Rn01441122_m1) and the rat housekeeping gene PPIA (ThermoFisher, assay #Rn03302269_gH) and PerfeCTa® qPCR FastMix®, Low ROX™ (VWR, Catalog #101419-222).

Data were normalized to the mean MTRES1 mRNA level in animals receiving no treatment. Results are shown in Table 10 and Table 11 below.

TABLE 10 mRNA expression levels

| Treatment/ Expression Location | Cerebellum | Frontal Cortex Right | Frontal Cortex Left | Hippocampus | Liver | Spinal Cord | Temporal Cortex Right | Temporal Cortex Left |
|---|---|---|---|---|---|---|---|---|
| No treatment | 1.00 | 1.00 | 1.00 | 1.00 | 1.00 | 1.00 | 1.00 | 1.00 |
| ETD02210 9 mg/ml | 0.64 | 0.92 | 0.67 | 0.73 | 0.21 | 0.5 | 0.91 | 1.06 |
| ETD02273 30 mg/ml | 0.36 | 0.85 | 0.95 | 0.96 | 0.2 | 0.35 | 1.08 | 1.3 |

TABLE 11 siRNA duplexes

| Entity # | Target | SEQ ID NO: | Sense Strand | SEQ ID NO: | Antisense Strand |
|---|---|---|---|---|---|
| ETD02210 | MTRES1 | 47 | [ETL20]ucuacAfAfAfGf Gfugaacucaasusu | 49 | 5VPusUfsgAfgUfuCfaCfc UfuUfgUfaGfasusu |
| ETD02273 | MTRES1 | 48 | [ETL20]ucuacAfAfAfGf Gfugaacucaasusu | 50 | 5VPusUfsgagUfuCfaCfc UfuUfgUfaGfasusu |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and compositions within the scope of these claims and their equivalents be covered thereby.

What is claimed is:

1. A composition comprising:
a small interfering RNA (siRNA) comprising a sense strand, an antisense strand, and a
ligand comprising the structure:

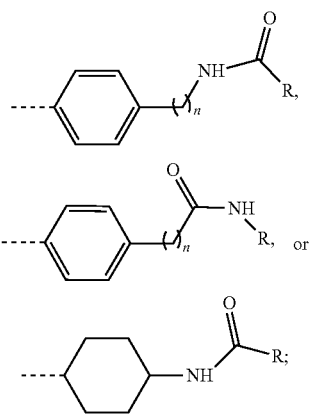

and
wherein the dotted line indicates a connection to the 5' or 3' end of the sense or antisense strand, n is 0-3, and R is an alkyl group containing 4-20 carbons.

2. The composition of claim 1, wherein the composition comprises the structure:

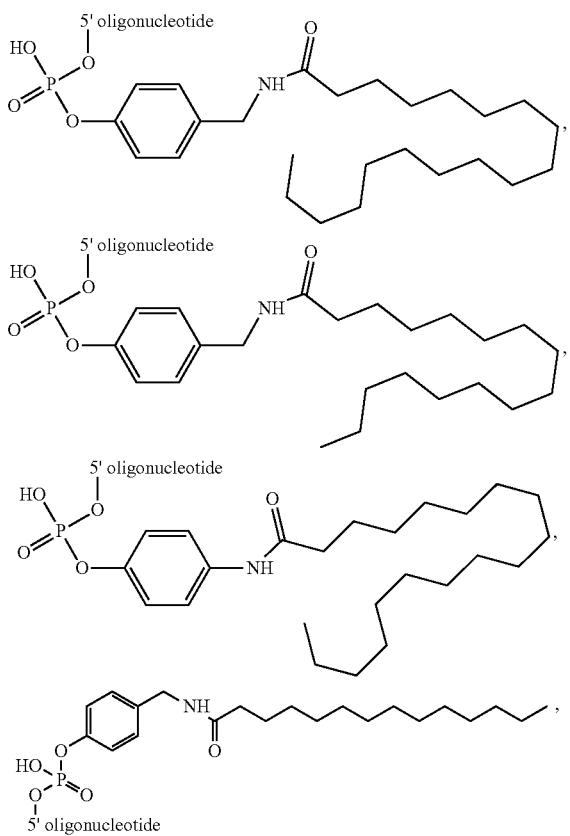

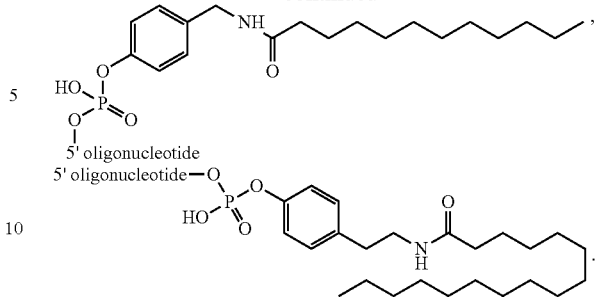

3. The composition of claim 1, wherein the ligand is connected to the 5' end of the sense strand.

4. The composition of claim 1, wherein the antisense strand comprises a vinyl phosphonate.

5. The composition of claim 1, wherein the sense strand or antisense strand comprises one or two phosphorothioate linkages at a 5' or 3' end of the sense strand or antisense strand.

6. The composition of claim 1, wherein any one of the following is true with regard to the sense strand or antisense strand, with the proviso that the sense strand or antisense strand may include a 2' deoxy nucleoside:
all purine nucleosides comprise 2' fluoro, and all pyrimidine nucleosides are modified with a mixture of 2' fluoro or 2'-O-methyl;
all purine nucleosides comprise 2'-O-methyl, and all pyrimidine nucleosides are modified with a mixture of 2' fluoro or 2'-O-methyl;
all purine nucleosides comprise 2' fluoro, and all pyrimidine nucleosides comprise 2'-O-methyl;
all pyrimidine nucleosides comprise 2' fluoro, and all purine nucleosides are modified with a mixture of 2' fluoro and 2'-O-methyl;
all pyrimidine nucleosides comprise 2'-O-methyl, and all purine nucleosides are modified with a mixture of 2' fluoro and 2'-O-methyl; or
all pyrimidine nucleosides comprise 2' fluoro, and all purine nucleosides comprise 2'-O-methyl.

7. The composition of claim 1, wherein the antisense strand comprises one or two 5' phosphorothioate linkages.

8. The composition of claim 1, wherein the antisense strand comprises one or two 3' phosphorothioate linkages.

9. The composition of claim 1, wherein the sense strand comprises one or two 5' phosphorothioate linkages.

10. The composition of claim 1, wherein the sense strand does not comprise one or two 5' phosphorothioate linkages.

11. The composition of claim 1, wherein the sense strand comprises 5' phosphate linkages.

12. The composition of claim 1, wherein the sense strand comprises one or two 3' phosphorothioate linkages.

13. The composition of claim 6, wherein the sense strand includes the 2' deoxy nucleoside.

14. The composition of claim 6, wherein the sense strand does not include the 2' deoxy nucleoside.

15. The composition of claim 1, wherein any one of the following is true with regard to the antisense strand:
all purine nucleosides comprise 2' fluoro, and all pyrimidine nucleosides are modified with a mixture of 2' fluoro and 2'-O-methyl;
all purine nucleosides comprise 2'-O-methyl, and all pyrimidine nucleosides are modified with a mixture of 2' fluoro and 2'-O-methyl;

all purine nucleosides comprise 2'-O-methyl, and all pyrimidine nucleosides comprise 2' fluoro;

all pyrimidine nucleosides comprise 2' fluoro, and all purine nucleosides are modified with a mixture of 2' fluoro and 2'-O-methyl;

all pyrimidine nucleosides comprise 2'-O-methyl, and all purine nucleosides are modified with a mixture of 2' fluoro and 2'-O-methyl; or all pyrimidine nucleosides comprise 2'-O-methyl, and all purine nucleosides comprise 2' fluoro.

16. A composition comprising:

a small interfering RNA (siRNA) comprising a sense strand, an antisense strand, and a ligand comprising the structure:

wherein the dotted line indicates a connection to the 5' or 3' end of the sense or antisense strand, and R is an alkyl group containing 4-20 carbons with the proviso that R is not an octane.

17. The composition of claim 16, wherein the composition comprises the structure:

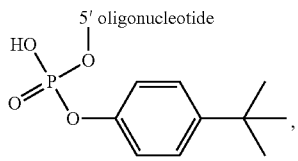

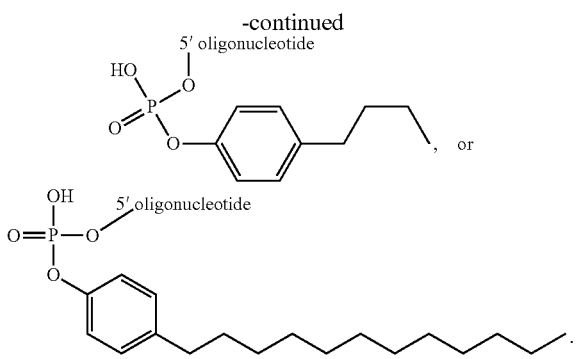

18. The composition of claim 16, wherein the ligand is connected to the 5' end of the sense strand.

19. The composition of claim 16, wherein any one of the following is true with regard to the sense strand or antisense strand, with the proviso that the sense strand or antisense strand may include a 2' deoxy nucleoside:

all purine nucleosides comprise 2' fluoro, and all pyrimidine nucleosides are modified with a mixture of 2' fluoro or 2'-O-methyl;

all purine nucleosides comprise 2'-O-methyl, and all pyrimidine nucleosides are modified with a mixture of 2' fluoro or 2'-O-methyl;

all purine nucleosides comprise 2' fluoro, and all pyrimidine nucleosides comprise 2'-O-methyl;

all pyrimidine nucleosides comprise 2' fluoro, and all purine nucleosides are modified with a mixture of 2' fluoro and 2'-O-methyl;

all pyrimidine nucleosides comprise 2'-O-methyl, and all purine nucleosides are modified with a mixture of 2' fluoro and 2'-O-methyl; or all pyrimidine nucleosides comprise 2' fluoro, and all purine nucleosides comprise 2'-O-methyl.

* * * * *

```
                        SEQUENCE LISTING

Sequence total quantity: 50
SEQ ID NO: 1            moltype = RNA  length = 21
FEATURE                 Location/Qualifiers
source                  1..21
                        mol_type = other RNA
                        organism = synthetic construct
modified_base           1..3
                        mod_base = OTHER
                        note = phosphorothioate linkage
modified_base           19..21
                        mod_base = OTHER
                        note = phosphorothioate linkage
modified_base           1
                        mod_base = OTHER
                        note = 2-fluoro-modified nucleoside
modified_base           3
                        mod_base = OTHER
                        note = 2-fluoro-modified nucleoside
modified_base           5
                        mod_base = OTHER
                        note = 2-fluoro-modified nucleoside
modified_base           7..9
                        mod_base = OTHER
                        note = 2-fluoro-modified nucleoside
modified_base           11
                        mod_base = OTHER
                        note = 2-fluoro-modified nucleoside
modified_base           13
                        mod_base = OTHER
                        note = 2-fluoro-modified nucleoside
modified_base           15
                        mod_base = OTHER
                        note = 2-fluoro-modified nucleoside
modified_base           17
                        mod_base = OTHER
                        note = 2-fluoro-modified nucleoside
modified_base           19
                        mod_base = OTHER
                        note = 2-fluoro-modified nucleoside
modified_base           20..21
                        mod_base = OTHER
                        note = 2-O-methyl modified nucleoside
modified_base           2
                        mod_base = OTHER
                        note = 2-O-methyl modified nucleoside
modified_base           4
                        mod_base = OTHER
                        note = 2-O-methyl modified nucleoside
modified_base           6
                        mod_base = OTHER
                        note = 2-O-methyl modified nucleoside
modified_base           10
                        mod_base = OTHER
                        note = 2-O-methyl modified nucleoside
modified_base           12
                        mod_base = OTHER
                        note = 2-O-methyl modified nucleoside
modified_base           14
                        mod_base = OTHER
                        note = 2-O-methyl modified nucleoside
modified_base           16
                        mod_base = OTHER
                        note = 2-O-methyl modified nucleoside
modified_base           18
                        mod_base = OTHER
                        note = 2-O-methyl modified nucleoside
SEQUENCE: 1
caaccagatt gacatcatgt t                                                    21
```

```
SEQ ID NO: 2           moltype = RNA  length = 21
FEATURE                Location/Qualifiers
source                 1..21
                       mol_type = other RNA
                       organism = synthetic construct
modified_base          1..2
                       mod_base = OTHER
                       note = phosphorothioate linkage
modified_base          19..21
                       mod_base = OTHER
                       note = phosphorothioate linkage
modified_base          1
                       mod_base = OTHER
                       note = 2-fluoro-modified nucleoside
modified_base          3
                       mod_base = OTHER
                       note = 2-fluoro-modified nucleoside
modified_base          5
                       mod_base = OTHER
                       note = 2-fluoro-modified nucleoside
modified_base          7..9
                       mod_base = OTHER
                       note = 2-fluoro-modified nucleoside
modified_base          11
                       mod_base = OTHER
                       note = 2-fluoro-modified nucleoside
modified_base          13
                       mod_base = OTHER
                       note = 2-fluoro-modified nucleoside
modified_base          15
                       mod_base = OTHER
                       note = 2-fluoro-modified nucleoside
modified_base          17
                       mod_base = OTHER
                       note = 2-fluoro-modified nucleoside
modified_base          19
                       mod_base = OTHER
                       note = 2-fluoro-modified nucleoside
modified_base          20..21
                       mod_base = OTHER
                       note = 2-O-methyl modified nucleoside
modified_base          2
                       mod_base = OTHER
                       note = 2-O-methyl modified nucleoside
modified_base          6
                       mod_base = OTHER
                       note = 2-O-methyl modified nucleoside
modified_base          10
                       mod_base = OTHER
                       note = 2-O-methyl modified nucleoside
modified_base          12
                       mod_base = OTHER
                       note = 2-O-methyl modified nucleoside
modified_base          14
                       mod_base = OTHER
                       note = 2-O-methyl modified nucleoside
modified_base          16
                       mod_base = OTHER
                       note = 2-O-methyl modified nucleoside
modified_base          18
                       mod_base = OTHER
                       note = 2-O-methyl modified nucleoside
SEQUENCE: 2
caaccagatt gacatcatgt t                                             21

SEQ ID NO: 3           moltype = RNA  length = 21
FEATURE                Location/Qualifiers
source                 1..21
                       mol_type = other RNA
                       organism = synthetic construct
modified_base          19..21
                       mod_base = OTHER
                       note = phosphorothioate linkage
modified_base          1
                       mod_base = OTHER
                       note = 2-fluoro-modified nucleoside
```

```
modified_base       3
                    mod_base = OTHER
                    note = 2-fluoro-modified nucleoside
modified_base       5
                    mod_base = OTHER
                    note = 2-fluoro-modified nucleoside
modified_base       7..9
                    mod_base = OTHER
                    note = 2-fluoro-modified nucleoside
modified_base       11
                    mod_base = OTHER
                    note = 2-fluoro-modified nucleoside
modified_base       13
                    mod_base = OTHER
                    note = 2-fluoro-modified nucleoside
modified_base       15
                    mod_base = OTHER
                    note = 2-fluoro-modified nucleoside
modified_base       17
                    mod_base = OTHER
                    note = 2-fluoro-modified nucleoside
modified_base       19
                    mod_base = OTHER
                    note = 2-fluoro-modified nucleoside
modified_base       20..21
                    mod_base = OTHER
                    note = 2-O-methyl modified nucleoside
modified_base       2
                    mod_base = OTHER
                    note = 2-O-methyl modified nucleoside
modified_base       4
                    mod_base = OTHER
                    note = 2-O-methyl modified nucleoside
modified_base       6
                    mod_base = OTHER
                    note = 2-O-methyl modified nucleoside
modified_base       10
                    mod_base = OTHER
                    note = 2-O-methyl modified nucleoside
modified_base       12
                    mod_base = OTHER
                    note = 2-O-methyl modified nucleoside
modified_base       14
                    mod_base = OTHER
                    note = 2-O-methyl modified nucleoside
modified_base       16
                    mod_base = OTHER
                    note = 2-O-methyl modified nucleoside
modified_base       18
                    mod_base = OTHER
                    note = 2-O-methyl modified nucleoside
SEQUENCE: 3
caaccagatt gacatcatgt t                                              21

SEQ ID NO: 4        moltype = RNA   length = 21
FEATURE             Location/Qualifiers
source              1..21
                    mol_type = other RNA
                    organism = synthetic construct
modified_base       1..2
                    mod_base = OTHER
                    note = phosphorothioate linkage
modified_base       19..21
                    mod_base = OTHER
                    note = phosphorothioate linkage
modified_base       1
                    mod_base = OTHER
                    note = 2-fluoro-modified nucleoside
modified_base       5
                    mod_base = OTHER
                    note = 2-fluoro-modified nucleoside
modified_base       3
                    mod_base = OTHER
                    note = 2-fluoro-modified nucleoside
modified_base       7
                    mod_base = OTHER
                    note = 2-fluoro-modified nucleoside
```

```
modified_base      9
                   mod_base = OTHER
                   note = 2-fluoro-modified nucleoside
modified_base      11
                   mod_base = OTHER
                   note = 2-fluoro-modified nucleoside
modified_base      13
                   mod_base = OTHER
                   note = 2-fluoro-modified nucleoside
modified_base      15
                   mod_base = OTHER
                   note = 2-fluoro-modified nucleoside
modified_base      17
                   mod_base = OTHER
                   note = 2-fluoro-modified nucleoside
modified_base      19
                   mod_base = OTHER
                   note = 2-fluoro-modified nucleoside
modified_base      20..21
                   mod_base = OTHER
                   note = 2-O-methyl modified nucleoside
modified_base      2
                   mod_base = OTHER
                   note = 2-O-methyl modified nucleoside
modified_base      4
                   mod_base = OTHER
                   note = 2-O-methyl modified nucleoside
modified_base      6
                   mod_base = OTHER
                   note = 2-O-methyl modified nucleoside
modified_base      8
                   mod_base = OTHER
                   note = 2-O-methyl modified nucleoside
modified_base      10
                   mod_base = OTHER
                   note = 2-O-methyl modified nucleoside
modified_base      12
                   mod_base = OTHER
                   note = 2-O-methyl modified nucleoside
modified_base      14
                   mod_base = OTHER
                   note = 2-O-methyl modified nucleoside
modified_base      16
                   mod_base = OTHER
                   note = 2-O-methyl modified nucleoside
modified_base      18
                   mod_base = OTHER
                   note = 2-O-methyl modified nucleoside
SEQUENCE: 4
caacactctt tctcgacaat t                                         21

SEQ ID NO: 5       moltype = RNA   length = 21
FEATURE            Location/Qualifiers
source             1..21
                   mol_type = other RNA
                   organism = synthetic construct
modified_base      19..21
                   mod_base = OTHER
                   note = phosphorothioate linkage
modified_base      1
                   mod_base = OTHER
                   note = 2-fluoro-modified nucleoside
modified_base      3
                   mod_base = OTHER
                   note = 2-fluoro-modified nucleoside
modified_base      5
                   mod_base = OTHER
                   note = 2-fluoro-modified nucleoside
modified_base      7..9
                   mod_base = OTHER
                   note = 2-fluoro-modified nucleoside
modified_base      11
                   mod_base = OTHER
                   note = 2-fluoro-modified nucleoside
```

```
modified_base           13
                        mod_base = OTHER
                        note = 2-fluoro-modified nucleoside
modified_base           15
                        mod_base = OTHER
                        note = 2-fluoro-modified nucleoside
modified_base           17
                        mod_base = OTHER
                        note = 2-fluoro-modified nucleoside
modified_base           19
                        mod_base = OTHER
                        note = 2-fluoro-modified nucleoside
modified_base           20..21
                        mod_base = OTHER
                        note = 2-O-methyl modified nucleoside
modified_base           2
                        mod_base = OTHER
                        note = 2-O-methyl modified nucleoside
modified_base           4
                        mod_base = OTHER
                        note = 2-O-methyl modified nucleoside
modified_base           6
                        mod_base = OTHER
                        note = 2-O-methyl modified nucleoside
modified_base           10
                        mod_base = OTHER
                        note = 2-O-methyl modified nucleoside
modified_base           12
                        mod_base = OTHER
                        note = 2-O-methyl modified nucleoside
modified_base           14
                        mod_base = OTHER
                        note = 2-O-methyl modified nucleoside
modified_base           16
                        mod_base = OTHER
                        note = 2-O-methyl modified nucleoside
modified_base           18
                        mod_base = OTHER
                        note = 2-O-methyl modified nucleoside
SEQUENCE: 5
caaccagatt gacatcatgt t                                            21

SEQ ID NO: 6            moltype = RNA  length = 21
FEATURE                 Location/Qualifiers
source                  1..21
                        mol_type = other RNA
                        organism = synthetic construct
modified_base           7..9
                        mod_base = OTHER
                        note = 2-fluoro-modified nucleoside
modified_base           1
                        mod_base = OTHER
                        note = 2-fluoro-modified nucleoside
modified_base           3
                        mod_base = OTHER
                        note = 2-fluoro-modified nucleoside
modified_base           5
                        mod_base = OTHER
                        note = 2-fluoro-modified nucleoside
modified_base           11
                        mod_base = OTHER
                        note = 2-fluoro-modified nucleoside
modified_base           13
                        mod_base = OTHER
                        note = 2-fluoro-modified nucleoside
modified_base           15
                        mod_base = OTHER
                        note = 2-fluoro-modified nucleoside
modified_base           17
                        mod_base = OTHER
                        note = 2-fluoro-modified nucleoside
modified_base           19
                        mod_base = OTHER
                        note = 2-fluoro-modified nucleoside
modified_base           19..21
                        mod_base = OTHER
                        note = phosphorothioate linkage
```

```
modified_base          20..21
                       mod_base = OTHER
                       note = 2-O-methyl modified nucleoside
modified_base          2
                       mod_base = OTHER
                       note = 2-O-methyl modified nucleoside
modified_base          4
                       mod_base = OTHER
                       note = 2-O-methyl modified nucleoside
modified_base          6
                       mod_base = OTHER
                       note = 2-O-methyl modified nucleoside
modified_base          10
                       mod_base = OTHER
                       note = 2-O-methyl modified nucleoside
modified_base          12
                       mod_base = OTHER
                       note = 2-O-methyl modified nucleoside
modified_base          14
                       mod_base = OTHER
                       note = 2-O-methyl modified nucleoside
modified_base          16
                       mod_base = OTHER
                       note = 2-O-methyl modified nucleoside
modified_base          18
                       mod_base = OTHER
                       note = 2-O-methyl modified nucleoside
SEQUENCE: 6
caaccagatt gacatcatgt t                                              21

SEQ ID NO: 7           moltype = RNA   length = 21
FEATURE                Location/Qualifiers
source                 1..21
                       mol_type = other RNA
                       organism = synthetic construct
modified_base          1..2
                       mod_base = OTHER
                       note = phosphorothioate linkage
modified_base          19..21
                       mod_base = OTHER
                       note = phosphorothioate linkage
modified_base          1
                       mod_base = OTHER
                       note = 2-fluoro-modified nucleoside
modified_base          3
                       mod_base = OTHER
                       note = 2-fluoro-modified nucleoside
modified_base          5
                       mod_base = OTHER
                       note = 2-fluoro-modified nucleoside
modified_base          7
                       mod_base = OTHER
                       note = 2-fluoro-modified nucleoside
modified_base          9
                       mod_base = OTHER
                       note = 2-fluoro-modified nucleoside
modified_base          11
                       mod_base = OTHER
                       note = 2-fluoro-modified nucleoside
modified_base          13
                       mod_base = OTHER
                       note = 2-fluoro-modified nucleoside
modified_base          15
                       mod_base = OTHER
                       note = 2-fluoro-modified nucleoside
modified_base          17
                       mod_base = OTHER
                       note = 2-fluoro-modified nucleoside
modified_base          19
                       mod_base = OTHER
                       note = 2-fluoro-modified nucleoside
modified_base          2
                       mod_base = OTHER
                       note = 2-O-methyl modified nucleoside
modified_base          20..21
                       mod_base = OTHER
                       note = 2-O-methyl modified nucleoside
```

-continued

| | |
|---|---|
| modified_base | 4<br>mod_base = OTHER<br>note = 2-O-methyl modified nucleoside |
| modified_base | 6<br>mod_base = OTHER<br>note = 2-O-methyl modified nucleoside |
| modified_base | 8<br>mod_base = OTHER<br>note = 2-O-methyl modified nucleoside |
| modified_base | 10<br>mod_base = OTHER<br>note = 2-O-methyl modified nucleoside |
| modified_base | 12<br>mod_base = OTHER<br>note = 2-O-methyl modified nucleoside |
| modified_base | 14<br>mod_base = OTHER<br>note = 2-O-methyl modified nucleoside |
| modified_base | 16<br>mod_base = OTHER<br>note = 2-O-methyl modified nucleoside |
| modified_base | 18<br>mod_base = OTHER<br>note = 2-O-methyl modified nucleoside |
| SEQUENCE: 7 | |
| caacactctt tctcgacaat t | 21 |
| SEQ ID NO: 8<br>FEATURE<br>source | moltype = RNA  length = 21<br>Location/Qualifiers<br>1..21<br>mol_type = other RNA<br>organism = synthetic construct |
| modified_base | 1<br>mod_base = OTHER<br>note = 2-fluoro-modified nucleoside |
| modified_base | 3<br>mod_base = OTHER<br>note = 2-fluoro-modified nucleoside |
| modified_base | 5<br>mod_base = OTHER<br>note = 2-fluoro-modified nucleoside |
| modified_base | 7<br>mod_base = OTHER<br>note = 2-fluoro-modified nucleoside |
| modified_base | 9<br>mod_base = OTHER<br>note = 2-fluoro-modified nucleoside |
| modified_base | 11<br>mod_base = OTHER<br>note = 2-fluoro-modified nucleoside |
| modified_base | 13<br>mod_base = OTHER<br>note = 2-fluoro-modified nucleoside |
| modified_base | 15<br>mod_base = OTHER<br>note = 2-fluoro-modified nucleoside |
| modified_base | 17<br>mod_base = OTHER<br>note = 2-fluoro-modified nucleoside |
| modified_base | 19<br>mod_base = OTHER<br>note = 2-fluoro-modified nucleoside |
| modified_base | 19..21<br>mod_base = OTHER<br>note = phosphorothioate linkage |
| modified_base | 20..21<br>mod_base = OTHER<br>note = 2-O-methyl modified nucleoside |
| modified_base | 2<br>mod_base = OTHER<br>note = 2-O-methyl modified nucleoside |
| modified_base | 4<br>mod_base = OTHER<br>note = 2-O-methyl modified nucleoside |
| modified_base | 6<br>mod_base = OTHER<br>note = 2-O-methyl modified nucleoside |

```
modified_base         8
                      mod_base = OTHER
                      note = 2-O-methyl modified nucleoside
modified_base         10
                      mod_base = OTHER
                      note = 2-O-methyl modified nucleoside
modified_base         12
                      mod_base = OTHER
                      note = 2-O-methyl modified nucleoside
modified_base         14
                      mod_base = OTHER
                      note = 2-O-methyl modified nucleoside
modified_base         16
                      mod_base = OTHER
                      note = 2-O-methyl modified nucleoside
modified_base         18
                      mod_base = OTHER
                      note = 2-O-methyl modified nucleoside
SEQUENCE: 8
caacactctt tctcgacaat t                                              21

SEQ ID NO: 9          moltype = RNA   length = 21
FEATURE               Location/Qualifiers
source                1..21
                      mol_type = other RNA
                      organism = synthetic construct
modified_base         19..21
                      mod_base = OTHER
                      note = phosphorothioate linkage
modified_base         1
                      mod_base = OTHER
                      note = 2-fluoro-modified nucleoside
modified_base         3
                      mod_base = OTHER
                      note = 2-fluoro-modified nucleoside
modified_base         5
                      mod_base = OTHER
                      note = 2-fluoro-modified nucleoside
modified_base         7..9
                      mod_base = OTHER
                      note = 2-fluoro-modified nucleoside
modified_base         11
                      mod_base = OTHER
                      note = 2-fluoro-modified nucleoside
modified_base         13
                      mod_base = OTHER
                      note = 2-fluoro-modified nucleoside
modified_base         15
                      mod_base = OTHER
                      note = 2-fluoro-modified nucleoside
modified_base         17
                      mod_base = OTHER
                      note = 2-fluoro-modified nucleoside
modified_base         19
                      mod_base = OTHER
                      note = 2-fluoro-modified nucleoside
modified_base         20..21
                      mod_base = OTHER
                      note = 2-O-methyl modified nucleoside
modified_base         2
                      mod_base = OTHER
                      note = 2-O-methyl modified nucleoside
modified_base         4
                      mod_base = OTHER
                      note = 2-O-methyl modified nucleoside
modified_base         6
                      mod_base = OTHER
                      note = 2-O-methyl modified nucleoside
modified_base         10
                      mod_base = OTHER
                      note = 2-O-methyl modified nucleoside
modified_base         12
                      mod_base = OTHER
                      note = 2-O-methyl modified nucleoside
modified_base         14
                      mod_base = OTHER
                      note = 2-O-methyl modified nucleoside
```

```
modified_base          16
                       mod_base = OTHER
                       note = 2-O-methyl modified nucleoside
modified_base          18
                       mod_base = OTHER
                       note = 2-O-methyl modified nucleoside
SEQUENCE: 9
caaccagatt gacatcatat t                                              21

SEQ ID NO: 10          moltype = RNA  length = 21
FEATURE                Location/Qualifiers
source                 1..21
                       mol_type = other RNA
                       organism = synthetic construct
modified_base          19..21
                       mod_base = OTHER
                       note = phosphorothioate linkage
modified_base          1
                       mod_base = OTHER
                       note = 2-fluoro-modified nucleoside
modified_base          3
                       mod_base = OTHER
                       note = 2-fluoro-modified nucleoside
modified_base          5
                       mod_base = OTHER
                       note = 2-fluoro-modified nucleoside
modified_base          7..9
                       mod_base = OTHER
                       note = 2-fluoro-modified nucleoside
modified_base          11
                       mod_base = OTHER
                       note = 2-fluoro-modified nucleoside
modified_base          13
                       mod_base = OTHER
                       note = 2-fluoro-modified nucleoside
modified_base          15
                       mod_base = OTHER
                       note = 2-fluoro-modified nucleoside
modified_base          17
                       mod_base = OTHER
                       note = 2-fluoro-modified nucleoside
modified_base          19
                       mod_base = OTHER
                       note = 2-fluoro-modified nucleoside
modified_base          20..21
                       mod_base = OTHER
                       note = 2-O-methyl modified nucleoside
modified_base          2
                       mod_base = OTHER
                       note = 2-O-methyl modified nucleoside
modified_base          4
                       mod_base = OTHER
                       note = 2-O-methyl modified nucleoside
modified_base          6
                       mod_base = OTHER
                       note = 2-O-methyl modified nucleoside
modified_base          10
                       mod_base = OTHER
                       note = 2-O-methyl modified nucleoside
modified_base          12
                       mod_base = OTHER
                       note = 2-O-methyl modified nucleoside
modified_base          14
                       mod_base = OTHER
                       note = 2-O-methyl modified nucleoside
modified_base          16
                       mod_base = OTHER
                       note = 2-O-methyl modified nucleoside
modified_base          18
                       mod_base = OTHER
                       note = 2-O-methyl modified nucleoside
SEQUENCE: 10
caaccagatt gacatcatgt t                                              21
```

```
SEQ ID NO: 11           moltype = RNA  length = 21
FEATURE                 Location/Qualifiers
source                  1..21
                        mol_type = other RNA
                        organism = synthetic construct
modified_base           19..21
                        mod_base = OTHER
                        note = phosphorothioate linkage
modified_base           1
                        mod_base = OTHER
                        note = 2-fluoro-modified nucleoside
modified_base           3
                        mod_base = OTHER
                        note = 2-fluoro-modified nucleoside
modified_base           5
                        mod_base = OTHER
                        note = 2-fluoro-modified nucleoside
modified_base           7..9
                        mod_base = OTHER
                        note = 2-fluoro-modified nucleoside
modified_base           11
                        mod_base = OTHER
                        note = 2-fluoro-modified nucleoside
modified_base           13
                        mod_base = OTHER
                        note = 2-fluoro-modified nucleoside
modified_base           15
                        mod_base = OTHER
                        note = 2-fluoro-modified nucleoside
modified_base           17
                        mod_base = OTHER
                        note = 2-fluoro-modified nucleoside
modified_base           19
                        mod_base = OTHER
                        note = 2-fluoro-modified nucleoside
modified_base           20..21
                        mod_base = OTHER
                        note = 2-O-methyl modified nucleoside
modified_base           2
                        mod_base = OTHER
                        note = 2-O-methyl modified nucleoside
modified_base           4
                        mod_base = OTHER
                        note = 2-O-methyl modified nucleoside
modified_base           6
                        mod_base = OTHER
                        note = 2-O-methyl modified nucleoside
modified_base           10
                        mod_base = OTHER
                        note = 2-O-methyl modified nucleoside
modified_base           12
                        mod_base = OTHER
                        note = 2-O-methyl modified nucleoside
modified_base           14
                        mod_base = OTHER
                        note = 2-O-methyl modified nucleoside
modified_base           16
                        mod_base = OTHER
                        note = 2-O-methyl modified nucleoside
modified_base           18
                        mod_base = OTHER
                        note = 2-O-methyl modified nucleoside
SEQUENCE: 11
caaccagatt gacatcatat t                                                 21

SEQ ID NO: 12           moltype = RNA  length = 21
FEATURE                 Location/Qualifiers
source                  1..21
                        mol_type = other RNA
                        organism = synthetic construct
modified_base           7..9
                        mod_base = OTHER
                        note = 2-fluoro-modified nucleoside
modified_base           1
                        mod_base = OTHER
                        note = 2-fluoro-modified nucleoside
```

| | | |
|---|---|---|
| modified_base | 3 | |
| | mod_base = OTHER | |
| | note = 2-fluoro-modified nucleoside | |
| modified_base | 5 | |
| | mod_base = OTHER | |
| | note = 2-fluoro-modified nucleoside | |
| modified_base | 11 | |
| | mod_base = OTHER | |
| | note = 2-fluoro-modified nucleoside | |
| modified_base | 13 | |
| | mod_base = OTHER | |
| | note = 2-fluoro-modified nucleoside | |
| modified_base | 15 | |
| | mod_base = OTHER | |
| | note = 2-fluoro-modified nucleoside | |
| modified_base | 17 | |
| | mod_base = OTHER | |
| | note = 2-fluoro-modified nucleoside | |
| modified_base | 19 | |
| | mod_base = OTHER | |
| | note = 2-fluoro-modified nucleoside | |
| modified_base | 19..21 | |
| | mod_base = OTHER | |
| | note = phosphorothioate linkage | |
| modified_base | 20..21 | |
| | mod_base = OTHER | |
| | note = 2-O-methyl modified nucleoside | |
| modified_base | 2 | |
| | mod_base = OTHER | |
| | note = 2-O-methyl modified nucleoside | |
| modified_base | 4 | |
| | mod_base = OTHER | |
| | note = 2-O-methyl modified nucleoside | |
| modified_base | 6 | |
| | mod_base = OTHER | |
| | note = 2-O-methyl modified nucleoside | |
| modified_base | 10 | |
| | mod_base = OTHER | |
| | note = 2-O-methyl modified nucleoside | |
| modified_base | 12 | |
| | mod_base = OTHER | |
| | note = 2-O-methyl modified nucleoside | |
| modified_base | 14 | |
| | mod_base = OTHER | |
| | note = 2-O-methyl modified nucleoside | |
| modified_base | 16 | |
| | mod_base = OTHER | |
| | note = 2-O-methyl modified nucleoside | |
| modified_base | 18 | |
| | mod_base = OTHER | |
| | note = 2-O-methyl modified nucleoside | |
| SEQUENCE: 12 | | |
| caaccagatt gacatcatat t | | 21 |
| | | |
| SEQ ID NO: 13 | moltype = RNA  length = 21 | |
| FEATURE | Location/Qualifiers | |
| source | 1..21 | |
| | mol_type = other RNA | |
| | organism = synthetic construct | |
| modified_base | 19..21 | |
| | mod_base = OTHER | |
| | note = phosphorothioate linkage | |
| modified_base | 1 | |
| | mod_base = OTHER | |
| | note = 2-fluoro-modified nucleoside | |
| modified_base | 3 | |
| | mod_base = OTHER | |
| | note = 2-fluoro-modified nucleoside | |
| modified_base | 5 | |
| | mod_base = OTHER | |
| | note = 2-fluoro-modified nucleoside | |
| modified_base | 7..9 | |
| | mod_base = OTHER | |
| | note = 2-fluoro-modified nucleoside | |
| modified_base | 11 | |
| | mod_base = OTHER | |
| | note = 2-fluoro-modified nucleoside | |

```
modified_base          13
                       mod_base = OTHER
                       note = 2-fluoro-modified nucleoside
modified_base          15
                       mod_base = OTHER
                       note = 2-fluoro-modified nucleoside
modified_base          17
                       mod_base = OTHER
                       note = 2-fluoro-modified nucleoside
modified_base          19
                       mod_base = OTHER
                       note = 2-fluoro-modified nucleoside
modified_base          20..21
                       mod_base = OTHER
                       note = 2-O-methyl modified nucleoside
modified_base          2
                       mod_base = OTHER
                       note = 2-O-methyl modified nucleoside
modified_base          4
                       mod_base = OTHER
                       note = 2-O-methyl modified nucleoside
modified_base          6
                       mod_base = OTHER
                       note = 2-O-methyl modified nucleoside
modified_base          10
                       mod_base = OTHER
                       note = 2-O-methyl modified nucleoside
modified_base          12
                       mod_base = OTHER
                       note = 2-O-methyl modified nucleoside
modified_base          14
                       mod_base = OTHER
                       note = 2-O-methyl modified nucleoside
modified_base          16
                       mod_base = OTHER
                       note = 2-O-methyl modified nucleoside
modified_base          18
                       mod_base = OTHER
                       note = 2-O-methyl modified nucleoside
SEQUENCE: 13
caaccagatt gacatcatat t                                            21

SEQ ID NO: 14          moltype = RNA   length = 21
FEATURE                Location/Qualifiers
source                 1..21
                       mol_type = other RNA
                       organism = synthetic construct
modified_base          19..21
                       mod_base = OTHER
                       note = phosphorothioate linkage
modified_base          1
                       mod_base = OTHER
                       note = 2-fluoro-modified nucleoside
modified_base          3
                       mod_base = OTHER
                       note = 2-fluoro-modified nucleoside
modified_base          5
                       mod_base = OTHER
                       note = 2-fluoro-modified nucleoside
modified_base          7..9
                       mod_base = OTHER
                       note = 2-fluoro-modified nucleoside
modified_base          11
                       mod_base = OTHER
                       note = 2-fluoro-modified nucleoside
modified_base          13
                       mod_base = OTHER
                       note = 2-fluoro-modified nucleoside
modified_base          15
                       mod_base = OTHER
                       note = 2-fluoro-modified nucleoside
modified_base          17
                       mod_base = OTHER
                       note = 2-fluoro-modified nucleoside
modified_base          19
                       mod_base = OTHER
                       note = 2-fluoro-modified nucleoside
```

```
modified_base          20..21
                       mod_base = OTHER
                       note = 2-O-methyl modified nucleoside
modified_base          18
                       mod_base = OTHER
                       note = 2-O-methyl modified nucleoside
modified_base          16
                       mod_base = OTHER
                       note = 2-O-methyl modified nucleoside
modified_base          14
                       mod_base = OTHER
                       note = 2-O-methyl modified nucleoside
modified_base          12
                       mod_base = OTHER
                       note = 2-O-methyl modified nucleoside
modified_base          10
                       mod_base = OTHER
                       note = 2-O-methyl modified nucleoside
modified_base          4
                       mod_base = OTHER
                       note = 2-O-methyl modified nucleoside
modified_base          6
                       mod_base = OTHER
                       note = 2-O-methyl modified nucleoside
modified_base          2
                       mod_base = OTHER
                       note = 2-O-methyl modified nucleoside
SEQUENCE: 14
caaccagatt gacatcatat t                                               21

SEQ ID NO: 15          moltype = RNA   length = 21
FEATURE                Location/Qualifiers
source                 1..21
                       mol_type = other RNA
                       organism = synthetic construct
modified_base          1..3
                       mod_base = OTHER
                       note = phosphorothioate linkage
modified_base          19..21
                       mod_base = OTHER
                       note = phosphorothioate linkage
modified_base          7..9
                       mod_base = OTHER
                       note = 2-fluoro-modified nucleoside
modified_base          1
                       mod_base = OTHER
                       note = 2-fluoro-modified nucleoside
modified_base          3
                       mod_base = OTHER
                       note = 2-fluoro-modified nucleoside
modified_base          5
                       mod_base = OTHER
                       note = 2-fluoro-modified nucleoside
modified_base          11
                       mod_base = OTHER
                       note = 2-fluoro-modified nucleoside
modified_base          13
                       mod_base = OTHER
                       note = 2-fluoro-modified nucleoside
modified_base          15
                       mod_base = OTHER
                       note = 2-fluoro-modified nucleoside
modified_base          17
                       mod_base = OTHER
                       note = 2-fluoro-modified nucleoside
modified_base          19
                       mod_base = OTHER
                       note = 2-fluoro-modified nucleoside
modified_base          20..21
                       mod_base = OTHER
                       note = 2-O-methyl modified nucleoside
modified_base          2
                       mod_base = OTHER
                       note = 2-O-methyl modified nucleoside
modified_base          4
                       mod_base = OTHER
                       note = 2-O-methyl modified nucleoside
```

```
modified_base        6
                     mod_base = OTHER
                     note = 2-O-methyl modified nucleoside
modified_base        10
                     mod_base = OTHER
                     note = 2-O-methyl modified nucleoside
modified_base        12
                     mod_base = OTHER
                     note = 2-O-methyl modified nucleoside
modified_base        14
                     mod_base = OTHER
                     note = 2-O-methyl modified nucleoside
modified_base        16
                     mod_base = OTHER
                     note = 2-O-methyl modified nucleoside
modified_base        18
                     mod_base = OTHER
                     note = 2-O-methyl modified nucleoside
SEQUENCE: 15
caaccagatt gacatcatgt t                                                      21

SEQ ID NO: 16        moltype = RNA   length = 21
FEATURE              Location/Qualifiers
source               1..21
                     mol_type = other RNA
                     organism = synthetic construct
modified_base        1..3
                     mod_base = OTHER
                     note = phosphorothioate linkage
modified_base        19..21
                     mod_base = OTHER
                     note = phosphorothioate linkage
modified_base        7..9
                     mod_base = OTHER
                     note = 2-fluoro-modified nucleoside
modified_base        1
                     mod_base = OTHER
                     note = 2-fluoro-modified nucleoside
modified_base        3
                     mod_base = OTHER
                     note = 2-fluoro-modified nucleoside
modified_base        5
                     mod_base = OTHER
                     note = 2-fluoro-modified nucleoside
modified_base        11
                     mod_base = OTHER
                     note = 2-fluoro-modified nucleoside
modified_base        13
                     mod_base = OTHER
                     note = 2-fluoro-modified nucleoside
modified_base        15
                     mod_base = OTHER
                     note = 2-fluoro-modified nucleoside
modified_base        17
                     mod_base = OTHER
                     note = 2-fluoro-modified nucleoside
modified_base        19
                     mod_base = OTHER
                     note = 2-fluoro-modified nucleoside
modified_base        20..21
                     mod_base = OTHER
                     note = 2-O-methyl modified nucleoside
modified_base        2
                     mod_base = OTHER
                     note = 2-O-methyl modified nucleoside
modified_base        4
                     mod_base = OTHER
                     note = 2-O-methyl modified nucleoside
modified_base        6
                     mod_base = OTHER
                     note = 2-O-methyl modified nucleoside
modified_base        10
                     mod_base = OTHER
                     note = 2-O-methyl modified nucleoside
modified_base        12
                     mod_base = OTHER
                     note = 2-O-methyl modified nucleoside
```

```
modified_base          14
                       mod_base = OTHER
                       note = 2-O-methyl modified nucleoside
modified_base          16
                       mod_base = OTHER
                       note = 2-O-methyl modified nucleoside
modified_base          18
                       mod_base = OTHER
                       note = 2-O-methyl modified nucleoside
SEQUENCE: 16
caaccagatt gacatcatgt t                                          21

SEQ ID NO: 17          moltype = RNA   length = 21
FEATURE                Location/Qualifiers
source                 1..21
                       mol_type = other RNA
                       organism = synthetic construct
modified_base          1..3
                       mod_base = OTHER
                       note = phosphorothioate linkage
modified_base          19..21
                       mod_base = OTHER
                       note = phosphorothioate linkage
modified_base          7..9
                       mod_base = OTHER
                       note = 2-fluoro-modified nucleoside
modified_base          1
                       mod_base = OTHER
                       note = 2-fluoro-modified nucleoside
modified_base          3
                       mod_base = OTHER
                       note = 2-fluoro-modified nucleoside
modified_base          5
                       mod_base = OTHER
                       note = 2-fluoro-modified nucleoside
modified_base          11
                       mod_base = OTHER
                       note = 2-fluoro-modified nucleoside
modified_base          13
                       mod_base = OTHER
                       note = 2-fluoro-modified nucleoside
modified_base          15
                       mod_base = OTHER
                       note = 2-fluoro-modified nucleoside
modified_base          17
                       mod_base = OTHER
                       note = 2-fluoro-modified nucleoside
modified_base          19
                       mod_base = OTHER
                       note = 2-fluoro-modified nucleoside
modified_base          20..21
                       mod_base = OTHER
                       note = 2-O-methyl modified nucleoside
modified_base          2
                       mod_base = OTHER
                       note = 2-O-methyl modified nucleoside
modified_base          4
                       mod_base = OTHER
                       note = 2-O-methyl modified nucleoside
modified_base          6
                       mod_base = OTHER
                       note = 2-O-methyl modified nucleoside
modified_base          10
                       mod_base = OTHER
                       note = 2-O-methyl modified nucleoside
modified_base          12
                       mod_base = OTHER
                       note = 2-O-methyl modified nucleoside
modified_base          14
                       mod_base = OTHER
                       note = 2-O-methyl modified nucleoside
modified_base          16
                       mod_base = OTHER
                       note = 2-O-methyl modified nucleoside
modified_base          18
                       mod_base = OTHER
                       note = 2-O-methyl modified nucleoside
SEQUENCE: 17
caaccagatt gacatcatgt t                                          21
```

```
SEQ ID NO: 18              moltype = RNA  length = 21
FEATURE                    Location/Qualifiers
source                     1..21
                           mol_type = other RNA
                           organism = synthetic construct
modified_base              1..3
                           mod_base = OTHER
                           note = phosphorothioate linkage
modified_base              19..21
                           mod_base = OTHER
                           note = phosphorothioate linkage
modified_base              7..9
                           mod_base = OTHER
                           note = 2-fluoro-modified nucleoside
modified_base              1
                           mod_base = OTHER
                           note = 2-fluoro-modified nucleoside
modified_base              3
                           mod_base = OTHER
                           note = 2-fluoro-modified nucleoside
modified_base              5
                           mod_base = OTHER
                           note = 2-fluoro-modified nucleoside
modified_base              11
                           mod_base = OTHER
                           note = 2-fluoro-modified nucleoside
modified_base              13
                           mod_base = OTHER
                           note = 2-fluoro-modified nucleoside
modified_base              15
                           mod_base = OTHER
                           note = 2-fluoro-modified nucleoside
modified_base              17
                           mod_base = OTHER
                           note = 2-fluoro-modified nucleoside
modified_base              19
                           mod_base = OTHER
                           note = 2-fluoro-modified nucleoside
modified_base              20..21
                           mod_base = OTHER
                           note = 2-O-methyl modified nucleoside
modified_base              2
                           mod_base = OTHER
                           note = 2-O-methyl modified nucleoside
modified_base              4
                           mod_base = OTHER
                           note = 2-O-methyl modified nucleoside
modified_base              6
                           mod_base = OTHER
                           note = 2-O-methyl modified nucleoside
modified_base              14
                           mod_base = OTHER
                           note = 2-O-methyl modified nucleoside
modified_base              10
                           mod_base = OTHER
                           note = 2-O-methyl modified nucleoside
modified_base              12
                           mod_base = OTHER
                           note = 2-O-methyl modified nucleoside
modified_base              16
                           mod_base = OTHER
                           note = 2-O-methyl modified nucleoside
modified_base              18
                           mod_base = OTHER
                           note = 2-O-methyl modified nucleoside
SEQUENCE: 18
caaccagatt gacatcatgt t                                                    21

SEQ ID NO: 19              moltype = RNA  length = 21
FEATURE                    Location/Qualifiers
source                     1..21
                           mol_type = other RNA
                           organism = synthetic construct
modified_base              19..21
                           mod_base = OTHER
                           note = phosphorothioate linkage
```

| | | |
|---|---|---|
| modified_base | 7..9<br>mod_base = OTHER<br>note = 2-fluoro-modified nucleoside | |
| modified_base | 1<br>mod_base = OTHER<br>note = 2-fluoro-modified nucleoside | |
| modified_base | 3<br>mod_base = OTHER<br>note = 2-fluoro-modified nucleoside | |
| modified_base | 5<br>mod_base = OTHER<br>note = 2-fluoro-modified nucleoside | |
| modified_base | 11<br>mod_base = OTHER<br>note = 2-fluoro-modified nucleoside | |
| modified_base | 13<br>mod_base = OTHER<br>note = 2-fluoro-modified nucleoside | |
| modified_base | 15<br>mod_base = OTHER<br>note = 2-fluoro-modified nucleoside | |
| modified_base | 17<br>mod_base = OTHER<br>note = 2-fluoro-modified nucleoside | |
| modified_base | 19<br>mod_base = OTHER<br>note = 2-fluoro-modified nucleoside | |
| modified_base | 20..21<br>mod_base = OTHER<br>note = 2-O-methyl modified nucleoside | |
| modified_base | 2<br>mod_base = OTHER<br>note = 2-O-methyl modified nucleoside | |
| modified_base | 4<br>mod_base = OTHER<br>note = 2-O-methyl modified nucleoside | |
| modified_base | 6<br>mod_base = OTHER<br>note = 2-O-methyl modified nucleoside | |
| modified_base | 10<br>mod_base = OTHER<br>note = 2-O-methyl modified nucleoside | |
| modified_base | 12<br>mod_base = OTHER<br>note = 2-O-methyl modified nucleoside | |
| modified_base | 14<br>mod_base = OTHER<br>note = 2-O-methyl modified nucleoside | |
| modified_base | 16<br>mod_base = OTHER<br>note = 2-O-methyl modified nucleoside | |
| modified_base | 18<br>mod_base = OTHER<br>note = 2-O-methyl modified nucleoside | |
| SEQUENCE: 19 | | |
| caaccagatt gacatcatgt t | | 21 |
| SEQ ID NO: 20<br>FEATURE<br>source | moltype = RNA  length = 21<br>Location/Qualifiers<br>1..21<br>mol_type = other RNA<br>organism = synthetic construct | |
| modified_base | 19..21<br>mod_base = OTHER<br>note = phosphorothioate linkage | |
| modified_base | 7..9<br>mod_base = OTHER<br>note = 2-fluoro-modified nucleoside | |
| modified_base | 1<br>mod_base = OTHER<br>note = 2-fluoro-modified nucleoside | |
| modified_base | 3<br>mod_base = OTHER<br>note = 2-fluoro-modified nucleoside | |
| modified_base | 5<br>mod_base = OTHER<br>note = 2-fluoro-modified nucleoside | |

```
modified_base       11
                    mod_base = OTHER
                    note = 2-fluoro-modified nucleoside
modified_base       13
                    mod_base = OTHER
                    note = 2-fluoro-modified nucleoside
modified_base       15
                    mod_base = OTHER
                    note = 2-fluoro-modified nucleoside
modified_base       17
                    mod_base = OTHER
                    note = 2-fluoro-modified nucleoside
modified_base       19
                    mod_base = OTHER
                    note = 2-fluoro-modified nucleoside
modified_base       20..21
                    mod_base = OTHER
                    note = 2-O-methyl modified nucleoside
modified_base       2
                    mod_base = OTHER
                    note = 2-O-methyl modified nucleoside
modified_base       4
                    mod_base = OTHER
                    note = 2-O-methyl modified nucleoside
modified_base       6
                    mod_base = OTHER
                    note = 2-O-methyl modified nucleoside
modified_base       10
                    mod_base = OTHER
                    note = 2-O-methyl modified nucleoside
modified_base       12
                    mod_base = OTHER
                    note = 2-O-methyl modified nucleoside
modified_base       14
                    mod_base = OTHER
                    note = 2-O-methyl modified nucleoside
modified_base       16
                    mod_base = OTHER
                    note = 2-O-methyl modified nucleoside
modified_base       18
                    mod_base = OTHER
                    note = 2-O-methyl modified nucleoside
SEQUENCE: 20
caaccagatt gacatcatgt t                                              21

SEQ ID NO: 21          moltype = RNA   length = 21
FEATURE                Location/Qualifiers
source                 1..21
                       mol_type = other RNA
                       organism = synthetic construct
modified_base          19..21
                       mod_base = OTHER
                       note = phosphorothioate linkage
modified_base          7..9
                       mod_base = OTHER
                       note = 2-fluoro-modified nucleoside
modified_base          1
                       mod_base = OTHER
                       note = 2-fluoro-modified nucleoside
modified_base          3
                       mod_base = OTHER
                       note = 2-fluoro-modified nucleoside
modified_base          5
                       mod_base = OTHER
                       note = 2-fluoro-modified nucleoside
modified_base          11
                       mod_base = OTHER
                       note = 2-fluoro-modified nucleoside
modified_base          13
                       mod_base = OTHER
                       note = 2-fluoro-modified nucleoside
modified_base          15
                       mod_base = OTHER
                       note = 2-fluoro-modified nucleoside
modified_base          17
                       mod_base = OTHER
                       note = 2-fluoro-modified nucleoside
```

| | | |
|---|---|---|
| modified_base | 19 | |
| | mod_base = OTHER | |
| | note = 2-fluoro-modified nucleoside | |
| modified_base | 20..21 | |
| | mod_base = OTHER | |
| | note = 2-O-methyl modified nucleoside | |
| modified_base | 2 | |
| | mod_base = OTHER | |
| | note = 2-O-methyl modified nucleoside | |
| modified_base | 4 | |
| | mod_base = OTHER | |
| | note = 2-O-methyl modified nucleoside | |
| modified_base | 6 | |
| | mod_base = OTHER | |
| | note = 2-O-methyl modified nucleoside | |
| modified_base | 12 | |
| | mod_base = OTHER | |
| | note = 2-O-methyl modified nucleoside | |
| modified_base | 10 | |
| | mod_base = OTHER | |
| | note = 2-O-methyl modified nucleoside | |
| modified_base | 14 | |
| | mod_base = OTHER | |
| | note = 2-O-methyl modified nucleoside | |
| modified_base | 16 | |
| | mod_base = OTHER | |
| | note = 2-O-methyl modified nucleoside | |
| modified_base | 18 | |
| | mod_base = OTHER | |
| | note = 2-O-methyl modified nucleoside | |
| SEQUENCE: 21 | | |
| caaccagatt gacatcatgt t | | 21 |
| | | |
| SEQ ID NO: 22 | moltype = RNA   length = 21 | |
| FEATURE | Location/Qualifiers | |
| source | 1..21 | |
| | mol_type = other RNA | |
| | organism = synthetic construct | |
| modified_base | 19..21 | |
| | mod_base = OTHER | |
| | note = phosphorothioate linkage | |
| modified_base | 3 | |
| | mod_base = OTHER | |
| | note = 2-fluoro-modified nucleoside | |
| modified_base | 5 | |
| | mod_base = OTHER | |
| | note = 2-fluoro-modified nucleoside | |
| modified_base | 7 | |
| | mod_base = OTHER | |
| | note = 2-fluoro-modified nucleoside | |
| modified_base | 11 | |
| | mod_base = OTHER | |
| | note = 2-fluoro-modified nucleoside | |
| modified_base | 13 | |
| | mod_base = OTHER | |
| | note = 2-fluoro-modified nucleoside | |
| modified_base | 15 | |
| | mod_base = OTHER | |
| | note = 2-fluoro-modified nucleoside | |
| modified_base | 17 | |
| | mod_base = OTHER | |
| | note = 2-fluoro-modified nucleoside | |
| modified_base | 19 | |
| | mod_base = OTHER | |
| | note = 2-fluoro-modified nucleoside | |
| modified_base | 9 | |
| | mod_base = OTHER | |
| | note = 2-fluoro-modified nucleoside | |
| modified_base | 14..16 | |
| | mod_base = OTHER | |
| | note = 2-O-methyl modified nucleoside | |
| modified_base | 20..21 | |
| | mod_base = OTHER | |
| | note = 2-O-methyl modified nucleoside | |
| modified_base | 1..2 | |
| | mod_base = OTHER | |
| | note = 2-O-methyl modified nucleoside | |

```
                    modified_base      18
                                       mod_base = OTHER
                                       note = 2-O-methyl modified nucleoside
                    modified_base      12
                                       mod_base = OTHER
                                       note = 2-O-methyl modified nucleoside
                    modified_base      4
                                       mod_base = OTHER
                                       note = 2-O-methyl modified nucleoside
                    modified_base      6
                                       mod_base = OTHER
                                       note = 2-O-methyl modified nucleoside
                    modified_base      8
                                       mod_base = OTHER
                                       note = 2-O-methyl modified nucleoside
                    modified_base      10
                                       mod_base = OTHER
                                       note = 2-O-methyl modified nucleoside
SEQUENCE: 22
ctacaaaggt gaactcagat t                                                     21

SEQ ID NO: 23       moltype = RNA   length = 21
FEATURE             Location/Qualifiers
source              1..21
                    mol_type = other RNA
                    organism = synthetic construct
                    modified_base      19..21
                                       mod_base = OTHER
                                       note = phosphorothioate linkage
                    modified_base      3
                                       mod_base = OTHER
                                       note = 2-fluoro-modified nucleoside
                    modified_base      5
                                       mod_base = OTHER
                                       note = 2-fluoro-modified nucleoside
                    modified_base      7
                                       mod_base = OTHER
                                       note = 2-fluoro-modified nucleoside
                    modified_base      9
                                       mod_base = OTHER
                                       note = 2-fluoro-modified nucleoside
                    modified_base      11
                                       mod_base = OTHER
                                       note = 2-fluoro-modified nucleoside
                    modified_base      13
                                       mod_base = OTHER
                                       note = 2-fluoro-modified nucleoside
                    modified_base      14..16
                                       mod_base = OTHER
                                       note = 2-O-methyl modified nucleoside
                    modified_base      17
                                       mod_base = OTHER
                                       note = 2-fluoro-modified nucleoside
                    modified_base      19
                                       mod_base = OTHER
                                       note = 2-fluoro-modified nucleoside
                    modified_base      1..2
                                       mod_base = OTHER
                                       note = 2-O-methyl modified nucleoside
                    modified_base      20..21
                                       mod_base = OTHER
                                       note = 2-O-methyl modified nucleoside
                    modified_base      18
                                       mod_base = OTHER
                                       note = 2-O-methyl modified nucleoside
                    modified_base      4
                                       mod_base = OTHER
                                       note = 2-O-methyl modified nucleoside
                    modified_base      6
                                       mod_base = OTHER
                                       note = 2-O-methyl modified nucleoside
                    modified_base      8
                                       mod_base = OTHER
                                       note = 2-O-methyl modified nucleoside
                    modified_base      10
                                       mod_base = OTHER
                                       note = 2-O-methyl modified nucleoside
```

```
                        modified_base           12
                                                mod_base = OTHER
                                                note = 2-O-methyl modified nucleoside
                        SEQUENCE: 23
                        ctacaaaggt gaactcagat t                                              21

SEQ ID NO: 24           moltype = RNA   length = 21
                        FEATURE                 Location/Qualifiers
                        source                  1..21
                                                mol_type = other RNA
                                                organism = synthetic construct
                        modified_base           1..3
                                                mod_base = OTHER
                                                note = phosphorothioate linkage
                        modified_base           19..21
                                                mod_base = OTHER
                                                note = 2-O-methyl modified nucleoside
                                                note = phosphorothioate linkage
                        modified_base           2
                                                mod_base = OTHER
                                                note = 2-fluoro-modified nucleoside
                        modified_base           4
                                                mod_base = OTHER
                                                note = 2-fluoro-modified nucleoside
                        modified_base           6
                                                mod_base = OTHER
                                                note = 2-fluoro-modified nucleoside
                        modified_base           8
                                                mod_base = OTHER
                                                note = 2-fluoro-modified nucleoside
                        modified_base           10
                                                mod_base = OTHER
                                                note = 2-fluoro-modified nucleoside
                        modified_base           14
                                                mod_base = OTHER
                                                note = 2-fluoro-modified nucleoside
                        modified_base           16
                                                mod_base = OTHER
                                                note = 2-fluoro-modified nucleoside
                        modified_base           18
                                                mod_base = OTHER
                                                note = 2-fluoro-modified nucleoside
                        modified_base           11..13
                                                mod_base = OTHER
                                                note = 2-O-methyl modified nucleoside
                        modified_base           15
                                                mod_base = OTHER
                                                note = 2-O-methyl modified nucleoside
                        modified_base           17
                                                mod_base = OTHER
                                                note = 2-O-methyl modified nucleoside
                        modified_base           1
                                                mod_base = OTHER
                                                note = 2-O-methyl modified nucleoside
                        modified_base           3
                                                mod_base = OTHER
                                                note = 2-O-methyl modified nucleoside
                        modified_base           5
                                                mod_base = OTHER
                                                note = 2-O-methyl modified nucleoside
                        modified_base           7
                                                mod_base = OTHER
                                                note = 2-O-methyl modified nucleoside
                        modified_base           9
                                                mod_base = OTHER
                                                note = 2-O-methyl modified nucleoside
                        SEQUENCE: 24
                        catgatgtca atctggttgt t                                              21

SEQ ID NO: 25           moltype = RNA   length = 21
                        FEATURE                 Location/Qualifiers
                        source                  1..21
                                                mol_type = other RNA
                                                organism = synthetic construct
                        modified_base           1..3
                                                mod_base = OTHER
                                                note = phosphorothioate linkage
```

|                | |                                              |
|----------------|-|----------------------------------------------|
| modified_base  | | 19..21<br>mod_base = OTHER<br>note = phosphorothioate linkage<br>note = 2-O-methyl modified nucleoside |
| modified_base  | | 2<br>mod_base = OTHER<br>note = 2-fluoro-modified nucleoside |
| modified_base  | | 4<br>mod_base = OTHER<br>note = 2-fluoro-modified nucleoside |
| modified_base  | | 6<br>mod_base = OTHER<br>note = 2-fluoro-modified nucleoside |
| modified_base  | | 8<br>mod_base = OTHER<br>note = 2-fluoro-modified nucleoside |
| modified_base  | | 10<br>mod_base = OTHER<br>note = 2-fluoro-modified nucleoside |
| modified_base  | | 14<br>mod_base = OTHER<br>note = 2-fluoro-modified nucleoside |
| modified_base  | | 16<br>mod_base = OTHER<br>note = 2-fluoro-modified nucleoside |
| modified_base  | | 18<br>mod_base = OTHER<br>note = 2-fluoro-modified nucleoside |
| modified_base  | | 11..13<br>mod_base = OTHER<br>note = 2-O-methyl modified nucleoside |
| modified_base  | | 1<br>mod_base = OTHER<br>note = 2-O-methyl modified nucleoside |
| modified_base  | | 3<br>mod_base = OTHER<br>note = 2-O-methyl modified nucleoside |
| modified_base  | | 5<br>mod_base = OTHER<br>note = 2-O-methyl modified nucleoside |
| modified_base  | | 7<br>mod_base = OTHER<br>note = 2-O-methyl modified nucleoside |
| modified_base  | | 9<br>mod_base = OTHER<br>note = 2-O-methyl modified nucleoside |
| modified_base  | | 15<br>mod_base = OTHER<br>note = 2-O-methyl modified nucleoside |
| modified_base  | | 17<br>mod_base = OTHER<br>note = 2-O-methyl modified nucleoside |
| SEQUENCE: 25   | | |
| catgatgtca atctggttgt t | | 21 |
| SEQ ID NO: 26<br>FEATURE | | moltype = RNA  length = 21<br>Location/Qualifiers |
| source         | | 1..21<br>mol_type = other RNA<br>organism = synthetic construct |
| modified_base  | | 1..3<br>mod_base = OTHER<br>note = phosphorothioate linkage |
| modified_base  | | 19..21<br>mod_base = OTHER<br>note = 2-O-methyl modified nucleoside<br>note = phosphorothioate linkage |
| modified_base  | | 2<br>mod_base = OTHER<br>note = 2-fluoro-modified nucleoside |
| modified_base  | | 4<br>mod_base = OTHER<br>note = 2-fluoro-modified nucleoside |
| modified_base  | | 6<br>mod_base = OTHER<br>note = 2-fluoro-modified nucleoside |
| modified_base  | | 8<br>mod_base = OTHER<br>note = 2-fluoro-modified nucleoside |

-continued

| | | |
|---|---|---|
| modified_base | 10 | |
| | mod_base = OTHER | |
| | note = 2-fluoro-modified nucleoside | |
| modified_base | 14 | |
| | mod_base = OTHER | |
| | note = 2-fluoro-modified nucleoside | |
| modified_base | 16 | |
| | mod_base = OTHER | |
| | note = 2-fluoro-modified nucleoside | |
| modified_base | 18 | |
| | mod_base = OTHER | |
| | note = 2-fluoro-modified nucleoside | |
| modified_base | 11..13 | |
| | mod_base = OTHER | |
| | note = 2-O-methyl modified nucleoside | |
| modified_base | 15 | |
| | mod_base = OTHER | |
| | note = 2-O-methyl modified nucleoside | |
| modified_base | 17 | |
| | mod_base = OTHER | |
| | note = 2-O-methyl modified nucleoside | |
| modified_base | 1 | |
| | mod_base = OTHER | |
| | note = 2-O-methyl modified nucleoside | |
| modified_base | 3 | |
| | mod_base = OTHER | |
| | note = 2-O-methyl modified nucleoside | |
| modified_base | 5 | |
| | mod_base = OTHER | |
| | note = 2-O-methyl modified nucleoside | |
| modified_base | 7 | |
| | mod_base = OTHER | |
| | note = 2-O-methyl modified nucleoside | |
| modified_base | 9 | |
| | mod_base = OTHER | |
| | note = 2-O-methyl modified nucleoside | |
| SEQUENCE: 26 | | |
| catgatgtca atctggttgt t | | 21 |
| SEQ ID NO: 27 | moltype = RNA  length = 21 | |
| FEATURE | Location/Qualifiers | |
| source | 1..21 | |
| | mol_type = other RNA | |
| | organism = synthetic construct | |
| modified_base | 1..3 | |
| | mod_base = OTHER | |
| | note = phosphorothioate linkage | |
| modified_base | 19..21 | |
| | mod_base = OTHER | |
| | note = phosphorothioate linkage | |
| | note = 2-O-methyl modified nucleoside | |
| modified_base | 2 | |
| | mod_base = OTHER | |
| | note = 2-fluoro-modified nucleoside | |
| modified_base | 4 | |
| | mod_base = OTHER | |
| | note = 2-fluoro-modified nucleoside | |
| modified_base | 6 | |
| | mod_base = OTHER | |
| | note = 2-fluoro-modified nucleoside | |
| modified_base | 8 | |
| | mod_base = OTHER | |
| | note = 2-fluoro-modified nucleoside | |
| modified_base | 10 | |
| | mod_base = OTHER | |
| | note = 2-fluoro-modified nucleoside | |
| modified_base | 12 | |
| | mod_base = OTHER | |
| | note = 2-fluoro-modified nucleoside | |
| modified_base | 14 | |
| | mod_base = OTHER | |
| | note = 2-fluoro-modified nucleoside | |
| modified_base | 16 | |
| | mod_base = OTHER | |
| | note = 2-fluoro-modified nucleoside | |
| modified_base | 18 | |
| | mod_base = OTHER | |
| | note = 2-fluoro-modified nucleoside | |

```
modified_base      1
                   mod_base = OTHER
                   note = 2-O-methyl modified nucleoside
modified_base      3
                   mod_base = OTHER
                   note = 2-O-methyl modified nucleoside
modified_base      5
                   mod_base = OTHER
                   note = 2-O-methyl modified nucleoside
modified_base      7
                   mod_base = OTHER
                   note = 2-O-methyl modified nucleoside
modified_base      9
                   mod_base = OTHER
                   note = 2-O-methyl modified nucleoside
modified_base      11
                   mod_base = OTHER
                   note = 2-O-methyl modified nucleoside
modified_base      13
                   mod_base = OTHER
                   note = 2-O-methyl modified nucleoside
modified_base      15
                   mod_base = OTHER
                   note = 2-O-methyl modified nucleoside
modified_base      17
                   mod_base = OTHER
                   note = 2-O-methyl modified nucleoside
SEQUENCE: 27
ttgtcgagaa agagtgttgt t                                         21

SEQ ID NO: 28      moltype = RNA   length = 21
FEATURE            Location/Qualifiers
source             1..21
                   mol_type = other RNA
                   organism = synthetic construct
modified_base      1..3
                   mod_base = OTHER
                   note = phosphorothioate linkage
modified_base      19..21
                   mod_base = OTHER
                   note = 2-O-methyl modified nucleoside
                   note = phosphorothioate linkage
modified_base      1
                   mod_base = OTHER
                   note = 5-vinylphosphonate
                   note = 2-O-methyl modified nucleoside
modified_base      2
                   mod_base = OTHER
                   note = 2-fluoro-modified nucleoside
modified_base      4
                   mod_base = OTHER
                   note = 2-fluoro-modified nucleoside
modified_base      6
                   mod_base = OTHER
                   note = 2-fluoro-modified nucleoside
modified_base      10
                   mod_base = OTHER
                   note = 2-fluoro-modified nucleoside
modified_base      14
                   mod_base = OTHER
                   note = 2-fluoro-modified nucleoside
modified_base      16
                   mod_base = OTHER
                   note = 2-fluoro-modified nucleoside
modified_base      18
                   mod_base = OTHER
                   note = 2-fluoro-modified nucleoside
modified_base      11..13
                   mod_base = OTHER
                   note = 2-O-methyl modified nucleoside
modified_base      15
                   mod_base = OTHER
                   note = 2-O-methyl modified nucleoside
modified_base      17
                   mod_base = OTHER
                   note = 2-O-methyl modified nucleoside
modified_base      1
                   mod_base = OTHER
                   note = 2-O-methyl modified nucleoside
```

```
modified_base              3
                           mod_base = OTHER
                           note = 2-O-methyl modified nucleoside
modified_base              5
                           mod_base = OTHER
                           note = 2-O-methyl modified nucleoside
modified_base              7
                           mod_base = OTHER
                           note = 2-O-methyl modified nucleoside
modified_base              9
                           mod_base = OTHER
                           note = 2-O-methyl modified nucleoside
SEQUENCE: 28
tatgatgtca atctggttgt t                                              21

SEQ ID NO: 29              moltype = RNA   length = 21
FEATURE                    Location/Qualifiers
source                     1..21
                           mol_type = other RNA
                           organism = synthetic construct
modified_base              1..3
                           mod_base = OTHER
                           note = phosphorothioate linkage
modified_base              19..21
                           mod_base = OTHER
                           note = phosphorothioate linkage
                           note = 2-O-methyl modified nucleoside
modified_base              2
                           mod_base = OTHER
                           note = 2-fluoro-modified nucleoside
modified_base              4
                           mod_base = OTHER
                           note = 2-fluoro-modified nucleoside
modified_base              6
                           mod_base = OTHER
                           note = 2-fluoro-modified nucleoside
modified_base              8
                           mod_base = OTHER
                           note = 2-fluoro-modified nucleoside
modified_base              10
                           mod_base = OTHER
                           note = 2-fluoro-modified nucleoside
modified_base              16
                           mod_base = OTHER
                           note = 2-fluoro-modified nucleoside
modified_base              14
                           mod_base = OTHER
                           note = 2-fluoro-modified nucleoside
modified_base              18
                           mod_base = OTHER
                           note = 2-fluoro-modified nucleoside
modified_base              11..13
                           mod_base = OTHER
                           note = 2-O-methyl modified nucleoside
modified_base              15
                           mod_base = OTHER
                           note = 2-O-methyl modified nucleoside
modified_base              17
                           mod_base = OTHER
                           note = 2-O-methyl modified nucleoside
modified_base              1
                           mod_base = OTHER
                           note = 2-O-methyl modified nucleoside
modified_base              3
                           mod_base = OTHER
                           note = 2-O-methyl modified nucleoside
modified_base              5
                           mod_base = OTHER
                           note = 2-O-methyl modified nucleoside
modified_base              7
                           mod_base = OTHER
                           note = 2-O-methyl modified nucleoside
modified_base              9
                           mod_base = OTHER
                           note = 2-O-methyl modified nucleoside
SEQUENCE: 29
tatgatgtca atctggttgt t                                              21
```

```
SEQ ID NO: 30            moltype = RNA  length = 21
FEATURE                  Location/Qualifiers
source                   1..21
                         mol_type = other RNA
                         organism = synthetic construct
modified_base            1..3
                         mod_base = OTHER
                         note = phosphorothioate linkage
modified_base            19..21
                         mod_base = OTHER
                         note = phosphorothioate linkage
                         note = 2-O-methyl modified nucleoside
modified_base            1
                         mod_base = OTHER
                         note = 5-vinylphosphonate
                         note = 2-O-methyl modified nucleoside
modified_base            2
                         mod_base = OTHER
                         note = 2-fluoro-modified nucleoside
modified_base            4
                         mod_base = OTHER
                         note = 2-fluoro-modified nucleoside
modified_base            6
                         mod_base = OTHER
                         note = 2-fluoro-modified nucleoside
modified_base            8
                         mod_base = OTHER
                         note = 2-fluoro-modified nucleoside
modified_base            10
                         mod_base = OTHER
                         note = 2-fluoro-modified nucleoside
modified_base            12
                         mod_base = OTHER
                         note = 2-fluoro-modified nucleoside
modified_base            14
                         mod_base = OTHER
                         note = 2-fluoro-modified nucleoside
modified_base            16
                         mod_base = OTHER
                         note = 2-fluoro-modified nucleoside
modified_base            18
                         mod_base = OTHER
                         note = 2-fluoro-modified nucleoside
modified_base            3
                         mod_base = OTHER
                         note = 2-O-methyl modified nucleoside
modified_base            5
                         mod_base = OTHER
                         note = 2-O-methyl modified nucleoside
modified_base            7
                         mod_base = OTHER
                         note = 2-O-methyl modified nucleoside
modified_base            9
                         mod_base = OTHER
                         note = 2-O-methyl modified nucleoside
modified_base            11
                         mod_base = OTHER
                         note = 2-O-methyl modified nucleoside
modified_base            13
                         mod_base = OTHER
                         note = 2-O-methyl modified nucleoside
modified_base            15
                         mod_base = OTHER
                         note = 2-O-methyl modified nucleoside
modified_base            17
                         mod_base = OTHER
                         note = 2-O-methyl modified nucleoside
SEQUENCE: 30
ttgtcgagaa agagtgttgt t                                            21

SEQ ID NO: 31            moltype = RNA  length = 21
FEATURE                  Location/Qualifiers
source                   1..21
                         mol_type = other RNA
                         organism = synthetic construct
modified_base            1..3
                         mod_base = OTHER
                         note = phosphorothioate linkage
```

| | |
|---|---|
| modified_base | 19..21<br>mod_base = OTHER<br>note = phosphorothioate linkage<br>note = 2-O-methyl modified nucleoside |
| modified_base | 1<br>mod_base = OTHER<br>note = 5-vinylphosphonate<br>note = 2-O-methyl modified nucleoside |
| modified_base | 2<br>mod_base = OTHER<br>note = 2-fluoro-modified nucleoside |
| modified_base | 4<br>mod_base = OTHER<br>note = 2-fluoro-modified nucleoside |
| modified_base | 6<br>mod_base = OTHER<br>note = 2-fluoro-modified nucleoside |
| modified_base | 8<br>mod_base = OTHER<br>note = 2-fluoro-modified nucleoside |
| modified_base | 10<br>mod_base = OTHER<br>note = 2-fluoro-modified nucleoside |
| modified_base | 12<br>mod_base = OTHER<br>note = 2-fluoro-modified nucleoside |
| modified_base | 14<br>mod_base = OTHER<br>note = 2-fluoro-modified nucleoside |
| modified_base | 16<br>mod_base = OTHER<br>note = 2-fluoro-modified nucleoside |
| modified_base | 18<br>mod_base = OTHER<br>note = 2-fluoro-modified nucleoside |
| modified_base | 3<br>mod_base = OTHER<br>note = 2-O-methyl modified nucleoside |
| modified_base | 5<br>mod_base = OTHER<br>note = 2-O-methyl modified nucleoside |
| modified_base | 7<br>mod_base = OTHER<br>note = 2-O-methyl modified nucleoside |
| modified_base | 9<br>mod_base = OTHER<br>note = 2-O-methyl modified nucleoside |
| modified_base | 11<br>mod_base = OTHER<br>note = 2-O-methyl modified nucleoside |
| modified_base | 13<br>mod_base = OTHER<br>note = 2-O-methyl modified nucleoside |
| modified_base | 15<br>mod_base = OTHER<br>note = 2-O-methyl modified nucleoside |
| modified_base | 17<br>mod_base = OTHER<br>note = 2-O-methyl modified nucleoside |

SEQUENCE: 31
ttgtcgagaa agagtgttgt t                                          21

| | |
|---|---|
| SEQ ID NO: 32 | moltype = RNA  length = 21 |
| FEATURE | Location/Qualifiers |
| source | 1..21<br>mol_type = other RNA<br>organism = synthetic construct |
| modified_base | 1..3<br>mod_base = OTHER<br>note = phosphorothioate linkage |
| modified_base | 19..21<br>mod_base = OTHER<br>note = phosphorothioate linkage<br>note = 2-O-methyl modified nucleoside |
| modified_base | 1<br>mod_base = OTHER<br>note = 2-O-methyl modified nucleoside<br>note = 5-vinylphosphonate |

```
modified_base       2
                    mod_base = OTHER
                    note = 2-fluoro-modified nucleoside
modified_base       4
                    mod_base = OTHER
                    note = 2-fluoro-modified nucleoside
modified_base       6
                    mod_base = OTHER
                    note = 2-fluoro-modified nucleoside
modified_base       8
                    mod_base = OTHER
                    note = 2-fluoro-modified nucleoside
modified_base       10
                    mod_base = OTHER
                    note = 2-fluoro-modified nucleoside
modified_base       14
                    mod_base = OTHER
                    note = 2-fluoro-modified nucleoside
modified_base       16
                    mod_base = OTHER
                    note = 2-fluoro-modified nucleoside
modified_base       18
                    mod_base = OTHER
                    note = 2-fluoro-modified nucleoside
modified_base       11..13
                    mod_base = OTHER
                    note = 2-O-methyl modified nucleoside
modified_base       15
                    mod_base = OTHER
                    note = 2-O-methyl modified nucleoside
modified_base       17
                    mod_base = OTHER
                    note = 2-O-methyl modified nucleoside
modified_base       3
                    mod_base = OTHER
                    note = 2-O-methyl modified nucleoside
modified_base       5
                    mod_base = OTHER
                    note = 2-O-methyl modified nucleoside
modified_base       7
                    mod_base = OTHER
                    note = 2-O-methyl modified nucleoside
modified_base       9
                    mod_base = OTHER
                    note = 2-O-methyl modified nucleoside
SEQUENCE: 32
tatgatgtca atctggttgt t                                              21

SEQ ID NO: 33       moltype = RNA   length = 21
FEATURE             Location/Qualifiers
source              1..21
                    mol_type = other RNA
                    organism = synthetic construct
modified_base       1..3
                    mod_base = OTHER
                    note = phosphorothioate linkage
modified_base       19..21
                    mod_base = OTHER
                    note = 2-O-methyl modified nucleoside
                    note = phosphorothioate linkage
modified_base       2
                    mod_base = OTHER
                    note = 2-fluoro-modified nucleoside
modified_base       4
                    mod_base = OTHER
                    note = 2-fluoro-modified nucleoside
modified_base       6
                    mod_base = OTHER
                    note = 2-fluoro-modified nucleoside
modified_base       8
                    mod_base = OTHER
                    note = 2-fluoro-modified nucleoside
modified_base       10
                    mod_base = OTHER
                    note = 2-fluoro-modified nucleoside
modified_base       14
                    mod_base = OTHER
                    note = 2-fluoro-modified nucleoside
```

| | | |
|---|---|---|
| modified_base | 16 | |
| | mod_base = OTHER | |
| | note = 2-fluoro-modified nucleoside | |
| modified_base | 18 | |
| | mod_base = OTHER | |
| | note = 2-fluoro-modified nucleoside | |
| modified_base | 15 | |
| | mod_base = OTHER | |
| | note = 2-O-methyl modified nucleoside | |
| modified_base | 17 | |
| | mod_base = OTHER | |
| | note = 2-O-methyl modified nucleoside | |
| modified_base | 11..13 | |
| | mod_base = OTHER | |
| | note = 2-O-methyl modified nucleoside | |
| modified_base | 1 | |
| | mod_base = OTHER | |
| | note = 2-O-methyl modified nucleoside | |
| modified_base | 3 | |
| | mod_base = OTHER | |
| | note = 2-O-methyl modified nucleoside | |
| modified_base | 5 | |
| | mod_base = OTHER | |
| | note = 2-O-methyl modified nucleoside | |
| modified_base | 7 | |
| | mod_base = OTHER | |
| | note = 2-O-methyl modified nucleoside | |
| modified_base | 9 | |
| | mod_base = OTHER | |
| | note = 2-O-methyl modified nucleoside | |

SEQUENCE: 33
catgatgtca atctggttgt t                                              21

| | | |
|---|---|---|
| SEQ ID NO: 34 | moltype = RNA  length = 21 | |
| FEATURE | Location/Qualifiers | |
| source | 1..21 | |
| | mol_type = other RNA | |
| | organism = synthetic construct | |
| modified_base | 1..3 | |
| | mod_base = OTHER | |
| | note = phosphorothioate linkage | |
| modified_base | 19..21 | |
| | mod_base = OTHER | |
| | note = phosphorothioate linkage | |
| | note = 2-O-methyl modified nucleoside | |
| modified_base | 1 | |
| | mod_base = OTHER | |
| | note = 5-vinylphosphonate | |
| modified_base | 2 | |
| | mod_base = OTHER | |
| | note = 2-fluoro-modified nucleoside | |
| modified_base | 4 | |
| | mod_base = OTHER | |
| | note = 2-fluoro-modified nucleoside | |
| modified_base | 6 | |
| | mod_base = OTHER | |
| | note = 2-fluoro-modified nucleoside | |
| modified_base | 10 | |
| | mod_base = OTHER | |
| | note = 2-fluoro-modified nucleoside | |
| modified_base | 14 | |
| | mod_base = OTHER | |
| | note = 2-fluoro-modified nucleoside | |
| modified_base | 16 | |
| | mod_base = OTHER | |
| | note = 2-fluoro-modified nucleoside | |
| modified_base | 18 | |
| | mod_base = OTHER | |
| | note = 2-fluoro-modified nucleoside | |
| modified_base | 11..13 | |
| | mod_base = OTHER | |
| | note = 2-O-methyl modified nucleoside | |
| modified_base | 15 | |
| | mod_base = OTHER | |
| | note = 2-O-methyl modified nucleoside | |
| modified_base | 17 | |
| | mod_base = OTHER | |
| | note = 2-O-methyl modified nucleoside | |

```
modified_base       1
                    mod_base = OTHER
                    note = 2-O-methyl modified nucleoside
modified_base       3
                    mod_base = OTHER
                    note = 2-O-methyl modified nucleoside
modified_base       5
                    mod_base = OTHER
                    note = 2-O-methyl modified nucleoside
modified_base       7
                    mod_base = OTHER
                    note = 2-O-methyl modified nucleoside
modified_base       9
                    mod_base = OTHER
                    note = 2-O-methyl modified nucleoside
SEQUENCE: 34
tatgatgtca atctggttgt t                                              21

SEQ ID NO: 35       moltype = RNA  length = 21
FEATURE             Location/Qualifiers
source              1..21
                    mol_type = other RNA
                    organism = synthetic construct
modified_base       1..3
                    mod_base = OTHER
                    note = phosphorothioate linkage
modified_base       19..21
                    mod_base = OTHER
                    note = 2-O-methyl modified nucleoside
                    note = phosphorothioate linkage
modified_base       1
                    mod_base = OTHER
                    note = 5-vinylphosphonate
modified_base       2
                    mod_base = OTHER
                    note = 2-fluoro-modified nucleoside
modified_base       4
                    mod_base = OTHER
                    note = 2-fluoro-modified nucleoside
modified_base       6
                    mod_base = OTHER
                    note = 2-fluoro-modified nucleoside
modified_base       8
                    mod_base = OTHER
                    note = 2-fluoro-modified nucleoside
modified_base       10
                    mod_base = OTHER
                    note = 2-fluoro-modified nucleoside
modified_base       14
                    mod_base = OTHER
                    note = 2-fluoro-modified nucleoside
modified_base       16
                    mod_base = OTHER
                    note = 2-fluoro-modified nucleoside
modified_base       18
                    mod_base = OTHER
                    note = 2-fluoro-modified nucleoside
modified_base       15
                    mod_base = OTHER
                    note = 2-O-methyl modified nucleoside
modified_base       17
                    mod_base = OTHER
                    note = 2-O-methyl modified nucleoside
modified_base       1
                    mod_base = OTHER
                    note = 2-O-methyl modified nucleoside
modified_base       3
                    mod_base = OTHER
                    note = 2-O-methyl modified nucleoside
modified_base       5
                    mod_base = OTHER
                    note = 2-O-methyl modified nucleoside
modified_base       7
                    mod_base = OTHER
                    note = 2-O-methyl modified nucleoside
modified_base       9
                    mod_base = OTHER
                    note = 2-O-methyl modified nucleoside
```

```
modified_base               11..13
                            mod_base = OTHER
                            note = 2-O-methyl modified nucleoside
SEQUENCE: 35
tatgatgtca atctggttgt t                                              21

SEQ ID NO: 36               moltype = RNA   length = 21
FEATURE                     Location/Qualifiers
source                      1..21
                            mol_type = other RNA
                            organism = synthetic construct
modified_base               1..3
                            mod_base = OTHER
                            note = phosphorothioate linkage
modified_base               19..21
                            mod_base = OTHER
                            note = phosphorothioate linkage
                            note = 2-O-methyl modified nucleoside
modified_base               2
                            mod_base = OTHER
                            note = 2-fluoro-modified nucleoside
modified_base               4
                            mod_base = OTHER
                            note = 2-fluoro-modified nucleoside
modified_base               6
                            mod_base = OTHER
                            note = 2-fluoro-modified nucleoside
modified_base               8
                            mod_base = OTHER
                            note = 2-fluoro-modified nucleoside
modified_base               10
                            mod_base = OTHER
                            note = 2-fluoro-modified nucleoside
modified_base               14
                            mod_base = OTHER
                            note = 2-fluoro-modified nucleoside
modified_base               16
                            mod_base = OTHER
                            note = 2-fluoro-modified nucleoside
modified_base               18
                            mod_base = OTHER
                            note = 2-fluoro-modified nucleoside
modified_base               11..13
                            mod_base = OTHER
                            note = 2-O-methyl modified nucleoside
modified_base               15
                            mod_base = OTHER
                            note = 2-O-methyl modified nucleoside
modified_base               17
                            mod_base = OTHER
                            note = 2-O-methyl modified nucleoside
modified_base               1
                            mod_base = OTHER
                            note = 2-O-methyl modified nucleoside
modified_base               3
                            mod_base = OTHER
                            note = 2-O-methyl modified nucleoside
modified_base               5
                            mod_base = OTHER
                            note = 2-O-methyl modified nucleoside
modified_base               7
                            mod_base = OTHER
                            note = 2-O-methyl modified nucleoside
modified_base               9
                            mod_base = OTHER
                            note = 2-O-methyl modified nucleoside
SEQUENCE: 36
tatgatgtca atctggttgt t                                              21

SEQ ID NO: 37               moltype = RNA   length = 21
FEATURE                     Location/Qualifiers
source                      1..21
                            mol_type = other RNA
                            organism = synthetic construct
modified_base               1..3
                            mod_base = OTHER
                            note = phosphorothioate linkage
```

```
modified_base        19..21
                     mod_base = OTHER
                     note = 2-O-methyl modified nucleoside
                     note = phosphorothioate linkage
modified_base        1
                     mod_base = OTHER
                     note = 5-vinylphosphonate
                     note = 2-O-methyl modified nucleoside
modified_base        2
                     mod_base = OTHER
                     note = 2-fluoro-modified nucleoside
modified_base        4
                     mod_base = OTHER
                     note = 2-fluoro-modified nucleoside
modified_base        6
                     mod_base = OTHER
                     note = 2-fluoro-modified nucleoside
modified_base        8
                     mod_base = OTHER
                     note = 2-fluoro-modified nucleoside
modified_base        10
                     mod_base = OTHER
                     note = 2-fluoro-modified nucleoside
modified_base        18
                     mod_base = OTHER
                     note = 2-fluoro-modified nucleoside
modified_base        14
                     mod_base = OTHER
                     note = 2-fluoro-modified nucleoside
modified_base        16
                     mod_base = OTHER
                     note = 2-fluoro-modified nucleoside
modified_base        11..13
                     mod_base = OTHER
                     note = 2-O-methyl modified nucleoside
modified_base        15
                     mod_base = OTHER
                     note = 2-O-methyl modified nucleoside
modified_base        17
                     mod_base = OTHER
                     note = 2-O-methyl modified nucleoside
modified_base        3
                     mod_base = OTHER
                     note = 2-O-methyl modified nucleoside
modified_base        5
                     mod_base = OTHER
                     note = 2-O-methyl modified nucleoside
modified_base        7
                     mod_base = OTHER
                     note = 2-O-methyl modified nucleoside
modified_base        9
                     mod_base = OTHER
                     note = 2-O-methyl modified nucleoside
SEQUENCE: 37
tatgatgtca atctggttgt t                                              21

SEQ ID NO: 38        moltype = RNA   length = 21
FEATURE              Location/Qualifiers
source               1..21
                     mol_type = other RNA
                     organism = synthetic construct
modified_base        1..3
                     mod_base = OTHER
                     note = phosphorothioate linkage
modified_base        19..21
                     mod_base = OTHER
                     note = 2-O-methyl modified nucleoside
                     note = phosphorothioate linkage
modified_base        2
                     mod_base = OTHER
                     note = 2-fluoro-modified nucleoside
modified_base        4
                     mod_base = OTHER
                     note = 2-fluoro-modified nucleoside
modified_base        6
                     mod_base = OTHER
                     note = 2-fluoro-modified nucleoside
```

```
modified_base       8
                    mod_base = OTHER
                    note = 2-fluoro-modified nucleoside
modified_base       10
                    mod_base = OTHER
                    note = 2-fluoro-modified nucleoside
modified_base       14
                    mod_base = OTHER
                    note = 2-fluoro-modified nucleoside
modified_base       16
                    mod_base = OTHER
                    note = 2-fluoro-modified nucleoside
modified_base       18
                    mod_base = OTHER
                    note = 2-fluoro-modified nucleoside
modified_base       11..13
                    mod_base = OTHER
                    note = 2-O-methyl modified nucleoside
modified_base       15
                    mod_base = OTHER
                    note = 2-O-methyl modified nucleoside
modified_base       17
                    mod_base = OTHER
                    note = 2-O-methyl modified nucleoside
modified_base       1
                    mod_base = OTHER
                    note = 2-O-methyl modified nucleoside
modified_base       3
                    mod_base = OTHER
                    note = 2-O-methyl modified nucleoside
modified_base       5
                    mod_base = OTHER
                    note = 2-O-methyl modified nucleoside
modified_base       7
                    mod_base = OTHER
                    note = 2-O-methyl modified nucleoside
modified_base       9
                    mod_base = OTHER
                    note = 2-O-methyl modified nucleoside
SEQUENCE: 38
catgatgtca atctggttgt t                                           21

SEQ ID NO: 39       moltype = RNA   length = 21
FEATURE             Location/Qualifiers
source              1..21
                    mol_type = other RNA
                    organism = synthetic construct
modified_base       1..3
                    mod_base = OTHER
                    note = phosphorothioate linkage
modified_base       19..21
                    mod_base = OTHER
                    note = phosphorothioate linkage
                    note = 2-O-methyl modified nucleoside
modified_base       2
                    mod_base = OTHER
                    note = 2-fluoro-modified nucleoside
modified_base       4
                    mod_base = OTHER
                    note = 2-fluoro-modified nucleoside
modified_base       6
                    mod_base = OTHER
                    note = 2-fluoro-modified nucleoside
modified_base       8
                    mod_base = OTHER
                    note = 2-fluoro-modified nucleoside
modified_base       10
                    mod_base = OTHER
                    note = 2-fluoro-modified nucleoside
modified_base       14
                    mod_base = OTHER
                    note = 2-fluoro-modified nucleoside
modified_base       16
                    mod_base = OTHER
                    note = 2-fluoro-modified nucleoside
modified_base       18
                    mod_base = OTHER
                    note = 2-fluoro-modified nucleoside
```

```
modified_base           11..13
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
modified_base           1
                        mod_base = OTHER
                        note = 2-O-methyl modified nucleoside
modified_base           3
                        mod_base = OTHER
                        note = 2-O-methyl modified nucleoside
modified_base           5
                        mod_base = OTHER
                        note = 2-O-methyl modified nucleoside
modified_base           7
                        mod_base = OTHER
                        note = 2-O-methyl modified nucleoside
modified_base           9
                        mod_base = OTHER
                        note = 2-O-methyl modified nucleoside
SEQUENCE: 39
catgatgtca atctggttgt t                                           21

SEQ ID NO: 40           moltype = RNA   length = 21
FEATURE                 Location/Qualifiers
source                  1..21
                        mol_type = other RNA
                        organism = synthetic construct
modified_base           1..3
                        mod_base = OTHER
                        note = phosphorothioate linkage
modified_base           19..21
                        mod_base = OTHER
                        note = 2-O-methyl modified nucleoside
                        note = phosphorothioate linkage
modified_base           2
                        mod_base = OTHER
                        note = 2-fluoro-modified nucleoside
modified_base           4
                        mod_base = OTHER
                        note = 2-fluoro-modified nucleoside
modified_base           6
                        mod_base = OTHER
                        note = 2-fluoro-modified nucleoside
modified_base           8
                        mod_base = OTHER
                        note = 2-fluoro-modified nucleoside
modified_base           10
                        mod_base = OTHER
                        note = 2-fluoro-modified nucleoside
modified_base           14
                        mod_base = OTHER
                        note = 2-fluoro-modified nucleoside
modified_base           16
                        mod_base = OTHER
                        note = 2-fluoro-modified nucleoside
modified_base           18
                        mod_base = OTHER
                        note = 2-fluoro-modified nucleoside
modified_base           11..13
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
modified_base           1
                        mod_base = OTHER
                        note = 2-O-methyl modified nucleoside
modified_base           3
                        mod_base = OTHER
                        note = 2-O-methyl modified nucleoside
```

```
modified_base        5
                     mod_base = OTHER
                     note = 2-O-methyl modified nucleoside
modified_base        7
                     mod_base = OTHER
                     note = 2-O-methyl modified nucleoside
modified_base        9
                     mod_base = OTHER
                     note = 2-O-methyl modified nucleoside
SEQUENCE: 40
catgatgtca atctggttgt t                                              21

SEQ ID NO: 41        moltype = RNA  length = 21
FEATURE              Location/Qualifiers
source               1..21
                     mol_type = other RNA
                     organism = synthetic construct
modified_base        1..3
                     mod_base = OTHER
                     note = phosphorothioate linkage
modified_base        19..21
                     mod_base = OTHER
                     note = 2-O-methyl modified nucleoside
                     note = phosphorothioate linkage
modified_base        2
                     mod_base = OTHER
                     note = 2-fluoro-modified nucleoside
modified_base        4
                     mod_base = OTHER
                     note = 2-fluoro-modified nucleoside
modified_base        6
                     mod_base = OTHER
                     note = 2-fluoro-modified nucleoside
modified_base        8
                     mod_base = OTHER
                     note = 2-fluoro-modified nucleoside
modified_base        10
                     mod_base = OTHER
                     note = 2-fluoro-modified nucleoside
modified_base        14
                     mod_base = OTHER
                     note = 2-fluoro-modified nucleoside
modified_base        16
                     mod_base = OTHER
                     note = 2-fluoro-modified nucleoside
modified_base        18
                     mod_base = OTHER
                     note = 2-fluoro-modified nucleoside
modified_base        11..13
                     mod_base = OTHER
                     note = 2-O-methyl modified nucleoside
modified_base        15
                     mod_base = OTHER
                     note = 2-O-methyl modified nucleoside
modified_base        17
                     mod_base = OTHER
                     note = 2-O-methyl modified nucleoside
modified_base        1
                     mod_base = OTHER
                     note = 2-O-methyl modified nucleoside
modified_base        3
                     mod_base = OTHER
                     note = 2-O-methyl modified nucleoside
modified_base        5
                     mod_base = OTHER
                     note = 2-O-methyl modified nucleoside
modified_base        7
                     mod_base = OTHER
                     note = 2-O-methyl modified nucleoside
modified_base        9
                     mod_base = OTHER
                     note = 2-O-methyl modified nucleoside
SEQUENCE: 41
catgatgtca atctggttgt t                                              21
```

```
SEQ ID NO: 42           moltype = RNA  length = 21
FEATURE                 Location/Qualifiers
source                  1..21
                        mol_type = other RNA
                        organism = synthetic construct
modified_base           1..3
                        mod_base = OTHER
                        note = phosphorothioate linkage
modified_base           19..21
                        mod_base = OTHER
                        note = phosphorothioate linkage
                        note = 2-O-methyl modified nucleoside
modified_base           2
                        mod_base = OTHER
                        note = 2-fluoro-modified nucleoside
modified_base           4
                        mod_base = OTHER
                        note = 2-fluoro-modified nucleoside
modified_base           6
                        mod_base = OTHER
                        note = 2-fluoro-modified nucleoside
modified_base           8
                        mod_base = OTHER
                        note = 2-fluoro-modified nucleoside
modified_base           10
                        mod_base = OTHER
                        note = 2-fluoro-modified nucleoside
modified_base           14
                        mod_base = OTHER
                        note = 2-fluoro-modified nucleoside
modified_base           16
                        mod_base = OTHER
                        note = 2-fluoro-modified nucleoside
modified_base           18
                        mod_base = OTHER
                        note = 2-fluoro-modified nucleoside
modified_base           11..13
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
modified_base           1
                        mod_base = OTHER
                        note = 2-O-methyl modified nucleoside
modified_base           3
                        mod_base = OTHER
                        note = 2-O-methyl modified nucleoside
modified_base           5
                        mod_base = OTHER
                        note = 2-O-methyl modified nucleoside
modified_base           7
                        mod_base = OTHER
                        note = 2-O-methyl modified nucleoside
modified_base           9
                        mod_base = OTHER
                        note = 2-O-methyl modified nucleoside
SEQUENCE: 42
catgatgtca atctggttgt t                                                   21

SEQ ID NO: 43           moltype = RNA  length = 21
FEATURE                 Location/Qualifiers
source                  1..21
                        mol_type = other RNA
                        organism = synthetic construct
modified_base           1..3
                        mod_base = OTHER
                        note = phosphorothioate linkage
modified_base           19..21
                        mod_base = OTHER
                        note = phosphorothioate linkage
                        note = 2-O-methyl modified nucleoside
modified_base           2
                        mod_base = OTHER
                        note = 2-fluoro-modified nucleoside
```

```
modified_base           4
                        mod_base = OTHER
                        note = 2-fluoro-modified nucleoside
modified_base           6
                        mod_base = OTHER
                        note = 2-fluoro-modified nucleoside
modified_base           8
                        mod_base = OTHER
                        note = 2-fluoro-modified nucleoside
modified_base           10
                        mod_base = OTHER
                        note = 2-fluoro-modified nucleoside
modified_base           14
                        mod_base = OTHER
                        note = 2-fluoro-modified nucleoside
modified_base           16
                        mod_base = OTHER
                        note = 2-fluoro-modified nucleoside
modified_base           18
                        mod_base = OTHER
                        note = 2-fluoro-modified nucleoside
modified_base           1
                        mod_base = OTHER
                        note = 2-O-methyl modified nucleoside
modified_base           3
                        mod_base = OTHER
                        note = 2-O-methyl modified nucleoside
modified_base           5
                        mod_base = OTHER
                        note = 2-O-methyl modified nucleoside
modified_base           7
                        mod_base = OTHER
                        note = 2-O-methyl modified nucleoside
modified_base           9
                        mod_base = OTHER
                        note = 2-O-methyl modified nucleoside
modified_base           11..13
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
SEQUENCE: 43
catgatgtca atctggttgt t                                                  21

SEQ ID NO: 44           moltype = RNA   length = 21
FEATURE                 Location/Qualifiers
source                  1..21
                        mol_type = other RNA
                        organism = synthetic construct
modified_base           1..3
                        mod_base = OTHER
                        note = phosphorothioate linkage
modified_base           19..21
                        mod_base = OTHER
                        note = 2-O-methyl modified nucleoside
                        note = phosphorothioate linkage
modified_base           2
                        mod_base = OTHER
                        note = 2-fluoro-modified nucleoside
modified_base           4
                        mod_base = OTHER
                        note = 2-fluoro-modified nucleoside
modified_base           6
                        mod_base = OTHER
                        note = 2-fluoro-modified nucleoside
modified_base           8
                        mod_base = OTHER
                        note = 2-fluoro-modified nucleoside
modified_base           10
                        mod_base = OTHER
                        note = 2-fluoro-modified nucleoside
modified_base           14
                        mod_base = OTHER
                        note = 2-fluoro-modified nucleoside
```

-continued

```
modified_base      16
                   mod_base = OTHER
                   note = 2-fluoro-modified nucleoside
modified_base      18
                   mod_base = OTHER
                   note = 2-fluoro-modified nucleoside
modified_base      1
                   mod_base = OTHER
                   note = 2-O-methyl modified nucleoside
modified_base      3
                   mod_base = OTHER
                   note = 2-O-methyl modified nucleoside
modified_base      5
                   mod_base = OTHER
                   note = 2-O-methyl modified nucleoside
modified_base      7
                   mod_base = OTHER
                   note = 2-O-methyl modified nucleoside
modified_base      9
                   mod_base = OTHER
                   note = 2-O-methyl modified nucleoside
modified_base      11..13
                   mod_base = OTHER
                   note = 2-O-methyl modified nucleoside
modified_base      15
                   mod_base = OTHER
                   note = 2-O-methyl modified nucleoside
modified_base      17
                   mod_base = OTHER
                   note = 2-O-methyl modified nucleoside
SEQUENCE: 44
catgatgtca atctggttgt t                                              21

SEQ ID NO: 45      moltype = RNA  length = 21
FEATURE            Location/Qualifiers
source             1..21
                   mol_type = other RNA
                   organism = synthetic construct
modified_base      1..3
                   mod_base = OTHER
                   note = phosphorothioate linkage
modified_base      19..21
                   mod_base = OTHER
                   note = phosphorothioate linkage
modified_base      2
                   mod_base = OTHER
                   note = 2-fluoro-modified nucleoside
modified_base      6
                   mod_base = OTHER
                   note = 2-fluoro-modified nucleoside
modified_base      8
                   mod_base = OTHER
                   note = 2-fluoro-modified nucleoside
modified_base      14
                   mod_base = OTHER
                   note = 2-fluoro-modified nucleoside
modified_base      16
                   mod_base = OTHER
                   note = 2-fluoro-modified nucleoside
modified_base      17..21
                   mod_base = OTHER
                   note = 2-O-methyl modified nucleoside
modified_base      1
                   mod_base = OTHER
                   note = 2-O-methyl modified nucleoside
modified_base      3..5
                   mod_base = OTHER
                   note = 2-O-methyl modified nucleoside
modified_base      7
                   mod_base = OTHER
                   note = 2-O-methyl modified nucleoside
modified_base      9..13
                   mod_base = OTHER
                   note = 2-O-methyl modified nucleoside
modified_base      15
                   mod_base = OTHER
                   note = 2-O-methyl modified nucleoside
SEQUENCE: 45
tctgagttca cctttgtagt t                                              21
```

```
SEQ ID NO: 46           moltype = RNA  length = 21
FEATURE                 Location/Qualifiers
source                  1..21
                        mol_type = other RNA
                        organism = synthetic construct
modified_base           1..3
                        mod_base = OTHER
                        note = phosphorothioate linkage
modified_base           19..21
                        mod_base = OTHER
                        note = phosphorothioate linkage
modified_base           2
                        mod_base = OTHER
                        note = 2-fluoro-modified nucleoside
modified_base           6
                        mod_base = OTHER
                        note = 2-fluoro-modified nucleoside
modified_base           8
                        mod_base = OTHER
                        note = 2-fluoro-modified nucleoside
modified_base           14
                        mod_base = OTHER
                        note = 2-fluoro-modified nucleoside
modified_base           16
                        mod_base = OTHER
                        note = 2-fluoro-modified nucleoside
modified_base           1
                        mod_base = OTHER
                        note = 2-O-methyl modified nucleoside
modified_base           3..5
                        mod_base = OTHER
                        note = 2-O-methyl modified nucleoside
modified_base           7
                        mod_base = OTHER
                        note = 2-O-methyl modified nucleoside
modified_base           9..13
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
modified_base           17..21
                        mod_base = OTHER
                        note = 2-O-methyl modified nucleoside
SEQUENCE: 46
tctgagttca cctttgtagt t                                                  21

SEQ ID NO: 47           moltype = RNA  length = 21
FEATURE                 Location/Qualifiers
source                  1..21
                        mol_type = other RNA
                        organism = synthetic construct
modified_base           19..21
                        mod_base = OTHER
                        note = phosphorothioate linkage
modified_base           6..10
                        mod_base = OTHER
                        note = 2-fluoro-modified nucleoside
modified_base           1..5
                        mod_base = OTHER
                        note = 2-O-methyl modified nucleoside
modified_base           11..21
                        mod_base = OTHER
                        note = 2-O-methyl modified nucleoside
SEQUENCE: 47
tctacaaagg tgaactcaat t                                                  21

SEQ ID NO: 48           moltype = RNA  length = 21
FEATURE                 Location/Qualifiers
source                  1..21
                        mol_type = other RNA
                        organism = synthetic construct
modified_base           19..21
                        mod_base = OTHER
                        note = phosphorothioate linkage
```

```
modified_base         6..10
                      mod_base = OTHER
                      note = 2-fluoro-modified nucleoside
modified_base         1..5
                      mod_base = OTHER
                      note = 2-O-methyl modified nucleoside
modified_base         11..21
                      mod_base = OTHER
                      note = 2-O-methyl modified nucleoside
SEQUENCE: 48
tctacaaagg tgaactcaat t                                        21

SEQ ID NO: 49         moltype = RNA  length = 21
FEATURE               Location/Qualifiers
source                1..21
                      mol_type = other RNA
                      organism = synthetic construct
modified_base         1..3
                      mod_base = OTHER
                      note = phosphorothioate linkage
modified_base         19..21
                      mod_base = OTHER
                      note = 2-O-methyl modified nucleoside
                      note = phosphorothioate linkage
modified_base         1
                      mod_base = OTHER
                      note = 5-vinylphosphonate
                      note = 2-O-methyl modified nucleoside
modified_base         2
                      mod_base = OTHER
                      note = 2-fluoro-modified nucleoside
modified_base         4
                      mod_base = OTHER
                      note = 2-fluoro-modified nucleoside
modified_base         6
                      mod_base = OTHER
                      note = 2-fluoro-modified nucleoside
modified_base         8
                      mod_base = OTHER
                      note = 2-fluoro-modified nucleoside
modified_base         10
                      mod_base = OTHER
                      note = 2-fluoro-modified nucleoside
modified_base         12
                      mod_base = OTHER
                      note = 2-fluoro-modified nucleoside
modified_base         14
                      mod_base = OTHER
                      note = 2-fluoro-modified nucleoside
modified_base         16
                      mod_base = OTHER
                      note = 2-fluoro-modified nucleoside
modified_base         18
                      mod_base = OTHER
                      note = 2-fluoro-modified nucleoside
modified_base         3
                      mod_base = OTHER
                      note = 2-O-methyl modified nucleoside
modified_base         5
                      mod_base = OTHER
                      note = 2-O-methyl modified nucleoside
modified_base         7
                      mod_base = OTHER
                      note = 2-O-methyl modified nucleoside
modified_base         9
                      mod_base = OTHER
                      note = 2-O-methyl modified nucleoside
modified_base         11
                      mod_base = OTHER
                      note = 2-O-methyl modified nucleoside
modified_base         13
                      mod_base = OTHER
                      note = 2-O-methyl modified nucleoside
```

-continued

```
modified_base       15
                    mod_base = OTHER
                    note = 2-O-methyl modified nucleoside
modified_base       17
                    mod_base = OTHER
                    note = 2-O-methyl modified nucleoside
SEQUENCE: 49
ttgagttcac cttttgtagat t                                          21

SEQ ID NO: 50       moltype = RNA  length = 21
FEATURE             Location/Qualifiers
source              1..21
                    mol_type = other RNA
                    organism = synthetic construct
modified_base       1..3
                    mod_base = OTHER
                    note = phosphorothioate linkage
modified_base       19..21
                    mod_base = OTHER
                    note = 2-O-methyl modified nucleoside
                    note = phosphorothioate linkage
modified_base       1
                    mod_base = OTHER
                    note = 2-O-methyl modified nucleoside
                    note = 5-vinylphosphonate
modified_base       2
                    mod_base = OTHER
                    note = 2-fluoro-modified nucleoside
modified_base       6
                    mod_base = OTHER
                    note = 2-fluoro-modified nucleoside
modified_base       8
                    mod_base = OTHER
                    note = 2-fluoro-modified nucleoside
modified_base       10
                    mod_base = OTHER
                    note = 2-fluoro-modified nucleoside
modified_base       12
                    mod_base = OTHER
                    note = 2-fluoro-modified nucleoside
modified_base       14
                    mod_base = OTHER
                    note = 2-fluoro-modified nucleoside
modified_base       16
                    mod_base = OTHER
                    note = 2-fluoro-modified nucleoside
modified_base       18
                    mod_base = OTHER
                    note = 2-fluoro-modified nucleoside
modified_base       3..5
                    mod_base = OTHER
                    note = 2-O-methyl modified nucleoside
modified_base       7
                    mod_base = OTHER
                    note = 2-O-methyl modified nucleoside
modified_base       9
                    mod_base = OTHER
                    note = 2-O-methyl modified nucleoside
modified_base       11
                    mod_base = OTHER
                    note = 2-O-methyl modified nucleoside
modified_base       13
                    mod_base = OTHER
                    note = 2-O-methyl modified nucleoside
modified_base       15
                    mod_base = OTHER
                    note = 2-O-methyl modified nucleoside
modified_base       17
                    mod_base = OTHER
                    note = 2-O-methyl modified nucleoside
SEQUENCE: 50
ttgagttcac ctttgtagat t                                           21
```